US012643946B2

(12) United States Patent
    Hikichi et al.

(10) Patent No.: US 12,643,946 B2
(45) Date of Patent: Jun. 2, 2026

(54) ANTIBODY, NUCLEIC ACID, CELL, AND PHARMACEUTICAL

(71) Applicants: NB HEALTH LABORATORY CO., LTD., Hokkaido (JP); THE UNIVERSITY OF TOKYO, Tokyo (JP)

(72) Inventors: Megumi Hikichi, Hokkaido (JP); Masami Ashida, Hokkaido (JP); Miki Nakagawa, Hokkaido (JP); Masahiko Shinagawa, Hokkaido (JP); Ryoma Tanaka, Hokkaido (JP); Kiyoshi Takayama, Hokkaido (JP); Junken Aoki, Tokyo (JP)

(73) Assignees: NB HEALTH LABORATORY CO., LTD., Hokkaido (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 18/881,999

(22) PCT Filed: Oct. 13, 2023

(86) PCT No.: PCT/JP2023/037183
    § 371 (c)(1),
    (2) Date: Jan. 7, 2025

(87) PCT Pub. No.: WO2024/085081
    PCT Pub. Date: Apr. 25, 2024

(65) Prior Publication Data
    US 2025/0171532 A1     May 29, 2025

Related U.S. Application Data

(60) Provisional application No. 63/417,197, filed on Oct. 18, 2022.

(30) Foreign Application Priority Data

Apr. 14, 2023     (JP) ................................. 2023-066688

(51) Int. Cl.
    *C07K 16/28*     (2006.01)
    *A61K 47/68*     (2017.01)
(52) U.S. Cl.
    CPC .......... *C07K 16/28* (2013.01); *A61K 47/6801* (2017.08); *C07K 2317/24* (2013.01); *C07K 2317/75* (2013.01); *C07K 2317/92* (2013.01)
(58) Field of Classification Search
    None
    See application file for complete search history.

(56) References Cited

U.S. PATENT DOCUMENTS

2007/0105133 A1     5/2007    Clarke et al.
2023/0181671 A1     6/2023    Illingworth et al.

FOREIGN PATENT DOCUMENTS

JP      2008-546387     12/2008
WO      2004/044580     5/2004
WO      2005/009469     2/2005

OTHER PUBLICATIONS

International Preliminary Report on Patentability issued Mar. 1, 2025, in International Application No. PCT/JP2023/037183.
International Search Report issued Dec. 19, 2023 in corresponding International Application No. PCT/JP2023/037183.
Aikawa, S., et al., "Lysophosphatidic acid as a lipid mediator with multiple biological actions", J Biochem, 2014; 157:81-89.
Yung, Y. C., et al., "LPA receptor signaling: pharmacology, physiology, and pathophysiology", J Lipid Res, 2014; 55: 1192-1214.
Kihara, Y., et al., "Lysophospholipid receptor nomenclature review: IUPHAR Review 8", Br J Pharmacol, 2014; 171: 3575-3594.
Kano, K., et al., "Lysophospholipid Mediators in Health and Disease", Annu Rev Pathol, 2022; 17: 459-483.
Meduri, B., et al., "Lysophosphatidic acid (LPA) receptor modulators: Structural features and recent development", Eur J Med Chem, 2021; 222: 113574.
Tager, A. M., et al., "The lysophosphatidic acid receptor LPA1 links pulmonary fibrosis to lung injury by mediating fibroblast recruitment and vascular leak", Nat Med, 2007; 14: 45-54.
Swaney, J. S., et al., "A novel, orally active LPA(1) receptor antagonist inhibits lung fibrosis in the mouse bleomycin model", Br J Pharmacol, 2010; 160: 1699-1713.
Palmer, S. M., et al., "Randomized, Double-Blind, Placebo-Controlled, Phase 2 Trial of BMS-986020, a Lysophosphatidic Acid Receptor Antagonist for the Treatment of Idiopathic Pulmonary Fibrosis", Chest, 2018; 154: 1061-1069.
Cheng P. T. W., et al., "Discovery of an Oxycyclohexyl Acid Lysophosphatidic Acid Receptor 1 (LPA1) Antagonist BMS-986278 for the Treatment of Pulmonary Fibrotic Diseases", J Med Chem, 2021; 64: 15549-15581.
Kim, D., et al., "Lysophosphatidic acid increases mesangial cell proliferation in models of diabetic nephropathy via Rac1/MAPK/KLF5 signaling", Exp Mol Med, 2019; 51: 1-10.
Ueda, H., "LPA receptor signaling as a therapeutic target for radical treatment of neuropathic pain and fibromyalgia", Pain Manag, 2019; 10:43-53.
Ueda, H., et al., "Lysophosphatidic Acid Receptor 1- and 3-Mediated Hyperalgesia and Hypoalgesia in Diabetic Neuropathic Pain Models in Mice", Cells, 2020; 9: 1906.
Srikanth, M., et al., "Lysophosphatidic acid and its receptor LPA1 mediate carrageenan induced inflammatory pain in mice", Eur J Pharmacol, 2018; 841: 49-56.

(Continued)

*Primary Examiner* — Ruixiang Li
(74) *Attorney, Agent, or Firm* — Wenderoth, Lind & Ponack, L.L.P.

(57)     ABSTRACT

To provide an antibody that specifically binds to an extracellular domain of human LPA1, wherein the antibody does not specifically bind to an extracellular domain of human LPA2 and does not specifically bind to an extracellular domain of human LPA3. Preferably, the antibody includes an activity of blocking an LPA1-dependent cell function. Also, a nucleic acid encoding the antibody, a cell including the nucleic acid, and a medicament including the antibody as an active ingredient are provided.

11 Claims, 25 Drawing Sheets

Specification includes a Sequence Listing.

(56)            References Cited

OTHER PUBLICATIONS

Miyabe, Y., et al., "Necessity of lysophosphatidic acid receptor 1 for development of arthritis", Arthritis Rheum, 2013; 65: 2037-2047.

Zhao, J., et al., "Lysophosphatidic acid receptor 1 antagonist ki16425 blunts abdominal and systemic inflammation in a mouse model of peritoneal sepsis", Transl Res, 2015; 166: 80-88.

Szepanowski, F., et al., "LPA1 signaling drives Schwann cell dedifferentiation in experimental autoimmune neuritis", Neuroinflammation, 2021; 18: 293.

D'Souza, K., et al., "Lysophosphatidic Acid Signaling in Obesity and Insulin Resistance", Nutrients, 2018; 10: 399.

Zhou, Y., et al., "Lysophosphatidic acid and its receptors: pharmacology and therapeutic potential in atherosclerosis and vascular disease", Pharmacol Ther, 2019; 204: 107404.

Gaire, B. P., et al., "BMS-986020, a Specific LPA1 Antagonist, Provides Neuroprotection against Ischemic Stroke in Mice", Antioxidants, 2020; 9: 1097.

Naruse, T., et al., "Effects of a lysophosphatidic acid receptor 1 antagonist on hypertensive renal injury in Dahl-Iwai salt-sensitive rats", J Pharmacol Sci, 2022; 149 :179-188.

Yung, Y. C., et al., "Lysophosphatidic acid signaling may initiate fetal hydrocephalus", Sci Transl Med, 2011; 3: 99ra87.

Moreno-Fernandez, R. D., et al., "Stress, Depression, Resilience and Ageing: A Role for the LPA-LPA1 Pathway", Curr Neuropharmacol, 2018; 16: 271-283.

Boucharaba, A., et al., "The type 1 lysophosphatidic acid receptor is a target for therapy in bone metastases", Proc Natl Acad Sci USA, 2006; 103: 9643-9648.

Zhao, P. F., et al., "LPA receptor1 antagonists as anticancer agents suppress human lung tumours", Eur J Pharmacol, 2019; 868: 172886.

Sakamoto, K., et al., "Effect of ASP6432, a Novel Type 1 Lysophosphatidic Acid Receptor Antagonist, on Urethral Function and Prostate Cell Proliferation", J Pharmacol Exp Ther, 2018; 366: 390-396.

Sakamoto, K., et al., "Modulation of urinary frequency via type 1 lysophosphatidic acid receptors: Effect of the novel antagonist ASP6432 in conscious rats", Eur J Pharmacol, 2019; 853: 11-17.

Yang, C., et al., "The role of lysophosphatidic acid receptor (LPA1) in the oxygen-induced retinal ganglion cell degeneration", Invest Ophthalmol Vis Sci, 2009; 50: 1290-1298.

Gobeil, F., Jr., et al., "Modulation of Pro-inflammatory Gene Expression by Nuclear Lysophosphatidic Acid Receptor Type-1", The Journal of Biological Chemistry, 2003, vol. 278, No. 40, pp. 38875-38883.

Jung, J. H., et al., "Isolation of Single Chain Antibodies Specific to Lysophosphatidic Acid Receptor 1 (LPA1) from a M13 Phage Display Library Using Purified LPA1 Stabilized in Nanodiscs", Bulletin of Korean Chemical Society, 2019, vol. 40, pp. 680-685.

Zheng, Y., et al., "Altered expression and functional profile of lysophosphatidic acid receptors in mitogen-activated human blood T lymphocytes", The FASEB Journal, 2000, pp. 1-16.

Budnik, L. T., et al., "Lysophosphatidic Acid Signals through Mitogen-Activated Protein Kinase-Extracellular Signal Regulated Kinase in Ovarian Theca Cells Expressing the LPA1/edg2-Receptor: Involvement of a Nonclassical Pathway?", Molecular Endocrinology, 2003, vol. 17, No. 8, pp. 1599-1600.

Office Action issued Jul. 4, 2024 in corresponding Japanese Application No. 2024-510411, with machine translation.

FIG. 6E
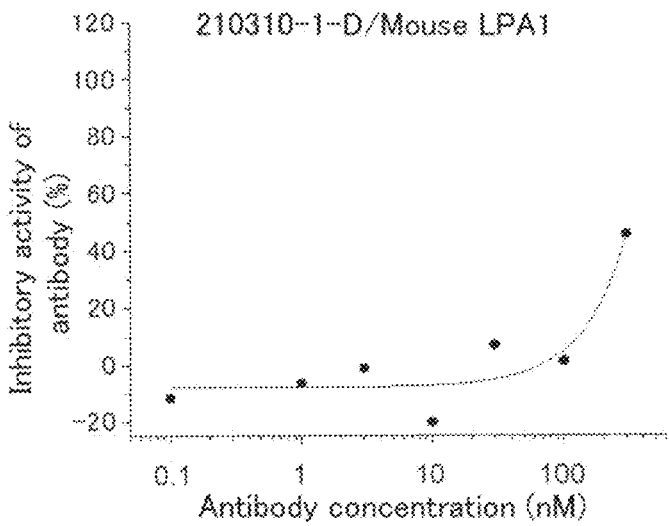
FIG. 6F
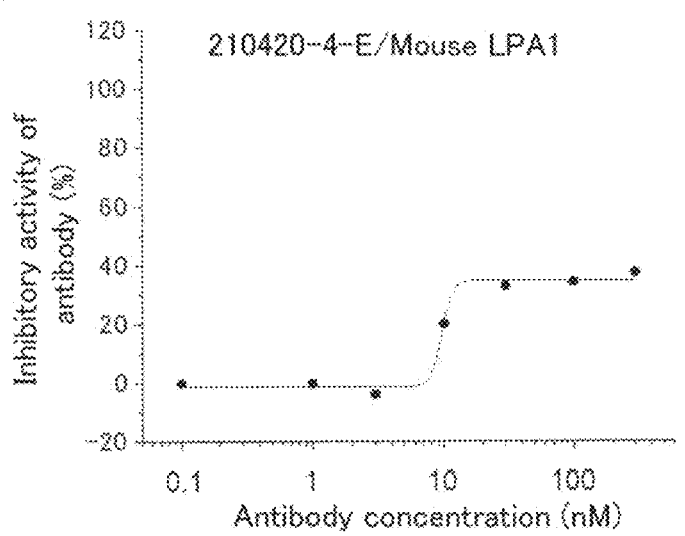
FIG. 6G

FIG. 12E 210309-4-A

SEQUENCE LISTING

Sequence total quantity: 130
SEQ ID NO: 1          moltype = AA  length = 10
FEATURE               Location/Qualifiers
source                1..10
                      mol_type = protein
                      organism = Mus musculus
SEQUENCE: 1

```
GYTFTSYGIS                                                      10

SEQ ID NO: 2            moltype = AA   length = 17
FEATURE                 Location/Qualifiers
source                  1..17
                        mol_type = protein
                        organism = Mus musculus
SEQUENCE: 2
EIYPRSGNTY YNEKFKG                                              17

SEQ ID NO: 3            moltype = AA   length = 15
FEATURE                 Location/Qualifiers
source                  1..15
                        mol_type = protein
                        organism = Mus musculus
SEQUENCE: 3
ARESISRRLG WNFDV                                                15

SEQ ID NO: 4            moltype = AA   length = 11
FEATURE                 Location/Qualifiers
source                  1..11
                        mol_type = protein
                        organism = Mus musculus
SEQUENCE: 4
RASENIYSFL A                                                    11

SEQ ID NO: 5            moltype = AA   length = 7
FEATURE                 Location/Qualifiers
source                  1..7
                        mol_type = protein
                        organism = Mus musculus
SEQUENCE: 5
NAKTLTE                                                         7

SEQ ID NO: 6            moltype = AA   length = 9
FEATURE                 Location/Qualifiers
source                  1..9
                        mol_type = protein
                        organism = Mus musculus
SEQUENCE: 6
QHHYGPPLT                                                       9

SEQ ID NO: 7            moltype = AA   length = 122
FEATURE                 Location/Qualifiers
source                  1..122
                        mol_type = protein
                        organism = Mus musculus
SEQUENCE: 7
QVQLQQSGAE LARPGASVKL SCKASGYTFT SYGISWVKQR TGQGLEWIGE IYPRSGNTYY  60
NEKFKGKATL TADKSSSTAY MELRSLTSED SAVYFCARES ISRRLGWNFD VWGTGTTVTV 120
SS                                                             122

SEQ ID NO: 8            moltype = DNA   length = 366
FEATURE                 Location/Qualifiers
source                  1..366
                        mol_type = other DNA
                        organism = Mus musculus
CDS                     1..366
                        protein_id = 7
                        translation = QVQLQQSGAELARPGASVKLSCKASGYTFTSYGISWVKQRTGQGLE
                        WIGEIYPRSGNTYYNEKFKGKATLTADKSSSTAYMELRSLTSEDSAVYFCARESISRRL
                        GWNFDVWGTGTTVTVSS
SEQUENCE: 8
caggttcagc tgcagcagtc tggagctgag ctggcgaggc ctggggcttc agtgaagctg  60
tcctgcaagg cttctggcta caccttcaca agctatggta taagctgggt gaagcagaga 120
actggacagg gccttgagtg gattggagag atttatccta gaagtggtaa tacttactac 180
aatgagaagt tcaagggcaa ggccacactg actgcagaca atcctccag cacagcgtac 240
atggagctcc gcagcctgac atctgaggac tctgcggtct atttctgtgc aagagagtct 300
atatcacgac ggctaggctg gaacttcgat gtctggggca cagggaccac ggtcaccgtc 360
tcctca                                                         366

SEQ ID NO: 9            moltype = AA   length = 107
FEATURE                 Location/Qualifiers
source                  1..107
                        mol_type = protein
                        organism = Mus musculus
SEQUENCE: 9
DIHMTQSPAS LSASVGETVT ITCRASENIY SFLAWYQQKQ GKSPHLVVYN AKTLTEGVPS  60
RFSGSGSGTH FSLKINSLQP EDFGIYYCQH HYGPPLTFGA GTKLELK              107
```

```
SEQ ID NO: 10           moltype = DNA  length = 321
FEATURE                 Location/Qualifiers
source                  1..321
                        mol_type = other DNA
                        organism = Mus musculus
CDS                     1..321
                        protein_id = 9
                        translation = DIHMTQSPASLSASVGETVTITCRASENIYSFLAWYQQKGKSPHL
                          VVYNAKTLTEGVPSRFSGSGSGTHFSLKINSLQPEDFGIYYCQHHYGPPLTFGAGTKLE
                          LK
SEQUENCE: 10
gacatccaca tgactcagtc tccagcctcc ctatctgcat ctgtgggaga aactgtcacc   60
atcacatgtc gagcaagtga gaatatttac agttttttag catggtatca gcagaaacag  120
ggaaaatctc ctcacctcgt ggtctacaat gcaaagacct taacagaagg tgtgccatca  180
aggttcagtg gcagtggatc aggcacacac ttttctctga agatcaacag ccttcagcct  240
gaagattttg ggatttatta ctgtcaacat cattatggtc ctcctctcac gttcggtgct  300
gggaccaagc tggagctgaa a                                             321

SEQ ID NO: 11           moltype = AA  length = 10
FEATURE                 Location/Qualifiers
source                  1..10
                        mol_type = protein
                        organism = Mus musculus
SEQUENCE: 11
GYSFTAYGIS                                                           10

SEQ ID NO: 12           moltype = AA  length = 17
FEATURE                 Location/Qualifiers
source                  1..17
                        mol_type = protein
                        organism = Mus musculus
SEQUENCE: 12
EIYPRSGNTY YSEKFKG                                                   17

SEQ ID NO: 13           moltype = AA  length = 15
FEATURE                 Location/Qualifiers
source                  1..15
                        mol_type = protein
                        organism = Mus musculus
SEQUENCE: 13
ARESLLKRLG WYFDV                                                     15

SEQ ID NO: 14           moltype = AA  length = 11
FEATURE                 Location/Qualifiers
source                  1..11
                        mol_type = protein
                        organism = Mus musculus
SEQUENCE: 14
RASQNIYSFL A                                                         11

SEQ ID NO: 15           moltype = AA  length = 7
FEATURE                 Location/Qualifiers
source                  1..7
                        mol_type = protein
                        organism = Mus musculus
SEQUENCE: 15
NAKTLAE                                                              7

SEQ ID NO: 16           moltype = AA  length = 9
FEATURE                 Location/Qualifiers
source                  1..9
                        mol_type = protein
                        organism = Mus musculus
SEQUENCE: 16
QHHYGPPLT                                                           9

SEQ ID NO: 17           moltype = AA  length = 122
FEATURE                 Location/Qualifiers
source                  1..122
                        mol_type = protein
                        organism = Mus musculus
SEQUENCE: 17
QVHLQQSGAE LARPGASVKL SCKASGYSFT AYGISWVQQR TGQGLEWIGE IYPRSGNTYY    60
SEKFKGKATL TADKSSSTAY MELRSLTSED SAVYFCARES LLKRLGWYFD VWGTGTTVTV   120
SS                                                                 122

SEQ ID NO: 18           moltype = DNA  length = 366
FEATURE                 Location/Qualifiers
```

-continued

```
source                   1..366
                         mol_type = other DNA
                         organism = Mus musculus
CDS                      1..366
                         protein_id = 17
                         translation = QVHLQQSGAELARPGASVKLSCKASGYSFTAYGISWVQQRTGQGLE
                         WIGEIYPRSGNTYYSEKFKGKATLTADKSSSTAYMELRSLTSEDSAVYFCARESLLKRL
                         GWYFDVWGTGTTVTVSS
SEQUENCE: 18
caggttcatc tgcagcagtc tggagctgag ctggcgaggc ctggggcttc agtgaagctg   60
tcctgcaagg cttctggcta cagcttcaca gcctatggta taagctgggt gcagcagaga  120
actggacagg gccttgagtg gattggagag atttatccaa gaagtggtaa tacttactac  180
agtgagaagt tcaagggcaa ggccacactg actgcagaca atcctccag tacagcgtac  240
atggagctcc gcagcctgac atctgaggac tctgcggtct atttctgtgc aagagagtct  300
ctattaaaac ggctaggctg gtacttcgat gtctggggca cagggaccac ggtcaccgtc  360
tcctca                                                            366

SEQ ID NO: 19          moltype = AA  length = 107
FEATURE                Location/Qualifiers
source                 1..107
                       mol_type = protein
                       organism = Mus musculus
SEQUENCE: 19
DIQMTQSPAS LSASVGETVT ITCRASQNIY SFLAWYQQKQ GNSPQLLVYN AKTLAEGVPS   60
RFSGSGSGTQ FSLKINSLQP EDFGSYYCQH HYGPPLTFGV GTKLELK                 107

SEQ ID NO: 20          moltype = DNA  length = 321
FEATURE                Location/Qualifiers
source                 1..321
                       mol_type = other DNA
                       organism = Mus musculus
CDS                    1..321
                       protein_id = 19
                       translation = DIQMTQSPASLSASVGETVTITCRASQNIYSFLAWYQQKQGNSPQL
                        LVYNAKTLAEGVPSRFSGSGSGTQFSLKINSLQPEDFGSYYCQHHYGPPLTFGVGTKLE
                        LK
SEQUENCE: 20
gacatccaga tgactcagtc tccagcctcc ctatctgcat ctgtgggaga aactgtcacc   60
atcacatgtc gagcaagtca gaatatttac agttttttag catggtatca gcagaaacag  120
ggaaattctc ctcagctcct ggtctataat gcaaaaacct tagcagaagg tgtgccatca  180
aggttcagtg gcagtggatc aggcacacag ttttctctga agatcaacag cctgcagcct  240
gaagattttg ggagttatta ctgtcaacat cattatggtc ctcctctcac gttcggtgtt  300
gggaccaagc tggagctgaa a                                             321

SEQ ID NO: 21          moltype = AA  length = 10
FEATURE                Location/Qualifiers
source                 1..10
                       mol_type = protein
                       organism = Mus musculus
SEQUENCE: 21
GYTFTSYGIS                                                          10

SEQ ID NO: 22          moltype = AA  length = 17
FEATURE                Location/Qualifiers
source                 1..17
                       mol_type = protein
                       organism = Mus musculus
SEQUENCE: 22
EIYPRSGVTY YNEKFKG                                                  17

SEQ ID NO: 23          moltype = AA  length = 15
FEATURE                Location/Qualifiers
source                 1..15
                       mol_type = protein
                       organism = Mus musculus
SEQUENCE: 23
ARESISLRLG WYFDV                                                    15

SEQ ID NO: 24          moltype = AA  length = 11
FEATURE                Location/Qualifiers
source                 1..11
                       mol_type = protein
                       organism = Mus musculus
SEQUENCE: 24
RASENIYRFL A                                                        11

SEQ ID NO: 25          moltype = AA  length = 7
FEATURE                Location/Qualifiers
source                 1..7
```

```
                              mol_type = protein
                              organism = Mus musculus
SEQUENCE: 25
NAKTLAE                                                                    7

SEQ ID NO: 26             moltype = AA  length = 9
FEATURE                   Location/Qualifiers
source                    1..9
                          mol_type = protein
                          organism = Mus musculus
SEQUENCE: 26
QHHYGPPLT                                                                   9

SEQ ID NO: 27             moltype = AA  length = 122
FEATURE                   Location/Qualifiers
source                    1..122
                          mol_type = protein
                          organism = Mus musculus
SEQUENCE: 27
QVQLQQSGAE LARPGASMKL SCRASGYTFT SYGISWVKQR TGQGLEWIGE IYPRSGVTYY  60
NEKFKGRATL TADKSSSTAF MELRSLTSED SAVYFCARES ISLRLGWYFD VWGTGTTVTV  120
SS                                                                         122

SEQ ID NO: 28             moltype = DNA  length = 366
FEATURE                   Location/Qualifiers
source                    1..366
                          mol_type = other DNA
                          organism = Mus musculus
CDS                       1..366
                          protein_id = 27
                          translation = QVQLQQSGAELARPGASMKLSCRASGYTFTSYGISWVKQRTGQGLE
                          WIGEIYPRSGVTYYNEKFKGRATLTADKSSSTAFMELRSLTSEDSAVYFCARESISLRL
                          GWYFDVWGTGTTVTVSS
SEQUENCE: 28
caggttcagc tgcagcagtc tggagctgag ctggcgaggc ctggggcttc aatgaagctg  60
tcctgcaggg cttctggcta caccttcaca agctatggta taagctgggt gaagcagaga  120
actggacagg gccttgagtg gattggagag atttatccca gaagtggtgt tacttactac  180
aatgagaagt tcaagggtag ggccacactg actgcagaca atcctccag cacagcgttc  240
atggagctcc gcagcctgac atctgaggac tctcgggtct atttctgtgc aagagagtct  300
atatcactac gactaggctg gtacttcgat gtctggggca cagggaccac ggtcaccgtc  360
tcctca                                                                     366

SEQ ID NO: 29             moltype = AA  length = 107
FEATURE                   Location/Qualifiers
source                    1..107
                          mol_type = protein
                          organism = Mus musculus
SEQUENCE: 29
DIQMTQSPAS LSASVGDTVT ITCRASENIY RFLAWYQQKQ RKSPHLLVYN AKTLAEGVPS  60
RFSGSGSGTQ FSLKINSLQP EDFGSYYCQH HYGPPLTFGA GTKLELT               107

SEQ ID NO: 30             moltype = DNA  length = 321
FEATURE                   Location/Qualifiers
source                    1..321
                          mol_type = other DNA
                          organism = Mus musculus
CDS                       1..321
                          protein_id = 29
                          translation = DIQMTQSPASLSASVGDTVTITCRASENIYRFLAWYQQKQRKSPHL
                          LVYNAKTLAEGVPSRFSGSGSGTQFSLKINSLQPEDFGSYYCQHHYGPPLTFGAGTKLE
                          LT
SEQUENCE: 30
gacatccaga tgactcagtc tccagcctcc ctatctgcat ctgtgggaga tactgtcacc  60
atcacatgtc gagcaagtga gaatatttac aggtttttag catgtgatca gcagaaacag  120
agaaaatctc cgcacctcct ggtctataat gcaaaaacct tagcagaagg tgtgccatca  180
aggttcagtg gcagtggatc aggcacacag ttttctctga agatcaacag tctgcagcct  240
gaagattttg ggagttatta ttgtcaacat cattatggtc ctccactcac gttcggtgct  300
gggaccaagc tggagctgac a                                                    321

SEQ ID NO: 31             moltype = AA  length = 10
FEATURE                   Location/Qualifiers
source                    1..10
                          mol_type = protein
                          organism = Mus musculus
SEQUENCE: 31
GYTFTSYGIS                                                                  10

SEQ ID NO: 32             moltype = AA  length = 17
FEATURE                   Location/Qualifiers
```

-continued

```
source                1..17
                      mol_type = protein
                      organism = Mus musculus
SEQUENCE: 32
EIYPRSGNTY YNEKFKG                                                  17

SEQ ID NO: 33         moltype = AA  length = 15
FEATURE               Location/Qualifiers
source                1..15
                      mol_type = protein
                      organism = Mus musculus
SEQUENCE: 33
ARESILLRLG WYFDV                                                    15

SEQ ID NO: 34         moltype = AA  length = 11
FEATURE               Location/Qualifiers
source                1..11
                      mol_type = protein
                      organism = Mus musculus
SEQUENCE: 34
RASENIYRFL A                                                        11

SEQ ID NO: 35         moltype = AA  length = 7
FEATURE               Location/Qualifiers
source                1..7
                      mol_type = protein
                      organism = Mus musculus
SEQUENCE: 35
NAKTLAE                                                             7

SEQ ID NO: 36         moltype = AA  length = 9
FEATURE               Location/Qualifiers
source                1..9
                      mol_type = protein
                      organism = Mus musculus
SEQUENCE: 36
QHHYGPPLT                                                           9

SEQ ID NO: 37         moltype = AA  length = 122
FEATURE               Location/Qualifiers
source                1..122
                      mol_type = protein
                      organism = Mus musculus
SEQUENCE: 37
QVQLQQSGAE LARPGASVKL SCKASGYTFT SYGISWVKQR TGQGLEWIGE IYPRSGNTYY   60
NEKFKGRATL TADKSSSTAY MELRSLTSED SAVYFCARES ILLRLGWYFD VWGTGTTVTV   120
SS                                                                  122

SEQ ID NO: 38         moltype = DNA  length = 366
FEATURE               Location/Qualifiers
source                1..366
                      mol_type = other DNA
                      organism = Mus musculus
CDS                   1..366
                      protein_id = 37
                      translation = QVQLQQSGAELARPGASVKLSCKASGYTFTSYGISWVKQRTGQGLE
                      WIGEIYPRSGNTYYNEKFKGRATLTADKSSSTAYMELRSLTSEDSAVYFCARESILLRL
                      GWYFDVWGTGTTVTVSS
SEQUENCE: 38
caggttcagc tgcagcagtc tggagctgag ctggcgaggc ctggggcttc agtgaagctg   60
tcctgcaagg cttctggcta caccttcaca agctatggta taagctgggt gaagcagaga   120
actggacagg gccttgagtg gattggagag atttatccta gaagtggtaa tacttactac   180
aatgagaagt tcaagggcag ggccacactg actgcagaca atcctccag cacagcgtac   240
atggagctcc gcagcctgac atctgaggac tctgcggtct atttctgtgc aagagagtct   300
atattactac ggctaggctg gtacttcgat gtctggggca cagggaccac ggtcaccgtc   360
tcctca                                                              366

SEQ ID NO: 39         moltype = AA  length = 107
FEATURE               Location/Qualifiers
source                1..107
                      mol_type = protein
                      organism = Mus musculus
SEQUENCE: 39
DIQMTQSPAS LSASVGGTVT ITCRASENIY RFLAWYQQKQ GKSPQLLVYN AKTLAEGVPS   60
RFSGSGSGTQ FSLKINSLQP EDFGIYYCQH HYGPPLTFGA GTKLELK                 107

SEQ ID NO: 40         moltype = DNA  length = 321
FEATURE               Location/Qualifiers
source                1..321
```

```
                         mol_type = other DNA
                         organism = Mus musculus
CDS                      1..321
                         protein_id = 39
                         translation = DIQMTQSPASLSASVGGTVTITCRASENIYRFLAWYQQKQGKSPQL
                          LVYNAKTLAEGVPSRFSGSGSGTQFSLKINSLQPEDFGIYYCQHHYGPPLTFGAGTKLE
                          LK
SEQUENCE: 40
gacatccaga tgactcagtc tccagcctcc ctatctgcat ctgtgggagg aactgtcacc  60
atcacatgtc gagcaagtga gaatatttac aggtttttag catggtatca gcagaaacag  120
ggaaaatctc ctcagctcct ggtctataat gcaaaaacct tagcagaagg tgtgccatca  180
aggttcagtg gcagtggatc aggcacacag ttttctctga agatcaacag ccttcagcct  240
gaagattttg ggatttatta ctgtcaacat cattatggtc ctcctctcac gttcggtgct  300
gggaccaagc tggagctgaa a                                            321

SEQ ID NO: 41           moltype = AA  length = 10
FEATURE                 Location/Qualifiers
source                  1..10
                        mol_type = protein
                        organism = Mus musculus
SEQUENCE: 41
GYTFTSYGIS                                                          10

SEQ ID NO: 42           moltype = AA  length = 17
FEATURE                 Location/Qualifiers
source                  1..17
                        mol_type = protein
                        organism = Mus musculus
SEQUENCE: 42
EIYPRSGNTY YNEKVKG                                                  17

SEQ ID NO: 43           moltype = AA  length = 15
FEATURE                 Location/Qualifiers
source                  1..15
                        mol_type = protein
                        organism = Mus musculus
SEQUENCE: 43
ARESIFLRLG WYFDV                                                    15

SEQ ID NO: 44           moltype = AA  length = 11
FEATURE                 Location/Qualifiers
source                  1..11
                        mol_type = protein
                        organism = Mus musculus
SEQUENCE: 44
RASDNIYRFL A                                                        11

SEQ ID NO: 45           moltype = AA  length = 7
FEATURE                 Location/Qualifiers
source                  1..7
                        mol_type = protein
                        organism = Mus musculus
SEQUENCE: 45
NAKTLAE                                                             7

SEQ ID NO: 46           moltype = AA  length = 9
FEATURE                 Location/Qualifiers
source                  1..9
                        mol_type = protein
                        organism = Mus musculus
SEQUENCE: 46
QHHYGPPLT                                                           9

SEQ ID NO: 47           moltype = AA  length = 122
FEATURE                 Location/Qualifiers
source                  1..122
                        mol_type = protein
                        organism = Mus musculus
SEQUENCE: 47
QVQLQQSGAE LARPGASVKL SCKASGYTFT SYGISWVKQR TGQGLEWIGE IYPRSGNTYY  60
NEKVKGKATL TADKSSSTAY MELRSLTSED SAVYFCARES IFLRLGWYFD VWGTGTTVTV  120
SS                                                                  122

SEQ ID NO: 48           moltype = DNA  length = 366
FEATURE                 Location/Qualifiers
source                  1..366
                        mol_type = other DNA
                        organism = Mus musculus
CDS                     1..366
```

-continued

```
                         protein_id = 47
                         translation = QVQLQQSGAELARPGASVKLSCKASGYTFTSYGISWVKQRTGQGLE
                         WIGEIYPRSGNTYYNEKVKGKATLTADKSSSTAYMELRSLTSEDSAVYFCARESIFLRL
                         GWYFDVWGTGTTVTVSS
SEQUENCE: 48
caggttcagc tgcagcagtc tggagctgag ctggcgaggc ctggggcttc agtgaagctg   60
tcctgcaagg cttctggcta caccttcaca agctatggta taagttgggt gaagcagaga  120
actggacagg gccttgagtg gattggagag atttatccta gaagtggtaa tacttactac  180
aatgagaagg tcaagggcaa ggccacactg actgcagaca atcctccag cacagcgtac  240
atggagctcc gcagcctgac atctgaggac tctgcggtct atttctgtgc aagagagtct  300
atattcctac gtctaggctg gtacttcgat gtctggggca cagggaccac ggtcaccgtc  360
tcctca                                                              366

SEQ ID NO: 49             moltype = AA  length = 107
FEATURE                   Location/Qualifiers
source                    1..107
                          mol_type = protein
                          organism = Mus musculus
SEQUENCE: 49
DIQMTQSPAS LSASVGETVT ITCRASDNIY RFLAWYQQKQ GKSPQLLVYN AKTLAEGVPS   60
RFSGSGTGTQ FSLKINSLQP EDFGIYYCQH HYGPPLTFGA GTKLELK                 107

SEQ ID NO: 50             moltype = DNA  length = 321
FEATURE                   Location/Qualifiers
source                    1..321
                          mol_type = other DNA
                          organism = Mus musculus
CDS                       1..321
                          protein_id = 49
                          translation = DIQMTQSPASLSASVGETVTITCRASDNIYRFLAWYQQKQGKSPQL
                           LVYNAKTLAEGVPSRFSGSGTGTQFSLKINSLQPEDFGIYYCQHHYGPPLTFGAGTKLE
                           LK
SEQUENCE: 50
gacatccaga tgactcagtc tccagcctcc ctatctgcat ctgtgggaga aactgtcacc   60
atcacatgtc gagcaagtga caatatttac aggtttttag catggtatca gcagaaacag  120
ggaaaatctc ctcagctcct ggtctataat gcaaaaacct tagcagaagg tgtgccatca  180
aggttcagtg gcagtggaac aggcacacag ttttctctga agatcaacag tcttcagcct  240
gaagattttg ggatttatta ctgtcaacat cattatggtc ctcctctcac gttcggtgct  300
gggaccaagc tggagctgaa a                                             321

SEQ ID NO: 51             moltype = AA  length = 10
FEATURE                   Location/Qualifiers
source                    1..10
                          mol_type = protein
                          organism = Mus musculus
SEQUENCE: 51
GYTFTSFGVN                                                          10

SEQ ID NO: 52             moltype = AA  length = 17
FEATURE                   Location/Qualifiers
source                    1..17
                          mol_type = protein
                          organism = Mus musculus
SEQUENCE: 52
QIYPRTGTTY HNERFKG                                                   17

SEQ ID NO: 53             moltype = AA  length = 11
FEATURE                   Location/Qualifiers
source                    1..11
                          mol_type = protein
                          organism = Mus musculus
SEQUENCE: 53
AREGDRYSLA Y                                                        11

SEQ ID NO: 54             moltype = AA  length = 11
FEATURE                   Location/Qualifiers
source                    1..11
                          mol_type = protein
                          organism = Mus musculus
SEQUENCE: 54
RASENIYRFL A                                                        11

SEQ ID NO: 55             moltype = AA  length = 7
FEATURE                   Location/Qualifiers
source                    1..7
                          mol_type = protein
                          organism = Mus musculus
SEQUENCE: 55
NAKTLVE                                                              7
```

-continued

```
SEQ ID NO: 56          moltype = AA  length = 9
FEATURE                Location/Qualifiers
source                 1..9
                       mol_type = protein
                       organism = Mus musculus
SEQUENCE: 56
QHHYGIPLT                                                              9

SEQ ID NO: 57          moltype = AA  length = 118
FEATURE                Location/Qualifiers
source                 1..118
                       mol_type = protein
                       organism = Mus musculus
SEQUENCE: 57
QVQVQQSGAE LARPGASVRL SCKASGYTFT SFGVNWVKQR TGQGLEWIGQ IYPRTGTTYH  60
NERFKGKATL TTDKSSSTAY MELRSLTSED SAVYFCAREG DRYSLAYWGQ GTLVTVSA    118

SEQ ID NO: 58          moltype = DNA  length = 354
FEATURE                Location/Qualifiers
source                 1..354
                       mol_type = other DNA
                       organism = Mus musculus
CDS                    1..354
                       protein_id = 57
                       translation = QVQVQQSGAELARPGASVRLSCKASGYTFTSFGVNWVKQRTGQGLE
                        WIGQIYPRTGTTYHNERFKGKATLTTDKSSSTAYMELRSLTSEDSAVYFCAREGDRYSL
                        AYWGQGTLVTVSA
SEQUENCE: 58
caggttcagg tacagcagtc cggagctgag ctggcgaggc ctggggcatc agtgaggctg  60
tcctgcaagg cttctggcta caccttcaca agctttggtg taaactgggt gaagcgagaga 120
actggacagg gccttgagtg gattggacag atttatccta gaactggtac tacttaccac  180
aatgagaggt tcaagggcaa ggccacactg actacagaca atcctccag cacagcgtac  240
atggagctcc gcagcctgac atctgaggac tctgcggtct atttctgtgc acgagaggga  300
gataggtact cacttgctta ctggggccaa gggactctgg tcactgtctc tgca        354

SEQ ID NO: 59          moltype = AA  length = 107
FEATURE                Location/Qualifiers
source                 1..107
                       mol_type = protein
                       organism = Mus musculus
SEQUENCE: 59
DIQMTQSPAS LSASVGETVT ITCRASENIY RFLAWYQQKQ GKSPQLLVYN AKTLVEGVPS  60
RFSGSGSGTQ FSLKINNLQP EDFGSYYCQH HYGIPLTFGA GTKLELK              107

SEQ ID NO: 60          moltype = DNA  length = 321
FEATURE                Location/Qualifiers
source                 1..321
                       mol_type = other DNA
                       organism = Mus musculus
CDS                    1..321
                       protein_id = 59
                       translation = DIQMTQSPASLSASVGETVTITCRASENIYRFLAWYQQKQGKSPQL
                        LVYNAKTLVEGVPSRFSGSGSGTQFSLKINNLQPEDFGSYYCQHHYGIPLTFGAGTKLE
                        LK
SEQUENCE: 60
gacatccaga tgactcagtc tccagcctcc ctatctgcat ctgtgggaga aactgtcacc  60
atcacatgtc gagcaagtga gaatatttac aggtttttag catggtatca gcagaaacag  120
ggaaaatctc ctcagctcct ggtctataat gcaaaaacct tagtagaagg tgtgccatca  180
aggttcagtg gcagtggatc aggcacacag ttttctctga agatcaacaa cctacagcct  240
gaagattttg ggagttatta ctgtcaacat cattatggta ttccgctcac gttcggtgct  300
gggaccaagc tggagctgaa a                                            321

SEQ ID NO: 61          moltype = AA  length = 10
FEATURE                Location/Qualifiers
source                 1..10
                       mol_type = protein
                       organism = Mus musculus
SEQUENCE: 61
GYTFASFGIS                                                            10

SEQ ID NO: 62          moltype = AA  length = 17
FEATURE                Location/Qualifiers
source                 1..17
                       mol_type = protein
                       organism = Mus musculus
SEQUENCE: 62
EIYPRSGTTY FNEKFRG                                                    17
```

```
SEQ ID NO: 63              moltype = AA   length = 12
FEATURE                    Location/Qualifiers
source                     1..12
                           mol_type = protein
                           organism = Mus musculus
SEQUENCE: 63
AREGVRRYAM DY                                                              12

SEQ ID NO: 64              moltype = AA   length = 11
FEATURE                    Location/Qualifiers
source                     1..11
                           mol_type = protein
                           organism = Mus musculus
SEQUENCE: 64
RASGNIYSFL A                                                               11

SEQ ID NO: 65              moltype = AA   length = 7
FEATURE                    Location/Qualifiers
source                     1..7
                           mol_type = protein
                           organism = Mus musculus
SEQUENCE: 65
NAKTLAE                                                                    7

SEQ ID NO: 66              moltype = AA   length = 9
FEATURE                    Location/Qualifiers
source                     1..9
                           mol_type = protein
                           organism = Mus musculus
SEQUENCE: 66
QHHYGIPLT                                                                  9

SEQ ID NO: 67              moltype = AA   length = 119
FEATURE                    Location/Qualifiers
source                     1..119
                           mol_type = protein
                           organism = Mus musculus
SEQUENCE: 67
QLHLQQSGAE LARPGASVRL SCKASGYTFA SFGISWVKQR TGQGLEYIGE IYPRSGTTYF  60
NEKFRGKATL SADKSSSTAY MELRSLTSED SAVYFCAREG VRRYAMDYWG QGTSVTVSS   119

SEQ ID NO: 68              moltype = DNA   length = 357
FEATURE                    Location/Qualifiers
source                     1..357
                           mol_type = other DNA
                           organism = Mus musculus
CDS                        1..357
                           protein_id = 67
                           translation = QLHLQQSGAELARPGASVRLSCKASGYTFASFGISWVKQRTGQGLE
                           YIGEIYPRSGTTYFNEKFRGKATLSADKSSSTAYMELRSLTSEDSAVYFCAREGVRRYA
                           MDYWGQGTSVTVSS
SEQUENCE: 68
cagcttcacc tgcagcagtc tggagctgag ctggcgaggc ctggggcttc agtgaggctg  60
tcctgcaagg cttctggcta caccttcgca agttttggta taagctgggt gaagcagaga  120
actggacagg gccttgaata cattggagag atttatccta gaagtggtac tacttacttc  180
aatgagaagt tcaggggcaa ggccacactg agtgcagaca aatcatccag cacagcgtac  240
atggagctcc gcagcctgac atctgaggac tctgcggtct atttctgtgc aagagaggga  300
gtacgacggt atgctatgga ctactggggt caaggaacct cagtcaccgt ctcctca     357

SEQ ID NO: 69              moltype = AA   length = 107
FEATURE                    Location/Qualifiers
source                     1..107
                           mol_type = protein
                           organism = Mus musculus
SEQUENCE: 69
DIQVTQSPAS LSASVGETVT ITCRASGNIY SFLAWYQQKQ GKSPQLLVYN AKTLAEGVPS  60
RFSGSGSGTQ FSLKISSLQP EDFGSYYCQH HYGIPLTFGA GTKLDLK                 107

SEQ ID NO: 70              moltype = DNA   length = 321
FEATURE                    Location/Qualifiers
source                     1..321
                           mol_type = other DNA
                           organism = Mus musculus
CDS                        1..321
                           protein_id = 69
                           translation = DIQVTQSPASLSASVGETVTITCRASGNIYSFLAWYQQKQGKSPQL
                           LVYNAKTLAEGVPSRFSGSGSGTQFSLKISSLQPEDFGSYYCQHHYGIPLTFGAGTKLD
                           LK
SEQUENCE: 70
```

```
gacatccagg tgactcagtc tccagcctcc ctatctgcgt ctgtgggaga aactgtcacc    60
atcacatgtc gcgcaagtgg gaatatttac agttttttag catggtatca gcagaaacag   120
ggaaaatctc ctcaactcct ggtctataat gcaaaaactt tagcagaagg tgtgccatca   180
aggttcagtg gcagtggatc aggcacacag ttttctctga agatcagcag cctgcagcct   240
gaagattttg ggagttatta ctgtcaacat cattatggta ttcctctcac gttcggtgct   300
gggaccaagt tggacctgaa a                                              321
```

```
SEQ ID NO: 71            moltype = AA   length = 10
FEATURE                  Location/Qualifiers
source                   1..10
                         mol_type = protein
                         organism = Mus musculus
SEQUENCE: 71
GYTFASFGIS                                                            10

SEQ ID NO: 72            moltype = AA   length = 17
FEATURE                  Location/Qualifiers
source                   1..17
                         mol_type = protein
                         organism = Mus musculus
SEQUENCE: 72
EIYPRSGTTY FNEKFRG                                                    17

SEQ ID NO: 73            moltype = AA   length = 12
FEATURE                  Location/Qualifiers
source                   1..12
                         mol_type = protein
                         organism = Mus musculus
SEQUENCE: 73
AREGVRRYAM DY                                                         12

SEQ ID NO: 74            moltype = AA   length = 11
FEATURE                  Location/Qualifiers
source                   1..11
                         mol_type = protein
                         organism = Mus musculus
SEQUENCE: 74
RASGNIYSFL A                                                          11

SEQ ID NO: 75            moltype = AA   length = 7
FEATURE                  Location/Qualifiers
source                   1..7
                         mol_type = protein
                         organism = Mus musculus
SEQUENCE: 75
NAKTLAE                                                                7

SEQ ID NO: 76            moltype = AA   length = 9
FEATURE                  Location/Qualifiers
source                   1..9
                         mol_type = protein
                         organism = Mus musculus
SEQUENCE: 76
QHHYGIPLT                                                              9

SEQ ID NO: 77            moltype = AA   length = 119
FEATURE                  Location/Qualifiers
source                   1..119
                         mol_type = protein
                         organism = Mus musculus
SEQUENCE: 77
QFQLQQSGAE LARPGASVKL SCKASGYTFA SFGISWVKQR TGQGLEYIGE IYPRSGTTYF     60
NEKFRGKATL TADKSSSTAY MELRSLTSED SAVYFCAREG VRRYAMDYWG QGTSVTVSS     119

SEQ ID NO: 78            moltype = DNA   length = 357
FEATURE                  Location/Qualifiers
source                   1..357
                         mol_type = other DNA
                         organism = Mus musculus
CDS                      1..357
                         protein_id = 77
                         translation = QFQLQQSGAELARPGASVKLSCKASGYTFASFGISWVKQRTGQGLE
                          YIGEIYPRSGTTYFNEKFRGKATLTADKSSSTAYMELRSLTSEDSAVYFCAREGVRRYA
                          MDYWGQGTSVTVSS
SEQUENCE: 78
cagtttcagc tgcagcagtc tggagctgag ctggcgaggc ctggggcttc agtgaagctg    60
tcctgcaagg cttctggcta caccttcgca agctttggta taagctgggt gaaacagaga   120
actgacagg gccttgaata cattggagag atttatccta gaagtggtac tacttacttc     180
aatgagaaat tcaggggcaa ggccacactg actgcagaca aatcatccag cacagcgtac   240
```

-continued

```
atggagctcc gcagcctgac atctgaggac tctgcggtct atttctgtgc aagagagggg    300
gtacgacggt atgctatgga ctactggggt caaggaacct cagtcaccgt ctcctca       357

SEQ ID NO: 79            moltype = AA  length = 107
FEATURE                  Location/Qualifiers
source                   1..107
                         mol_type = protein
                         organism = Mus musculus
SEQUENCE: 79
DIQVTQSPAS LSASVGETVT ITCRASGNIY SFLAWYQQKQ GKSPQLLVYN AKTLAEGVPS    60
RFSGSGSGTQ FSLKISSLQP EDFGSYYCQH HYGIPLTFGG GTKLDLK                   107

SEQ ID NO: 80            moltype = DNA  length = 321
FEATURE                  Location/Qualifiers
source                   1..321
                         mol_type = other DNA
                         organism = Mus musculus
CDS                      1..321
                         protein_id = 79
                         translation = DIQVTQSPASLSASVGETVTITCRASGNIYSFLAWYQQKQGKSPQL
                         LVYNAKTLAEGVPSRFSGSGSGTQFSLKISSLQPEDFGSYYCQHHYGIPLTFGGGTKLD
                         LK
SEQUENCE: 80
gacatccagg tgactcagtc tccagcctcc ctatctgcgt ctgtgggaga aactgtcacc    60
atcacatgtc gcgcaagtgg gaatatttac agttttttag catggtatca gcagaaacag    120
ggaaaatctc ctcagctcct ggtctataat gcaaaaacct agcagaagg tgtgccatca     180
aggttcagtg gcagtggatc aggcacacag ttttctctga agattagcag cctgcagcct    240
gaagattttg ggagttatta ctgtcaacat cattatggta ttcctctcac gttcggtggt    300
gggaccaagt tggacctgaa a                                              321

SEQ ID NO: 81            moltype = AA  length = 10
FEATURE                  Location/Qualifiers
source                   1..10
                         mol_type = protein
                         organism = Mus musculus
SEQUENCE: 81
GYTFASFGIS                                                           10

SEQ ID NO: 82            moltype = AA  length = 17
FEATURE                  Location/Qualifiers
source                   1..17
                         mol_type = protein
                         organism = Mus musculus
SEQUENCE: 82
EIYPRSGTTY FNEKFRG                                                   17

SEQ ID NO: 83            moltype = AA  length = 12
FEATURE                  Location/Qualifiers
source                   1..12
                         mol_type = protein
                         organism = Mus musculus
SEQUENCE: 83
AREGVRRYAM DY                                                        12

SEQ ID NO: 84            moltype = AA  length = 11
FEATURE                  Location/Qualifiers
source                   1..11
                         mol_type = protein
                         organism = Mus musculus
SEQUENCE: 84
RASGNIYSFL A                                                         11

SEQ ID NO: 85            moltype = AA  length = 7
FEATURE                  Location/Qualifiers
source                   1..7
                         mol_type = protein
                         organism = Mus musculus
SEQUENCE: 85
NAKTLAE                                                              7

SEQ ID NO: 86            moltype = AA  length = 9
FEATURE                  Location/Qualifiers
source                   1..9
                         mol_type = protein
                         organism = Mus musculus
SEQUENCE: 86
QHHYGIPLT                                                            9

SEQ ID NO: 87            moltype = AA  length = 119
```

```
FEATURE                     Location/Qualifiers
source                      1..119
                            mol_type = protein
                            organism = Mus musculus
SEQUENCE: 87
QLQLQQSGAE LARPGASVKL SCKASGYTFA SFGISWVKQR AGQGLEYIGE IYPRSGTTYF  60
NEKFRGKATL TADKSSSTAY MELRRLTSED SAVYFCAREG VRRYAMDYWG QGTSVTVSS   119

SEQ ID NO: 88               moltype = DNA   length = 357
FEATURE                     Location/Qualifiers
source                      1..357
                            mol_type = other DNA
                            organism = Mus musculus
CDS                         1..357
                            protein_id = 87
                            translation = QLQLQQSGAELARPGASVKLSCKASGYTFASFGISWVKQRAGQGLE
                            YIGEIYPRSGTTYFNEKFRGKATLTADKSSSTAYMELRRLTSEDSAVYFCAREGVRRYA
                            MDYWGQGTSVTVSS
SEQUENCE: 88
cagcttcagc tgcagcagtc tggagctgag ctggcgaggc ctggggcttc agtgaagctg  60
tcctgcaagg cttctggcta caccttcgca agttttggta taagttgggt gaagcagaga  120
gctggacagg gccttgagta cattggagag atttatccta gaagtggtac tacttacttc  180
aatgagaagt tcaggggcaa ggccacactg actgcagaca aatcatccag cacagcgtac  240
atggagctcc gcagactgac atctgaggac tctgcggtct atttctgtgc aagagagggg  300
gtacgacggt atgctatgga ctactggggt caaggaacct cagtcaccgt ctcctca     357

SEQ ID NO: 89               moltype = AA   length = 107
FEATURE                     Location/Qualifiers
source                      1..107
                            mol_type = protein
                            organism = Mus musculus
SEQUENCE: 89
DIQVTQSPAS LSASVGETVT ITCRASGNIY SFLAWYQQKQ GKSPQLLVYN AKTLAEGVPS  60
RFSGSGSGTQ FSLKINSLQP EDFGSYYCQH HYGIPLTFGA GTKLDLK               107

SEQ ID NO: 90               moltype = DNA   length = 321
FEATURE                     Location/Qualifiers
source                      1..321
                            mol_type = other DNA
                            organism = Mus musculus
CDS                         1..321
                            protein_id = 89
                            translation = DIQVTQSPASLSASVGETVTITCRASGNIYSFLAWYQQKQGKSPQL
                            LVYNAKTLAEGVPSRFSGSGSGTQFSLKINSLQPEDFGSYYCQHHYGIPLTFGAGTKLD
                            LK
SEQUENCE: 90
gacatccagg tgactcagtc tccagcctcc ctatctgcgt ctgtgggaga aactgtcacc  60
atcacatgtc gcgcaagtgg gaatatttac agttttttag catggtatca gcagaaacag  120
ggaaaatctc ctcagctcct ggtctataat gcaaaaacct tagcagaagg tgtgccatca  180
aggttcagtg gcagtggatc aggcacacag ttttctctga agatcaacag cctgcagcct  240
gaagattttg ggagttatta ctgtcaacat cattatggta ttcctctcac gttcggtgct  300
gggaccaagt tggacctgaa a                                            321

SEQ ID NO: 91               moltype = AA   length = 10
FEATURE                     Location/Qualifiers
source                      1..10
                            mol_type = protein
                            organism = Mus musculus
SEQUENCE: 91
GYTFTSFGVN                                                          10

SEQ ID NO: 92               moltype = AA   length = 17
FEATURE                     Location/Qualifiers
source                      1..17
                            mol_type = protein
                            organism = Mus musculus
SEQUENCE: 92
QIYPRTGTTY HNERFKG                                                  17

SEQ ID NO: 93               moltype = AA   length = 11
FEATURE                     Location/Qualifiers
source                      1..11
                            mol_type = protein
                            organism = Mus musculus
SEQUENCE: 93
AREGDRYSLA Y                                                        11

SEQ ID NO: 94               moltype = AA   length = 11
FEATURE                     Location/Qualifiers
```

```
source                  1..11
                        mol_type = protein
                        organism = Mus musculus
SEQUENCE: 94
RASENIYRFL A                                                            11

SEQ ID NO: 95           moltype = AA   length = 7
FEATURE                 Location/Qualifiers
source                  1..7
                        mol_type = protein
                        organism = Mus musculus
SEQUENCE: 95
NAKTLVE                                                                 7

SEQ ID NO: 96           moltype = AA   length = 9
FEATURE                 Location/Qualifiers
source                  1..9
                        mol_type = protein
                        organism = Mus musculus
SEQUENCE: 96
QHHYGIPLT                                                               9

SEQ ID NO: 97           moltype = AA   length = 118
FEATURE                 Location/Qualifiers
source                  1..118
                        mol_type = protein
                        organism = Mus musculus
SEQUENCE: 97
QVQVQQSGAE LARPGASVRL SCKASGYTFT SFGVNWVKQR TGQGLEWIGQ IYPRTGTTYH   60
NERFKGKATL TADKSSSTAY MELRSLTSED SAVYFCAREG DRYSLAYWGQ GTLVTVSA    118

SEQ ID NO: 98           moltype = DNA   length = 354
FEATURE                 Location/Qualifiers
source                  1..354
                        mol_type = other DNA
                        organism = Mus musculus
CDS                     1..354
                        protein_id = 97
                        translation = QVQVQQSGAELARPGASVRLSCKASGYTFTSFGVNWVKQRTGQGLE
                        WIGQIYPRTGTTYHNERFKGKATLTADKSSSTAYMELRSLTSEDSAVYFCAREGDRYSL
                        AYWGQGTLVTVSA
SEQUENCE: 98
caggttcagg tacagcagtc cggagctgag ctggcgaggc ctggggcatc agtgaggctg   60
tcctgcaagg cttctggcta caccttcaca agtttttggtg taaactgggt gaagcagaga  120
actggacagg gccttgagtg gattggacag atttatccta gaactggtac tacttaccac  180
aatgagaggt tcaagggcaa ggccacactg actgcagaca gtcctccag cacagcgtac   240
atggagctcc gcagcctgac atctgaggac tctgcggtct atttctgtgc acgaggggga  300
gataggtact cacttgctta ctggggccaa gggactctgg tcactgtctc tgca        354

SEQ ID NO: 99           moltype = AA   length = 107
FEATURE                 Location/Qualifiers
source                  1..107
                        mol_type = protein
                        organism = Mus musculus
SEQUENCE: 99
DIQMTQSPAS LSASVGETVT ITCRASENIY RFLAWYQQKQ GKSPQLLVYN AKTLVEGVPS   60
RFSGSGSGTQ FSLKINNLQP EDFGSYYCQH HYGIPLTFGA GTKLELK              107

SEQ ID NO: 100          moltype = DNA   length = 321
FEATURE                 Location/Qualifiers
source                  1..321
                        mol_type = other DNA
                        organism = Mus musculus
CDS                     1..321
                        protein_id = 99
                        translation = DIQMTQSPASLSASVGETVTITCRASENIYRFLAWYQQKQGKSPQL
                        LVYNAKTLVEGVPSRFSGSGSGTQFSLKINNLQPEDFGSYYCQHHYGIPLTFGAGTKLE
                        LK
SEQUENCE: 100
gacatccaga tgactcagtc tccagcctcc ctatctgcat ctgtgggaga aactgtcacc   60
atcacatgtc gagcaagtga gaatatttac aggttttttag catggtatca gcagaaacag  120
ggaaaatctc ctcagctcct ggtctataat gcaaaaacct tagtagaagg tgtgccatca  180
aggttcagtg gcagtggatc aggcacacag ttttctctga agatcaacaa cctacagcct  240
gaagatttttg gagttatta ctgtcaacat cattatggta ttccgctcac gttcggtgct  300
gggaccaagc tggagctgaa a                                           321

SEQ ID NO: 101          moltype = AA   length = 10
FEATURE                 Location/Qualifiers
source                  1..10
```

```
                              mol_type = protein
                              organism = Mus musculus
SEQUENCE: 101
GYTFTSFGVN                                                            10

SEQ ID NO: 102          moltype = AA   length = 17
FEATURE                 Location/Qualifiers
source                  1..17
                        mol_type = protein
                        organism = Mus musculus
SEQUENCE: 102
QIYPRSGTTY HNERFKG                                                    17

SEQ ID NO: 103          moltype = AA   length = 11
FEATURE                 Location/Qualifiers
source                  1..11
                        mol_type = protein
                        organism = Mus musculus
SEQUENCE: 103
AREGDRYSLA Y                                                          11

SEQ ID NO: 104          moltype = AA   length = 11
FEATURE                 Location/Qualifiers
source                  1..11
                        mol_type = protein
                        organism = Mus musculus
SEQUENCE: 104
RASENIYRFL A                                                          11

SEQ ID NO: 105          moltype = AA   length = 7
FEATURE                 Location/Qualifiers
source                  1..7
                        mol_type = protein
                        organism = Mus musculus
SEQUENCE: 105
NAKTLAE                                                               7

SEQ ID NO: 106          moltype = AA   length = 9
FEATURE                 Location/Qualifiers
source                  1..9
                        mol_type = protein
                        organism = Mus musculus
SEQUENCE: 106
QHHYGIPLT                                                             9

SEQ ID NO: 107          moltype = AA   length = 118
FEATURE                 Location/Qualifiers
source                  1..118
                        mol_type = protein
                        organism = Mus musculus
SEQUENCE: 107
QVQVHQSGAE LARPGASVRL SCKASGYTFT SFGVNWVKQR TGQGLEWIGQ IYPRSGTTYH  60
NERFKGKATL TADKSSSTAY MELRSLTSED SAVYFCAREG DRYSLAYWGQ GTLVTVSA    118

SEQ ID NO: 108          moltype = DNA   length = 354
FEATURE                 Location/Qualifiers
source                  1..354
                        mol_type = other DNA
                        organism = Mus musculus
CDS                     1..354
                        protein_id = 107
                        translation = QVQVHQSGAELARPGASVRLSCKASGYTFTSFGVNWVKQRTGQGLE
                        WIGQIYPRSGTTYHNERFKGKATLTADKSSSTAYMELRSLTSEDSAVYFCAREGDRYSL
                        AYWGQGTLVTVSA
SEQUENCE: 108
caggttcagg tacaccagtc cggagctgag ctggcgaggc ctggggcatc agtgaggctg  60
tcctgcaagg cttctggcta caccttcacg agctttggtg taaactgggt gaagcagaga  120
actggacagg gccttgagtg gattggacag atttatccta gaagtggtac tacttaccac  180
aatgagaggt tcaagggcaa ggccacactg actgcagaca aatcctccag cacagcgtac  240
atggagctcc gcagcctgac atctgaggac tctgcggtct atttctgtgc aagagaggga  300
gataggtact cacttgctta ctggggccaa gggactctgg tcactgtctc tgca         354

SEQ ID NO: 109          moltype = AA   length = 107
FEATURE                 Location/Qualifiers
source                  1..107
                        mol_type = protein
                        organism = Mus musculus
SEQUENCE: 109
DIQMTQSPAS LSASVGETVT ITCRASENIY RFLAWYQQKQ GKSPQLLVSN AKTLAEGVPS  60
```

```
RFSGSGSGTQ FSLKINYLQP EDFGNYYCQH HYGIPLTFGA GTKLELK                        107

SEQ ID NO: 110            moltype = DNA   length = 321
FEATURE                   Location/Qualifiers
source                    1..321
                          mol_type = other DNA
                          organism = Mus musculus
CDS                       1..321
                          protein_id = 109
                          translation = DIQMTQSPASLSASVGETVTITCRASENIYRFLAWYQQKGKSPQL
                           LVSNAKTLAEGVPSRFSGSGSGTQFSLKINYLQPEDFGNYYCQHHYGIPLTFGAGTKLE
                           LK
SEQUENCE: 110
gacatccaga tgactcagtc tccagcctcc ctatctgcat ctgtgggaga aactgtcacc          60
atcacatgtc gagcaagtga gaatatttac aggtttttag catggtatca gcagaaacag         120
ggaaaatctc ctcagctcct ggtctctaat gcaaaaacct tagcagaagg tgtgccatca         180
aggttcagtg gcagtggatc aggcacacag ttttctctga agatcaacta cctacagcct         240
gaagattttg ggaattatta ctgtcaacat cattatggta ttccgctcac gttcggtgct         300
gggaccaagc tggagctgaa a                                                    321

SEQ ID NO: 111            moltype = AA   length = 364
FEATURE                   Location/Qualifiers
source                    1..364
                          mol_type = protein
                          organism = Homo sapiens
SEQUENCE: 111
MAAISTSIPV ISQPQFTAMN EPQCFYNESI AFFYNRSGKH LATEWNTVSK LVMGLGITVC           60
IFIMLANLLV MVAIYVNRRF HFPIYYLMAN LAAADFFAGL AYFYLMFNTG PNTRRLTVST          120
WLLRQGLIDT SLTASVANLL AIAIERHITV FRMQLHTRMS NRRVVVVIVV IWTMAIVMGA          180
IPSVGWNCIC DIENCSNMAP LYSDSYLVFW AIFNLVTFVV MVVLYAHIFG YVRQRTMRMS          240
RHSSGPRRNR DTMMSLLKTV VIVLGAFIIC WTPGLVLLLL DVCCPQCDVL AYEKFFLLLA          300
EFNSAMNPII YSYRDKEMSA TFRQILCCQR SENPTGPTEG SDRSASSLNH TILAGVHSND          360
HSVV                                                                       364

SEQ ID NO: 112            moltype = AA   length = 364
FEATURE                   Location/Qualifiers
source                    1..364
                          mol_type = protein
                          organism = Mus musculus
SEQUENCE: 112
MAAASTSSPV ISQPQFTAMN EQQCFYNESI AFFYNRSGKY LATEWNTVSK LVMGLGITVC           60
VFIMLANLLV MVAIYVNRRF HFPIYYLMAN LAAADFFAGL AYFYLMFNTG PNTRRLTVST          120
WLLRQGLIDT SLTASVANLL AIAIERHITV FRMQLHTRMS NRRVVVVIVV IWTMAIVMGA          180
IPSVGWNCIC DIDHCSNMAP LYSDSYLVFW AIFNLVTFVV MVVLYAHIFG YVRQRTMRMS          240
RHSSGPRRNR DTMMSLLKTV VIVLGAFIVC WTPGLVLLLL DVCCPQCDVL AYEKFFLLLA          300
EFNSAMNPII YSYRDKEMSA TFRQILCCQR NENPNGPTEG SDRSASSLNH TILAGVHSND          360
HSVV                                                                       364

SEQ ID NO: 113            moltype = DNA   length = 37
FEATURE                   Location/Qualifiers
source                    1..37
                          mol_type = other DNA
                          organism = synthetic construct
SEQUENCE: 113
gctagcgcta ccggactcag atcccccccc ccccdn                                     37

SEQ ID NO: 114            moltype = DNA   length = 23
FEATURE                   Location/Qualifiers
source                    1..23
                          mol_type = other DNA
                          organism = synthetic construct
SEQUENCE: 114
accytgcatt tgaactcctt gcc                                                   23

SEQ ID NO: 115            moltype = DNA   length = 25
FEATURE                   Location/Qualifiers
source                    1..25
                          mol_type = other DNA
                          organism = synthetic construct
SEQUENCE: 115
actgccatca atcttccact tgaca                                                 25

SEQ ID NO: 116            moltype = DNA   length = 44
FEATURE                   Location/Qualifiers
source                    1..44
                          mol_type = other DNA
                          organism = synthetic construct
SEQUENCE: 116
ggtttagtga accgtcagat ccgctagcgc taccggactc agat                           44
```

-continued

```
SEQ ID NO: 117            moltype = DNA   length = 23
FEATURE                   Location/Qualifiers
source                    1..23
                          mol_type = other DNA
                          organism = synthetic construct
SEQUENCE: 117
ctggacaggg atccagagtt cca                                         23

SEQ ID NO: 118            moltype = DNA   length = 25
FEATURE                   Location/Qualifiers
source                    1..25
                          mol_type = other DNA
                          organism = synthetic construct
SEQUENCE: 118
actgaggcac ctccagatgt taact                                       25

SEQ ID NO: 119            moltype = AA   length = 351
FEATURE                   Location/Qualifiers
source                    1..351
                          mol_type = protein
                          organism = Homo sapiens
SEQUENCE: 119
MVIMGQCYYN ETIGFFYNNS GKELSSHWRP KDVVVVALGL TVSVLVLLTN LLVIAAIASN   60
RRFHQPIYYL LGNLAAADLF AGVAYLFLMF HTGPRTARLS LEGWFLRQGL LDTSLTASVA   120
TLLAIAVERH RSVMAVQLHS RLPRGRVVML IVGVWVAALG LGLLPAHSWH CLCALDRCSR   180
MAPLLSRSYL AVWALSSLLV FLLMVAVYTR IFFYVRRRVQ RMAEHVSCHP RYRETTLSLV   240
KTVVIILGAF VVCWTPGQVV LLLDGLGCES CNVLAVEKYF LLLAEANSLV NAAVYSCRDA   300
EMRRTFRRLL CCACLRQSTR ESVHYTSSAQ GGASTRIMLP ENGHPLMDST L            351

SEQ ID NO: 120            moltype = AA   length = 348
FEATURE                   Location/Qualifiers
source                    1..348
                          mol_type = protein
                          organism = Mus musculus
SEQUENCE: 120
MGQCYYNETI GFFYNNSGKE LSLHWRPKDV VVVALGLTVS VLVLLTNLLV IAAIASNRRF   60
HQPIYYLLGN LAAADLFAGM AYLFLMFHTG PRTARLSIKG WFLRQGLLDT SLTASVATLL   120
AIAVERHRSV MAVQLHSRLP RGRVVTLIVG VWAAALGLGL LPAHFWHCLC DLDSCSRMVP   180
LFSRSYLAAW ALSSLLVFLL MVAVYTRIFF YVRRRVERMA EHVSCHPRYR ETTLSLVKTV   240
VIILGAFVVC WTPGQVVLLL DGLDCKSCNV LAVEKYFLLL AEANSLVNAV VYSCRDAEMR   300
RTFRRLLCCM CLRWSSHKSA RYSASAQTGA STRIMLPENG RPLMDSTL                348

SEQ ID NO: 121            moltype = AA   length = 353
FEATURE                   Location/Qualifiers
source                    1..353
                          mol_type = protein
                          organism = Homo sapiens
SEQUENCE: 121
MNECHYDKHM DFFYNRSNTD TVDDWTGTKL VIVLCVGTFF CLFIFFSNSL VIAAVIKNRK   60
FHFPFYYLLA NLAAADFFAG IAYVFLMFNT GPVSKTLTVN RWFLRQGLLD SSLTASLTNL   120
LVIAVERHMS IMRMRVHSNL TKKRVTLLIL LVWAIAIFMG AVPTLGWNCL CNISACSSLA   180
PIYSRSYLVF WTVSNLMAFL IMVVYLRIY VYVKRKTNVL SPHTSGSISR RRTPMKLMKT   240
VMTVLGAFVV CWTPGLVVLL LDGLNCRQCG VQHVKRWFLL LALLNSVVNP IIYSYKDEDM   300
YGTMKKMICC FSQENPERRP SRIPSTVLSR SDTGSQYIED SISQGAVCNK STS          353

SEQ ID NO: 122            moltype = AA   length = 354
FEATURE                   Location/Qualifiers
source                    1..354
                          mol_type = protein
                          organism = Mus musculus
SEQUENCE: 122
MNECHYDKRM DFFYNRSNTD TADEWTGTKL VIVLCVGTFF CLFIFFSNSL VIAAVITNRK   60
FHFPFYYLLA NLAAADFFAG IAYVFLMFNT GPVSKTLTVN RWFLRQGLLD TSLTASLANL   120
LVIAVERHMS IMRMRVHSNL TKKRVTLLIL LVWAIAIFMG AVPTLGWNCL CNISACSSLA   180
PIYSRSYLIF WTVSNLLAFF IMVAVYVRIY MYVKRKTNVL SPHTSGSISR RRAPMKLMKT   240
VMTVLGAFVV CWTPGLVVLL LDGLNCKQCN VQHVKRWFLL LALLNSVMNP IIYSYKDEDM   300
YNTMRKMICC ALQDSNTERR PSRNPSTIHS RSETGSQYLE DSISQGPVCN KNGS          354

SEQ ID NO: 123            moltype = AA   length = 122
FEATURE                   Location/Qualifiers
source                    1..122
                          mol_type = protein
                          organism = synthetic construct
SEQUENCE: 123
QVQLVQSGAE VKKPGASVKV SCKASGYTFT SYGISWVRQA PGQGLEWMGE IYPRSGNTYY   60
NEKFKGRVTL TADKSTSTAY MELRSLTSED TAVYFCARES ISRRLGWNFD VWGQGTTVTV   120
SS                                                                122
```

-continued

```
SEQ ID NO: 124            moltype = AA  length = 107
FEATURE                   Location/Qualifiers
source                    1..107
                          mol_type = protein
                          organism = synthetic construct
SEQUENCE: 124
DIQMTQSPSS LSASVGDTVT ITCRASENIY SFLAWYQQKP GKAPKLLIYN AKTLTEGVPS  60
RFSGSGSGTH FSLTINSLQP EDFGIYYCQH HYGPPLTFGQ GTKLEIK            107

SEQ ID NO: 125            moltype = AA  length = 122
FEATURE                   Location/Qualifiers
source                    1..122
                          mol_type = protein
                          organism = synthetic construct
SEQUENCE: 125
QVQLQESGPG LVKPSETLSL TCTASGYTFT SYGISWVRQT PGKGLEWIGE IYPRSGNTYY  60
NEKFKGRATL SADKSKNQAS LKLKSVTAAD TAIYFCARES ISRRLGWNFD VWGRGTLVTV 120
SG                                                            122

SEQ ID NO: 126            moltype = AA  length = 107
FEATURE                   Location/Qualifiers
source                    1..107
                          mol_type = protein
                          organism = synthetic construct
SEQUENCE: 126
DIQMTQTPSS LSASVGDRVT ITCRASENIY SFLAWYQQKP GEAPKRVVYN AKTLTEGVPS  60
RFSGSGSGTD FTLTISSLQP EDFATYYCQH HYGPPLTFGQ GTKLEIK            107

SEQ ID NO: 127            moltype = AA  length = 122
FEATURE                   Location/Qualifiers
source                    1..122
                          mol_type = protein
                          organism = synthetic construct
SEQUENCE: 127
QVQLVQSGAE VKKPGASVKV SCKASGYTFT SYGISWVRQA PGQGLEWIGE IYPRSGNTYY  60
NEKFKGRATL TADKSTSTAY MELRSLRSDD TAVYFCARES ISRRLGWNFD VWGTGTTVTV 120
SS                                                            122

SEQ ID NO: 128            moltype = AA  length = 107
FEATURE                   Location/Qualifiers
source                    1..107
                          mol_type = protein
                          organism = synthetic construct
SEQUENCE: 128
DIQMTQSPSS LSASVGDRVT ITCRASENIY SFLAWYQQKP GKAPKLVVYN AKTLTEGVPS  60
RFSGSGSGTD FTLTISSLQP EDFATYYCQH HYGPPLTFGA GTKLELK            107

SEQ ID NO: 129            moltype = AA  length = 330
FEATURE                   Location/Qualifiers
source                    1..330
                          mol_type = protein
                          organism = Homo sapiens
SEQUENCE: 129
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG 120
PSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPGK                              330

SEQ ID NO: 130            moltype = AA  length = 107
FEATURE                   Location/Qualifiers
source                    1..107
                          mol_type = protein
                          organism = Homo sapiens
SEQUENCE: 130
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC          107
```

ANTIBODY, NUCLEIC ACID, CELL, AND PHARMACEUTICAL

SEQUENCE LISTING

A sequence listing in electronic (XML file) format is filed with this application and incorporated herein by reference. The name of the XML file is "Sequence Listing-1893A.xml"; the file was created on Jan. 6, 2025; the size of the file is 139,601 bytes.

TECHNICAL FIELD

This disclosure relates to an antibody that specifically binds to an extracellular domain of human lysophosphatidic acid receptor 1 (human LPA1), a nucleic acid encoding the antibody, a cell including the nucleic acid, and a medicament including the antibody as an active ingredient.

BACKGROUND ART

Lysophosphatidic acid (LPA) is a lysophospholipid having a glycerol scaffold bonded with one phosphoric acid and one fatty acid. Initially, LPA was thought to be one of intermediate products of lipid metabolites, but it is now recognized as a physiologically active lipid mediator that exhibits a variety of physiological effects. For example, LPA is involved in cell functions such as cell proliferation, apoptosis suppression, cell migration, production of cytokines and chemokines, platelet aggregation, smooth muscle contraction, cell transformation, and neurite regression (Non-Patent Document 1, 2).

LPA binds to a G-protein coupled receptor on a cell surface to modulate the intracellular signaling pathway and exhibit various physiological effects. Six subtypes of LPA receptors, LPA1, LPA2, LPA3, LPA4, LPA5, and LPA6, have been reported (Non-Patent Document 3). Three receptors LPA1, LPA2, and LPA3 belong to Endothelial Differentiation Gene (EDG) family and also referred to as EDG2, EDG4, and EDG7 respectively, which structurally have high homology to each other. LPA4 to LPA6 belong to non-EDG family and have low homology to the EDG family members.

In studies on modulation of LPA receptor functions using cell models and animal models, developmental biological and pathophysiologic influences of the LPA receptor on organs such as nerve, cardiovascular, reproductive organ, lung, liver, and kidney have been investigated. The studies have suggested that LPA-dependent cell dysfunction may be causally involved in diseases including nerve and bone developmental disorder, such as fibrosis, cancer, neuropsychiatric disorder, pain, cardiovascular disease, bone disorder, infertility, and obesity (Non-Patent Documents 1, 2, 4, 5).

Tissue fibrosis is a disease that results from abnormal control of a tissue healing process, leading to tissue dysfunction due to excessive accumulation of extracellular matrix. It has been reported that a LPA concentration in an alveolar lavage fluid in bleomycin-induced fibrosis model mice is increased, and that fibrosis is suppressed in the same models by LPA1 knockout or LPA1 antagonist administration (Non-Patent Documents 6, 7). Also, it has been reported that LPA1 antagonists BMS-986020 and BMS-986278 improve respiratory function and lung fibrosis in patients with idiopathic pulmonary fibrosis (Non-Patent Documents 8, 9). Thus, control of abnormal LPA1-dependent cell functions is useful for treating diseases resulting from fibrosis (e.g., pulmonary fibrosis such as idiopathic pulmonary fibrosis, hepatic fibrosis such as nonalcoholic steatohepatitis, renal fibrosis such as diabetic nephropathy, skin fibrosis such as scleroderma, cardiovascular fibrosis, and gastrointestinal fibrosis) (Non-Patent Documents 1, 2, 10, 11).

Examples of other diseases that have been suggested to be effectively treated by controlling the LPA1-dependent cell functions include neuropathic and inflammatory pain such as fibromyalgia, cancer pain, and diabetic neuropathy (Non-Patent Documents 12 to 14); inflammatory and autoimmune diseases such as rheumatoid arthritis, sepsis, and Guillain-Barre syndrome (Non-Patent Documents 15 to 17); metabolic diseases such as obesity and insulin-resistant diabetes (Non-Patent Document 18); cardiovascular disorders such as atherosclerosis, stroke, and hypertensive nephropathy (Non-Patent Documents 19 to 21); nervous system disorders such as hydrocephalus, schizophrenia, depression, and dementia (Non-Patent Documents 22, 23); cell proliferation diseases (tumor cell proliferation, tumor infiltration and metastasis, and controlled angiogenesis) (Non-Patent Documents 6, 24, 25); urologic disorders such as prostatic hyperplasia and urinary incontinence (Non-Patent Documents 26, 27); and ophthalmological diseases such as ischemic retinopathy (Non-Patent Document 28). LPA1, LPA2, and LPA3 have different in vivo distributions depending on their subtypes, and each subtype contributes to different cell functions and physiological actions (Non-Patent Documents 1, 2). Thus, a substance that binds specifically to human LPA1 and not specifically to human LPA2 and human LPA3 is desired as a useful active ingredient in pharmaceuticals with low side effects. As reported for the LPA1 antagonist BMS-986020, there is a case where the pharmaceutical binds to multiple LPA receptors, leading to discontinuation of its development due to side effects. It is still not easy to find a substance that binds specifically to human LPA1 and not specifically to human LPA2 and human LPA3.

Although several LPA1 antagonists consisting of low-molecular-weight compounds have been invented, none of them has yet practically utilized (Non-Patent Document 6). Any antibody that binds specifically to LPA1 and not specifically to human LPA2 and LPA3 to control the LPA1-dependent cell functions is useful, but there has been no report on such an antibody.

PRIOR ART DOCUMENTS

Non-Patent Documents

Non-Patent Document 1: Aikawa S, Hashimoto T, Kano K, Aoki J. "Lysophosphatidic acid as a lipid mediator with multiple biological actions." J Biochem. 2015; 157:81-89

Non-Patent Document 2: Yung Y C, Stoddard N C, Chun J. "LPA receptor signaling: pharmacology, physiology, and pathophysiology." J Lipid Res. 2014; 55: 1192-1214

Non-Patent Document 3: Kihara Y, Maceyka M, Spiegel S, Chun J. "Lysophospholipid receptor nomenclature review: IUPHAR Review 8." Br J Pharmacol. 2014; 171: 3575-3594

Non-Patent Document 4: Kano K, Aoki J, Hla T. "Lysophospholipid Mediators in Health and Disease." Annu Rev Pathol. 2022; 17: 459-483

Non-Patent Document 5: Meduri B, Pujar G V, Durai Ananda Kumar T, Akshatha H S, Sethu A K, Singh M, Kanagarla A, Mathew B. "Lysophosphatidic acid (LPA) receptor modulators: Structural features and recent development." Eur J Med Chem. 2021; 222: 113574

Non-Patent Document 6: Tager A M, LaCamera P, Shea B S, Campanella G S, Selman M, Zhao Z, Polosukhin V, Wain

3

J, Karimi-Shah B A, Kim N D, Hart W K, Pardo A, Blackwell T S, Xu Y, Chun J, Luster A D. "The lysophosphatidic acid receptor LPA1 links pulmonary fibrosis to lung injury by mediating fibroblast recruitment and vascular leak." Nat Med. 2008; 14: 45-54

Non-Patent Document 7: Swaney J S, Chapman C, Correa L D, Stebbins K J, Bundey R A, Prodanovich P C, Fagan P, Baccei C S, Santini A M, Hutchinson J H, Seiders T J, Parr T A, Prasit P, Evans J F, Lorrain D S. "A novel, orally active LPA(1) receptor antagonist inhibits lung fibrosis in the mouse bleomycin model." Br J Pharmacol. 2010; 160: 1699-1713

Non-Patent Document 8: Palmer S M, Snyder L, Todd J L, Soule B, Christian R, Anstrom K, Luo Y, Gagnon R, Rosen G. "Randomized, Double-Blind, Placebo-Controlled, Phase 2 Trial of BMS-986020, a Lysophosphatidic Acid Receptor Antagonist for the Treatment of Idiopathic Pulmonary Fibrosis." Chest. 2018; 154: 1061-1069

Non-Patent Document 9: Cheng P T W, Kaltenbach R F 3rd, Zhang H, Shi J, Tao S, Li J, Kennedy L J, Walker S J, Shi Y, Wang Y, Dhanusu S, Reddigunta R, Kumaravel S, Jusuf S, Smith D, Krishnananthan S, Li J, Wang T, Heiry R, Sum C S, Kalinowski S S, Hung C P, Chu C H, Azzara A V, Ziegler M, Burns L, Zinker B A, Boehm S, Taylor J, Sapuppo J, Mosure K, Everlof G, Guarino V, Zhang L, Yang Y, Ruan Q, Xu C, Apedo A, Traeger S C, Cvijic M E, Lentz K A, Tirucherai G, Sivaraman L, Robl J, Ellsworth B A, Rosen G, Gordon D A, Soars M G, Gill M, Murphy B J. "Discovery of an Oxycyclohexyl Acid Lysophosphatidic Acid Receptor 1 (LPA1) Antagonist BMS-986278 for the Treatment of Pulmonary Fibrotic Diseases." J Med Chem. 2021; 64: 15549-15581

Non-Patent Document 10: Kim D, Li H Y, Lee J H, Oh Y S, Jun H S. "Lysophosphatidic acid increases mesangial cell proliferation in models of diabetic nephropathy via Racl/MAPK/KLF5 signaling." Exp Mol Med. 2019; 51: 1-10

Non-Patent Document 12: Ueda H. "LPA receptor signaling as a therapeutic target for radical treatment of neuropathic pain and fibromyalgia." Pain Manag. 2020; 10: 43-53

Non-Patent Document 13: Ueda H, Neyama H, Matsushita Y. "Lysophosphatidic Acid Receptor 1- and 3-Mediated Hyperalgesia and Hypoalgesia in Diabetic Neuropathic Pain Models in Mice." Cells. 2020; 9: 1906

Non-Patent Document 14: Srikanth M, Chew W S, Hind T, Lim S M, Hay N W J, Lee J H M, Rivera R, Chun J, Ong W Y, Herr D R. "Lysophosphatidic acid and its receptor LPA1 mediate carrageenan induced inflammatory pain in mice." Eur J Pharmacol. 2018; 841: 49-56

Non-Patent Document 15: Miyabe Y, Miyabe C, Iwai Y, Takayasu A, Fukuda S, Yokoyama W, Nagai J, Jona M, Tokuhara Y, Ohkawa R, Albers H M, Ovaa H, Aoki J, Chun J, Yatomi Y, Ueda H, Miyasaka M, Miyasaka N, Nanki T. "Necessity of lysophosphatidic acid receptor 1 for development of arthritis." Arthritis Rheum. 2013; 65: 2037-2047

Non-Patent Document 16: Zhao J, Wei J, Weathington N, Jacko A M, Huang H, Tsung A, Zhao Y. "Lysophosphatidic acid receptor 1 antagonist kil6425 blunts abdominal and systemic inflammation in a mouse model of peritoneal sepsis." Transl Res. 2015; 166: 80-88

Non-Patent Document 17: Szepanowski F, Winkelhausen M, Steubing R D, Mausberg A K, Kleinschnitz C, Stettner M. J "LPA1 signaling drives Schwann cell dedifferentiation in experimental autoimmune neuritis." Neuroinflammation. 2021; 18: 293

4

Non-Patent Document 18: D'Souza K, Paramel G V, Kienesberger P C. "Lysophosphatidic Acid Signaling in Obesity and Insulin Resistance." Nutrients. 2018; 10: 399

Non-Patent Document 19: Zhou Y, Little P J, Ta H T, Xu S, Kamato D. "Lysophosphatidic acid and its receptors: pharmacology and therapeutic potential in atherosclerosis and vascular disease." Pharmacol Ther. 2019; 204: 107404

Non-Patent Document 20: Gaire B P, Sapkota A, Choi J W. "BMS-986020, a Specific LPA1 Antagonist, Provides Neuroprotection against Ischemic Stroke in Mice." Antioxidants 2020; 9: 1097

Non-Patent Document 21: Naruse T, Otake H, Takahashi T. "Effects of a lysophosphatidic acid receptor 1 antagonist on hypertensive renal injury in Dahl-Iwai salt-sensitive rats." J Pharmacol Sci. 2022; 149:179-188

Non-Patent Document 22: Yung Y C, Mutoh T, Lin M E, Noguchi K, Rivera R R, Choi J W, Kingsbury M A, Chun J. "Lysophosphatidic acid signaling may initiate fetal hydrocephalus." Sci Transl Med. 2011; 3: 99ra87

Non-Patent Document 23: Moreno-Fernandez R D, Tabbai S, Castilla-Ortega E, Perez-Martin M, Estivill-Torrus G, Rodriguez de Fonseca F, Santin L J, Pedraza C. "Stress, Depression, Resilience and Ageing: A Role for the LPA-LPA1 Pathway." Curr Neuropharmacol. 2018; 16: 271-283

Non-Patent Document 24: Boucharaba A, Serre C M, Guglielmi J, Bordet J C, Clezardin P, Peyruchaud O. "The type 1 lysophosphatidic acid receptor is a target for therapy in bone metastases." Proc Natl Acad Sci USA. 2006; 103: 9643-9648

Non-Patent Document 25: Zhao P F, Wu S, Li Y, Bao G, Pei J Y, Wang Y W, Ma Q, Sun H J, Damirin A. "LPA receptorl antagonists as anticancer agents suppress human lung tumours." Eur J Pharmacol. 2020; 868: 172886

Non-Patent Document 26: Sakamoto K, Noguchi Y, Ueshima K, Yamakuni H, Ohtake A, Sato S, Ishizu K, Hosogai N, Kawaminami E, Takeda M, Masuda N. "Effect of ASP6432, a Novel Type 1 Lysophosphatidic Acid Receptor Antagonist, on Urethral Function and Prostate Cell Proliferation". J Pharmacol Exp Ther. 2018; 366: 390-396

Non-Patent Document 27: Sakamoto K, Noguchi Y, Ueshima K, Ohtake A, Sato S, Imazumi K, Takeda M, Masuda N. "Modulation of urinary frequency via type 1 lysophosphatidic acid receptors: Effect of the novel antagonist ASP6432 in conscious rats." Eur J Pharmacol. 2019; 853: 11-17

Non-Patent Document 28: Yang C, Lafleur J, Mwaikambo B R, Zhu T, Gagnon C, Chemtob S, Di Polo A, Hardy P. "The role of lysophosphatidic acid receptor (LPA1) in the oxygen-induced retinal ganglion cell degeneration." Invest Ophthalmol Vis Sci. 2009; 50: 1290-1298

DISCLOSURE OF INVENTION

Technical Problem

An object of the present disclosure is to provide a novel antibody that specifically binds to an extracellular domain of LPA1, and a relevant technology.

Solution to Problem

An aspect of the present disclosure is an antibody that specifically binds to an extracellular domain of human LPA1, wherein the antibody does not specifically bind to an extracellular domain of human LPA2, and the antibody does not specifically bind to an extracellular domain of human LPA3.

Preferably, the antibody includes an activity of blocking an LPA1-dependent cell function.

Preferably, the antibody includes:

a heavy chain CDR1 including an amino acid sequence represented by SEQ ID NO: 1, 11,21,31,41, 51, 61, 71, 81, 91, or 101;

a heavy chain CDR2 including an amino acid sequence represented by SEQ ID NO: 2, 12, 22, 32, 42, 52, 62, 72, 82, 92, or 102;

a heavy chain CDR3 including an amino acid sequence represented by SEQ ID NO: 3, 13, 23, 33, 43, 53, 63, 73, 83, 93, or 103;

a light chain CDR1 including an amino acid sequence represented by SEQ ID NO: 4, 14, 24, 34, 44, 54, 64, 74, 84, 94, or 104;

a light chain CDR2 including an amino acid sequence represented by SEQ ID NO: 5, 15, 25, 35, 45, 55, 65, 75, 85, 95, or 105; and a light chain CDR3 including an amino acid sequence represented by SEQ ID NO: 6, 16, 26, 36, 46, 56, 66, 76, 86, 96, or 106.

Preferably, the antibody satisfies any one of the following (A1) to (A11):

(A1) including a heavy chain CDR1 including an amino acid sequence represented by SEQ ID NO: 1, a heavy chain CDR2 including an amino acid sequence represented by SEQ ID NO: 2, and a heavy chain CDR3 including an amino acid sequence represented by SEQ ID NO: 3;

(A2) including a heavy chain CDR1 including an amino acid sequence represented by SEQ ID NO: 11, a heavy chain CDR2 including an amino acid sequence represented by SEQ ID NO: 12, and a heavy chain CDR3 including an amino acid sequence represented by SEQ ID NO: 13;

(A3) including a heavy chain CDR1 including an amino acid sequence represented by SEQ ID NO: 21, a heavy chain CDR2 including an amino acid sequence represented by SEQ ID NO: 22, and a heavy chain CDR3 including an amino acid sequence represented by SEQ ID NO: 23;

(A4) including a heavy chain CDR1 including an amino acid sequence represented by SEQ ID NO: 31, a heavy chain CDR2 including an amino acid sequence represented by SEQ ID NO: 32, and a heavy chain CDR3 including an amino acid sequence represented by SEQ ID NO: 33;

(A5) including a heavy chain CDR1 including an amino acid sequence represented by SEQ ID NO: 41, a heavy chain CDR2 including an amino acid sequence represented by SEQ ID NO: 42, and a heavy chain CDR3 including an amino acid sequence represented by SEQ ID NO: 43;

(A6) including a heavy chain CDR1 including an amino acid sequence represented by SEQ ID NO: 51, a heavy chain CDR2 including an amino acid sequence represented by SEQ ID NO: 52, and a heavy chain CDR3 including an amino acid sequence represented by SEQ ID NO: 53;

(A7) including a heavy chain CDR1 including an amino acid sequence represented by SEQ ID NO: 61, a heavy chain CDR2 including an amino acid sequence represented by SEQ ID NO: 62, and a heavy chain CDR3 including an amino acid sequence represented by SEQ ID NO: 63;

(A8) including a heavy chain CDR1 including an amino acid sequence represented by SEQ ID NO: 71, a heavy chain CDR2 including an amino acid sequence represented by SEQ ID NO: 72, and a heavy chain CDR3 including an amino acid sequence represented by SEQ ID NO: 73;

(A9) including a heavy chain CDR1 including an amino acid sequence represented by SEQ ID NO: 81, a heavy chain CDR2 including an amino acid sequence represented by SEQ ID NO: 82, and a heavy chain CDR3 including an amino acid sequence represented by SEQ ID NO: 83;

(A10) including a heavy chain CDR1 including an amino acid sequence represented by SEQ ID NO: 91, a heavy chain CDR2 including an amino acid sequence represented by SEQ ID NO: 92, and a heavy chain CDR3 including an amino acid sequence represented by SEQ ID NO: 93; and (A11) including a heavy chain CDR1 including an amino acid sequence represented by SEQ ID NO: 101, a heavy chain CDR2 including an amino acid sequence represented by SEQ ID NO: 102, and a heavy chain CDR3 including an amino acid sequence represented by SEQ ID NO: 103.

Preferably, the antibody satisfies any one of the following (B1) to (B11):

(B1) including a light chain CDR1 including an amino acid sequence represented by SEQ ID NO: 4, a light chain CDR2 including an amino acid sequence represented by SEQ ID NO: 5, and a light chain CDR3 including an amino acid sequence represented by SEQ ID NO: 6;

(B2) including a light chain CDR1 including an amino acid sequence represented by SEQ ID NO: 14, a light chain CDR2 including an amino acid sequence represented by SEQ ID NO: 15, and a light chain CDR3 including an amino acid sequence represented by SEQ ID NO: 16;

(B3) including a light chain CDR1 including an amino acid sequence represented by SEQ ID NO: 24, a light chain CDR2 including an amino acid sequence represented by SEQ ID NO: 25, and a light chain CDR3 including an amino acid sequence represented by SEQ ID NO: 26;

(B4) including a light chain CDR1 including an amino acid sequence represented by SEQ ID NO: 34, a light chain CDR2 including an amino acid sequence represented by SEQ ID NO: 35, and a light chain CDR3 including an amino acid sequence represented by SEQ ID NO: 36;

(B5) including a light chain CDR1 including an amino acid sequence represented by SEQ ID NO: 44, a light chain CDR2 including an amino acid sequence represented by SEQ ID NO: 45, and a light chain CDR3 including an amino acid sequence represented by SEQ ID NO: 46;

(B6) including a light chain CDR1 including an amino acid sequence represented by SEQ ID NO: 54, a light chain CDR2 including an amino acid sequence represented by SEQ ID NO: 55, and a light chain CDR3 including an amino acid sequence represented by SEQ ID NO: 56;

(B7) including a light chain CDR1 including an amino acid sequence represented by SEQ ID NO: 64, a light chain CDR2 including an amino acid sequence represented by SEQ ID NO: 65, and a light chain CDR3 including an amino acid sequence represented by SEQ ID NO: 66;

(B8) including a light chain CDR1 including an amino acid sequence represented by SEQ ID NO: 74, a light chain CDR2 including an amino acid sequence represented by SEQ ID NO: 75, and a light chain CDR3 including an amino acid sequence represented by SEQ ID NO: 76;

(B9) including a light chain CDR1 including an amino acid sequence represented by SEQ ID NO: 84, a light chain CDR2 including an amino acid sequence represented by SEQ ID NO: 85, and a light chain CDR3 including an amino acid sequence represented by SEQ ID NO: 86;

(B10) including a light chain CDR1 including an amino acid sequence represented by SEQ ID NO: 94, a light chain CDR2 including an amino acid sequence represented by SEQ ID NO: 95, and a light chain CDR3 including an amino acid sequence represented by SEQ ID NO: 96 and (B11) including a light chain CDR1 including an amino acid sequence represented by SEQ ID NO: 104, a light chain CDR2 including an amino acid sequence represented by SEQ ID NO: 105, and a light chain CDR3 including an amino acid sequence represented by SEQ ID NO: 106.

Preferably, the antibody satisfies any one of the following (AB1) to (AB 11):

(AB1) including a heavy chain CDR1 including an amino acid sequence represented by SEQ ID NO: 1, a heavy chain CDR2 including an amino acid sequence represented by SEQ ID NO: 2, a heavy chain CDR3 including an amino acid sequence represented by SEQ ID NO: 3, a light chain CDR1 including an amino acid sequence represented by SEQ ID NO: 4, a light chain CDR2 including an amino acid sequence represented by SEQ ID NO: 5, and a light chain CDR3 including an amino acid sequence represented by SEQ ID NO: 6;

(AB2) including a heavy chain CDR1 including an amino acid sequence represented by SEQ ID NO: 11, a heavy chain CDR2 including an amino acid sequence represented by SEQ ID NO: 12, a heavy chain CDR3 including an amino acid sequence represented by SEQ ID NO: 13, a light chain CDR1 including an amino acid sequence represented by SEQ ID NO: 14, a light chain CDR2 including an amino acid sequence represented by SEQ ID NO: 15, and a light chain CDR3 including an amino acid sequence represented by SEQ ID NO: 16;

(AB3) including a heavy chain CDR1 including an amino acid sequence represented by SEQ ID NO: 21, a heavy chain CDR2 including an amino acid sequence represented by SEQ ID NO: 22, a heavy chain CDR3 including an amino acid sequence represented by SEQ ID NO: 23, a light chain CDR1 including an amino acid sequence represented by SEQ ID NO: 24, a light chain CDR2 including an amino acid sequence represented by SEQ ID NO: 25, and a light chain CDR3 including an amino acid sequence represented by SEQ ID NO: 26;

(AB4) including a heavy chain CDR1 including an amino acid sequence represented by SEQ ID NO: 31, a heavy chain CDR2 including an amino acid sequence represented by SEQ ID NO: 32, a heavy chain CDR3 including an amino acid sequence represented by SEQ ID NO: 33, a light chain CDR1 including an amino acid sequence represented by SEQ ID NO: 34, a light chain CDR2 including an amino acid sequence represented by SEQ ID NO: 35, and a light chain CDR3 including an amino acid sequence represented by SEQ ID NO: 36;

(AB5) including a heavy chain CDR1 including an amino acid sequence represented by SEQ ID NO: 41, a heavy chain CDR2 including an amino acid sequence represented by SEQ ID NO: 42, a heavy chain CDR3 including an amino acid sequence represented by SEQ ID NO: 43, a light chain CDR1 including an amino acid sequence represented by SEQ ID NO: 44, a light chain CDR2 including an amino acid sequence represented by SEQ ID NO: 45, and a light chain CDR3 including an amino acid sequence represented by SEQ ID NO: 46;

(AB6) including a heavy chain CDR1 including an amino acid sequence represented by SEQ ID NO: 51, a heavy chain CDR2 including an amino acid sequence represented by SEQ ID NO: 52, a heavy chain CDR3 including an amino acid sequence represented by SEQ ID NO: 53, a light chain CDR1 including an amino acid sequence represented by SEQ ID NO: 54, a light chain CDR2 including an amino acid sequence represented by SEQ ID NO: 55, and a light chain CDR3 including an amino acid sequence represented by SEQ ID NO: 56;

(AB7) including a heavy chain CDR1 including an amino acid sequence represented by SEQ ID NO: 61, a heavy chain CDR2 including an amino acid sequence represented by SEQ ID NO: 62, a heavy chain CDR3 including an amino acid sequence represented by SEQ ID NO: 63, a light chain CDR1 including an amino acid sequence represented by SEQ ID NO: 64, a light chain CDR2 including an amino acid sequence represented by SEQ ID NO: 65, and a light chain CDR3 including an amino acid sequence represented by SEQ ID NO: 66;

(AB8) including a heavy chain CDR1 including an amino acid sequence represented by SEQ ID NO: 71, a heavy chain CDR2 including an amino acid sequence represented by SEQ ID NO: 72, a heavy chain CDR3 including an amino acid sequence represented by SEQ ID NO: 73, a light chain CDR1 including an amino acid sequence represented by SEQ ID NO: 74, a light chain CDR2 including an amino acid sequence represented by SEQ ID NO: 75, and a light chain CDR3 including an amino acid sequence represented by SEQ ID NO: 76;

(AB9) including a heavy chain CDR1 including an amino acid sequence represented by SEQ ID NO: 81, a heavy chain CDR2 including an amino acid sequence represented by SEQ ID NO: 82, a heavy chain CDR3 including an amino acid sequence represented by SEQ ID NO: 83, a light chain CDR1 including an amino acid sequence represented by SEQ ID NO: 84, a light chain CDR2 including an amino acid sequence represented by SEQ ID NO: 85, and a light chain CDR3 including an amino acid sequence represented by SEQ ID NO: 86;

(AB10) including a heavy chain CDR1 including an amino acid sequence represented by SEQ ID NO: 91, a heavy chain CDR2 including an amino acid sequence represented by SEQ ID NO: 92, a heavy chain CDR3 including an amino acid sequence represented by SEQ ID NO: 93, a light chain CDR1 including an amino acid sequence represented by SEQ ID NO: 94, a light chain CDR2 including an amino acid sequence represented by SEQ ID NO: 95, and a light chain CDR3 including an amino acid sequence represented by SEQ ID NO: 96; and (AB11) including a heavy chain CDR1 including an amino acid sequence represented by SEQ ID NO: 101, a heavy chain CDR2 including an amino acid sequence represented by SEQ ID NO: 102, a heavy chain CDR3 including an amino acid sequence represented by SEQ ID NO: 103, a light chain CDR1 including an amino acid sequence represented by SEQ ID NO: 104, a light chain CDR2 including an amino acid sequence represented by SEQ ID NO: 105, and a light chain CDR3 including an amino acid sequence represented by SEQ ID NO: 106.

Preferably, the antibody satisfies any one of the following (C1) to (C11):

(C1) including a heavy chain variable region including an amino acid sequence represented by SEQ ID NO: 7 and a light chain variable region including an amino acid sequence represented by SEQ ID NO: 9;

(C2) including a heavy chain variable region including an amino acid sequence represented by SEQ ID NO: 17 and a light chain variable region including an amino acid sequence represented by SEQ ID NO: 19;

(C3) including a heavy chain variable region including an amino acid sequence represented by SEQ ID NO: 27 and a light chain variable region including an amino acid sequence represented by SEQ ID NO: 29;

(C4) including a heavy chain variable region including an amino acid sequence represented by SEQ ID NO: 37 and a light chain variable region including an amino acid sequence represented by SEQ ID NO: 39;

(C5) including a heavy chain variable region including an amino acid sequence represented by SEQ ID NO: 47 and a light chain variable region including an amino acid sequence represented by SEQ ID NO: 49;

(C6) including a heavy chain variable region including an amino acid sequence represented by SEQ ID NO: 57 and a light chain variable region including an amino acid sequence represented by SEQ ID NO: 59;

(C7) including a heavy chain variable region including an amino acid sequence represented by SEQ ID NO: 67 and a light chain variable region including an amino acid sequence represented by SEQ ID NO: 69;

(C8) including a heavy chain variable region including an amino acid sequence represented by SEQ ID NO: 77 and a light chain variable region including an amino acid sequence represented by SEQ ID NO: 79;

(C9) including a heavy chain variable region including an amino acid sequence represented by SEQ ID NO: 87 and a light chain variable region including an amino acid sequence represented by SEQ ID NO: 89;

(C10) including a heavy chain variable region including an amino acid sequence represented by SEQ ID NO: 97 and a light chain variable region including an amino acid sequence represented by SEQ ID NO: 99; and (C11) including a heavy chain variable region including an amino acid sequence represented by SEQ ID NO: 107 and a light chain variable region including an amino acid sequence represented by SEQ ID NO: 109.

An aspect of the present disclosure is an antibody that specifically binds to an extracellular domain of human LPA1, wherein the antibody does not specifically bind to an extracellular domain of human LPA2, the antibody does not specifically bind to an extracellular domain of human LPA3, and the antibody satisfies any one of the following (C1') to (C11'):

(C1') including a heavy chain variable region including an amino acid sequence represented by SEQ ID NO: 7 with 1 to 10 amino acids substituted, added, or deleted, or including an amino acid sequence having 90% or higher of identity with the amino acid sequence represented by SEQ ID NO: 7, and a light chain variable region including an amino acid sequence represented by SEQ ID NO: 9 with 1 to 10 amino acids substituted, added, or deleted, or including an amino acid sequence having 90% or higher of identity with the amino acid sequence represented by SEQ ID NO: 9;

(C2') including a heavy chain variable region including an amino acid sequence represented by SEQ ID NO: 17 with 1 to 10 amino acids substituted, added, or deleted, or including an amino acid sequence having 90% or higher of identity with the amino acid sequence represented by SEQ ID NO: 17, and a light chain variable region including an amino acid sequence represented by SEQ ID NO: 19 with 1 to 10 amino acids substituted, added, or deleted, or including an amino acid sequence having 90% or higher of identity with the amino acid sequence represented by SEQ ID NO: 19;

(C3') including a heavy chain variable region including an amino acid sequence represented by SEQ ID NO: 27 with 1 to 10 amino acids substituted, added, or deleted, or including an amino acid sequence having 90% or higher of identity with the amino acid sequence represented by SEQ ID NO: 27, and a light chain variable region including an amino acid sequence represented by SEQ ID NO: 29 with 1 to 10 amino acids substituted, added, or deleted, or including an amino acid sequence having 90% or higher of identity with the amino acid sequence represented by SEQ ID NO: 29;

(C4') including a heavy chain variable region including an amino acid sequence represented by SEQ ID NO: 37 with 1 to 10 amino acids substituted, added, or deleted, or including an amino acid sequence having 90% or higher of identity with the amino acid sequence represented by SEQ ID NO: 37, and a light chain variable region including an amino acid sequence represented by SEQ ID NO: 39 with 1 to 10 amino acids substituted, added, or deleted, or including an amino acid sequence having 90% or higher of identity with the amino acid sequence represented by SEQ ID NO: 39;

(C5') including a heavy chain variable region including an amino acid sequence represented by SEQ ID NO: 47 with 1 to 10 amino acids substituted, added, or deleted, or including an amino acid sequence having 90% or higher of identity with the amino acid sequence represented by SEQ ID NO: 47, and a light chain variable region including an amino acid sequence represented by SEQ ID NO: 49 with 1 to 10 amino acids substituted, added, or deleted, or including an amino acid sequence having 90% or higher of identity with the amino acid sequence represented by SEQ ID NO: 49;

(C6') including a heavy chain variable region including an amino acid sequence represented by SEQ ID NO: 57 with 1 to 10 amino acids substituted, added, or deleted, or including an amino acid sequence having 90% or higher of identity with the amino acid sequence represented by SEQ ID NO: 57, and a light chain variable region including an amino acid sequence represented by SEQ ID NO: 59 with 1 to 10 amino acids substituted, added, or deleted, or including an amino acid sequence having 90% or higher of identity with the amino acid sequence represented by SEQ ID NO: 59;

(C7') including a heavy chain variable region including an amino acid sequence represented by SEQ ID NO: 67 with 1 to 10 amino acids substituted, added, or deleted, or including an amino acid sequence having 90% or higher of identity with the amino acid sequence represented by SEQ ID NO: 67, and a light chain variable region including an amino acid sequence represented by SEQ ID NO: 69 with 1 to 10 amino acids substituted, added, or deleted, or including an amino acid sequence having 90% or higher of identity with the amino acid sequence represented by SEQ ID NO: 69;

(C8') including a heavy chain variable region including an amino acid sequence represented by SEQ ID NO: 77 with 1 to 10 amino acids substituted, added, or deleted, or including an amino acid sequence having 90% or higher of identity with the amino acid sequence represented by SEQ ID NO: 77, and a light chain variable region including an amino acid sequence represented by SEQ ID NO: 79 with 1 to 10 amino acids substituted, added, or deleted, or including an amino acid sequence having 90% or higher of identity with the amino acid sequence represented by SEQ ID NO: 79;

(C9') including a heavy chain variable region including an amino acid sequence represented by SEQ ID NO: 87 with 1 to 10 amino acids substituted, added, or deleted, or including an amino acid sequence having 90% or higher of identity with the amino acid sequence represented by SEQ ID NO: 87, and a light chain variable region including an amino acid sequence represented by SEQ ID NO: 89 with 1 to 10 amino acids substituted, added, or deleted, or including an amino acid sequence having 90% or higher of identity with the amino acid sequence represented by SEQ ID NO: 89;

(C10') including a heavy chain variable region including an amino acid sequence represented by SEQ ID NO: 97 with 1 to 10 amino acids substituted, added, or deleted, or including an amino acid sequence having 90% or higher of identity with the amino acid sequence represented by SEQ ID NO: 97, and a light chain variable region including an amino acid sequence represented by SEQ ID NO: 99 with 1 to 10 amino acids substituted, added, or deleted, or including an amino acid sequence having 90% or higher of identity with the amino acid sequence represented by SEQ ID NO: 99; and (C11') including a heavy chain variable region including an amino acid sequence represented by SEQ ID NO: 107 with 1 to 10 amino acids substituted, added, or deleted, or including an amino acid sequence having 90% or higher of identity with the amino acid sequence represented by SEQ ID NO: 107, and a light chain variable region including an amino acid sequence represented by SEQ ID NO: 109 with 1 to 10 amino acids substituted, added, or deleted, or including an amino acid sequence having 90% or higher of identity with the amino acid sequence represented by SEQ ID NO: 109.

Preferably, the antibody includes an activity of blocking an LPA1-dependent cell function.

An aspect of the present disclosure is a second antibody that specifically binds to an extracellular domain of human LPA1, wherein the second antibody does not specifically bind to an extracellular domain of human LPA2, the second antibody does not specifically bind to an extracellular domain of human LPA3, and the second antibody competitively inhibits a binding between a first antibody that is the above antibody and a receptor.

Preferably, the second antibody includes an activity of blocking an LPA1-dependent cell function.

Preferably, the antibody or the second antibody is a humanized antibody or a chimeric antibody.

Preferably, the antibody or the second antibody is a multispecific antibody.

Preferably, the antibody or the second antibody is a modified antibody bonded with another molecule.

Preferably, the modified antibody is an antibody-drug conjugate.

An aspect of the present disclosure is a nucleic acid encoding the above antibody or second antibody.

An aspect of the present disclosure is a cell including the above nucleic acid.

An aspect of the present disclosure is a medicament including the above antibody as an active ingredient.

Preferably, the medicament is used for treating a disease, a disorder, or a condition involving LPA1-dependent cell dysfunction.

Preferably, the medicament is used for treating tissue fibrosis, cell proliferative disease, pain, inflammatory disease, autoimmune disease, metabolic disease, cardiovascular disorder, urological disease, or ophthalmological disease.

Preferably, the tissue fibrosis is hepatic fibrosis, kidney fibrosis, pulmonary fibrosis, skin fibrosis, cardiovascular fibrosis, or gastrointestinal fibrosis.

Preferably, the hepatic fibrosis is nonalcoholic steatohepatitis (NASH), nonalcoholic fatty liver disease (NAFLD), liver cirrhosis, ischemia reperfusion, post-liver implantation disorder, necrotizing hepatitis, hepatitis B, hepatitis C, primary biliary liver cirrhosis, or primary sclerosing cholangitis.

Preferably, the liver cirrhosis is alcohol-induced, drug-induced, or chemically induced.

Preferably, the kidney fibrosis is proliferative glomerulonephritis, sclerosing glomerulonephritis, nephrogenic fibrosing dermopathy, diabetic nephropathy, renal tubulointerstitial fibrosis, or focal segmental glomerulosclerosis.

Preferably, the pulmonary fibrosis is lung interstitial fibrosis, drug-induced sarcoidosis, idiopathic pulmonary fibrosis, asthma, chronic obstructive lung disease, diffuse alveolar damage disease, pulmonary hypertension, or neonatal bronchopulmonary malformation.

Preferably, the skin fibrosis is scleroderma, keloid scarring, psoriasis, hypertrophic scarring, or pseudo-scleroderma.

Preferably, the cardiovascular fibrosis is atherosclerosis, coronary artery restenosis, congestive cardiomyopathy, heart failure, heart implantation, or myocardial fibrosis.

Preferably, the gastrointestinal fibrosis is collagenous colitis, villous atrophy, crypt hyperplasia, polyp formation, Crohn's fibrosis, gastric ulcer healing, or scar after abdominal adhesion surgery.

Preferably, the fibrosis is caused by a bone-related fiberization disease and has rheumatoid pannus formation.

Preferably, the cell proliferative disease is tumor cell proliferation, tumor infiltration and metastasis, or controlled angiogenesis.

Preferably, the cell proliferative disease is hematological cancer or solid carcinoma.

Preferably, the solid carcinoma is breast cancer, malignant breast tumor, gastric cancer, melanoma, non-small-cell lung cancer, pulmonary adenocarcinoma, gastric cancer, pancreatic cancer, ovarian cancer, uterine cancer, cervical cancer, hepatoma, prostate cancer, urothelial cancer, renal cell cancer, or squamous cell cancer.

Preferably, the squamous cell cancer is oral squamous cell carcinoma, esophageal squamous cell carcinoma, or pharyngeal squamous cell carcinoma.

Preferably, the pain is fibromyalgia pain, cancer pain, or diabetic neuropathy pain.

Preferably, the inflammatory disease is rheumatoid arthritis, sepsis, chronic obstructive lung disease, inflammatory bowel disease, implanted organ rejection, Guillain-Barre syndrome, or multiple sclerosis.

Preferably, the metabolic disease is obesity or insulin-resistant diabetes.

Preferably, the cardiovascular disorder is stroke, hypertensive nephropathy, or Raynaud's phenomenon.

Preferably, the nervous system disorder is hydrocephalus, schizophrenia, depression, or dementia.

Preferably, the urologic disease is prostatic hyperplasia or urinary incontinence.

Preferably, the ophthalmological disease is ischemic retinopathy, diabetic retinopathy, or age-related macular degeneration.

Effect of Invention

According to the present disclosure, it is possible to provide a novel antibody that specifically binds to an extracellular domain of LPA1, and a relevant technology.

BRIEF DESCRIPTION OF DRAWINGS

FIG. 6E is a graph presenting a dose dependency of an inhibitory activity of an antibody (210309-4-A) on mouse LPA1.

FIG. 6F is a graph presenting a dose dependency of an inhibitory activity of an antibody (210310-1-D) on mouse LPA1.

FIG. 6G is a graph presenting a dose dependency of an inhibitory activity of an antibody (210420-4-E) on mouse LPA1.

Figure 12E:
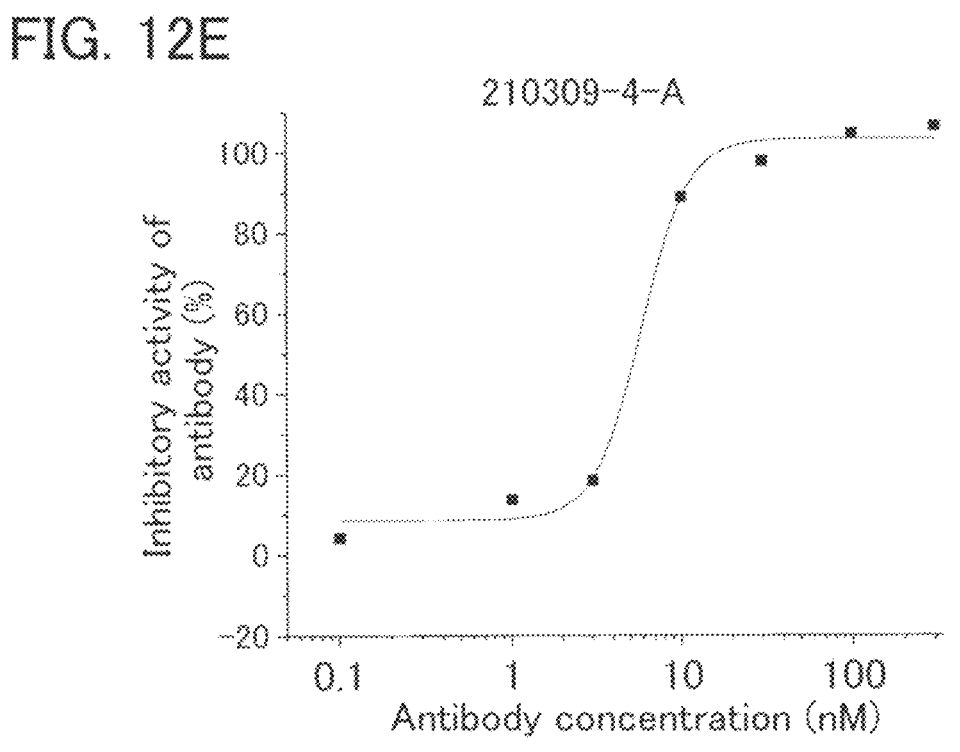

FIG. 12E is a graph presenting a dose dependency of an inhibitory activity of an antibody (210309-4-A) on human LPA1.

BEST MODE FOR CARRYING OUT THE INVENTION

Figure 1A:
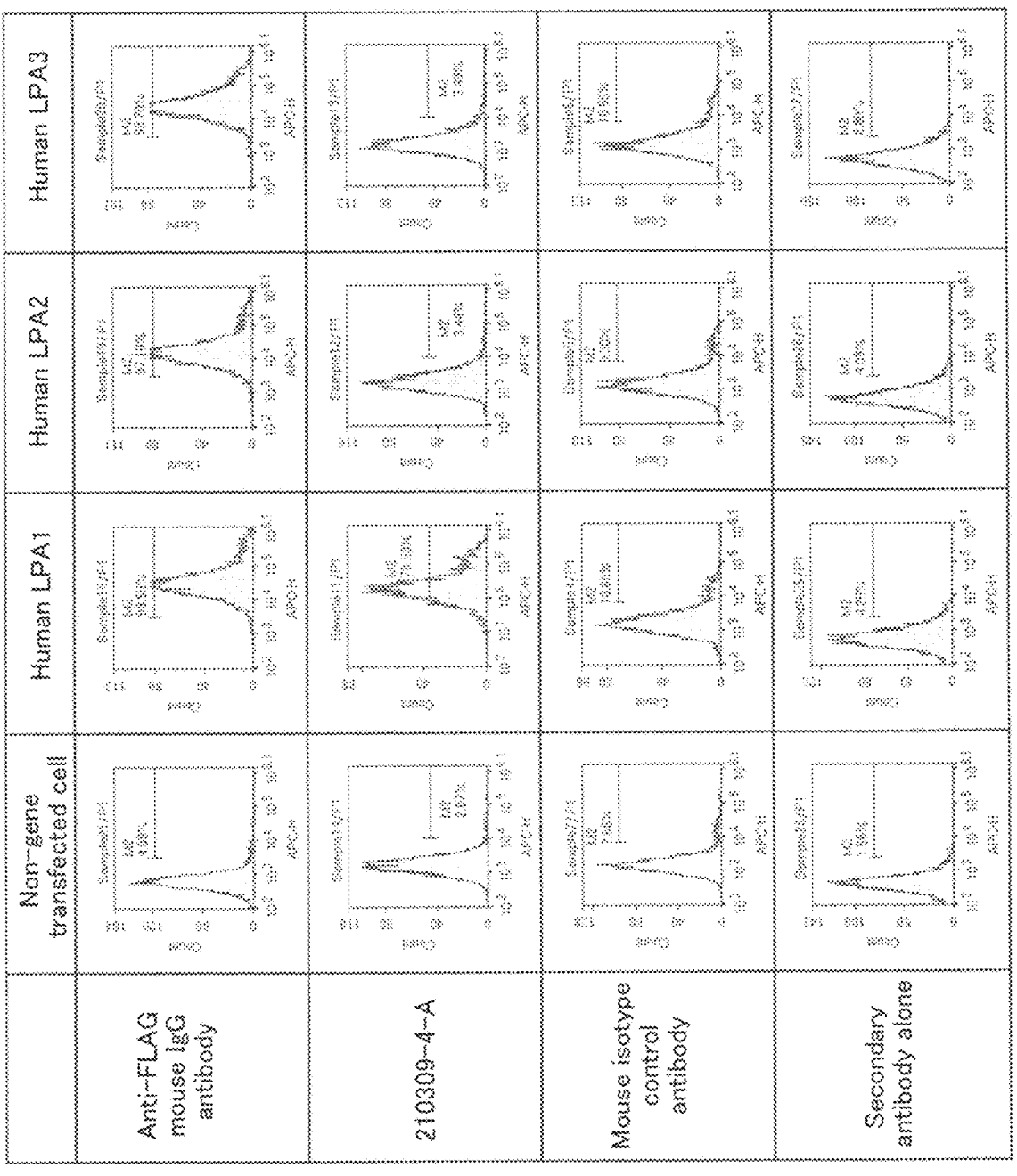
FIG. 1A is a histogram presenting results of flow cytometry performed in Example 4, showing binding properties between an antibody and human LPA1 to LPA3.

In the present disclosure, the complementarity determining region is abbreviated as CDR. In the present disclosure, a heavy chain variable region, a heavy chain constant region, a light chain variable region, and a light chain constant region are abbreviated as VH, CH, VL, and CL respectively in some cases. In the present disclosure, the term "antibody" may be synonymous with "immunoglobulin". The term "nucleic acid" in the present disclosure may be synonymous with "DNA" or "gene".

<Human LPA1>

Lysophosphatidic acid receptor 1 (LPA1) is a type of G protein coupled receptors (GPCR), which penetrates cell membranes seven times and has an N-terminal extracellularly oriented and a C-terminal intracellularly oriented. A gene (cDNA) coding for human LPA1 has already been isolated, and an amino acid sequence of human LPA1 is also known. Sequence information of LPA1 can be obtained from gene databases (e.g., National Center for Biotechnology Information (NCBI) Reference Sequence: NP001392). As an example, the amino acid sequence of human LPA1 is represented by SEQ ID NO: 111.

Each domain in human LPA1 is considered to correspond to each of the following parts in the amino acid sequence represented by SEQ ID NO: 111. The amino acid numbers are described on the left side, and domains are described on the right side. Each boundary between the domains may be slightly variable.

1 to 50: N-terminal domain 76 to 83: Intracellular first loop domain 108 to 121: Extracellular first loop domain 145 to 163: Intracellular second loop domain 185 to 204: Extracellular second loop domain 226 to 255: Intracellular third loop domain 281 to 294: Extracellular third loop domain 316 to 364: C-terminal domain As human LPA1, various variants such as amino acid substitutes are known in addition to the amino acid sequence represented by SEQ ID NO: 111. The "human LPA1" in the present disclosure includes the aforementioned variants as long as the variants have extracellular domains and LPA1 functions.

A gene (cDNA) coding for human LPA2 has already been isolated, and the amino acid sequence of human LPA2 is also known. Sequence information of LPA2 can be obtained from gene databases (NP_004711, SEQ ID NO: 119). A gene (cDNA) coding for human LPA3 has already been isolated, and the amino acid sequence of human LPA3 is also known. The sequence information of LPA3 can be obtained from gene databases (NP_036284, SEQ ID NO: 121).

<Anti-LPA1 Antibody>

The antibody disclosed in the present application specifically binds to an extracellular domain of human LPA1 and does not specifically bind to extracellular domains of human LPA2 and human LPA3.

An antibody according to an embodiment includes:

a heavy chain CDR1 including an amino acid sequence represented by SEQ ID NO: 1, 11,21,31,41, 51, 61, 71, 81, 91, or 101;

a heavy chain CDR2 including an amino acid sequence represented by SEQ ID NO: 2, 12, 22, 32, 42, 52, 62, 72, 82, 92, or 102;

a heavy chain CDR3 including an amino acid sequence represented by SEQ ID NO: 3, 13, 23, 33, 43, 53, 63, 73, 83, 93, or 103;

a light chain CDR1 including an amino acid sequence represented by SEQ ID NO: 4, 14, 24, 34, 44, 54, 64, 74, 84, 94, or 104;

a light chain CDR2 including an amino acid sequence represented by SEQ ID NO: 5, 15, 25, 35, 45, 55, 65, 75, 85, 95, or 105; and a light chain CDR3 including an amino acid sequence represented by SEQ ID NO: 6, 16, 26, 36, 46, 56, 66, 76, 86, 96, or 106.

In an antibody according to an embodiment, the heavy chain CDRs 1 to 3 satisfy any one of the above (A1) to (A11).

In an antibody according to an embodiment, the light chain CDRs 1 to 3 satisfy any one of the above (B1) to (B11).

In an antibody according to an embodiment, the heavy chain CDRs 1 to 3 and the light chain CDRs 1 to 3 satisfy any one of the above (AB1) to (AB11).

In an antibody according to an embodiment, the heavy chain variable region and the light chain variable region satisfy any one of the above (C1) to (C11).

The heavy chain variable region (SEQ ID NO: 7) identified in (C1) includes the heavy chain CDRs 1 to 3 (SEQ ID NO: 1 to 3) identified in (A1) or (AB1). The light chain variable region (SEQ ID NO: 9) identified in (C1) includes the light chain CDRs 1 to 3 (SEQ ID NO: 4 to 6) identified in (B1) or (AB1). Examples of an antibody satisfying (A1), (B1), (AB1), or (C₁) include "210309-4-A" described in Examples below.

The heavy chain variable region (SEQ ID NO: 17) identified in (C2) includes the heavy chain CDRs 1 to 3 (SEQ ID NO: 11 to 13) identified in (A2) or (AB2). The light chain variable region (SEQ ID NO: 19) identified in (C2) includes the light chain CDRs 1 to 3 (SEQ ID NO: 14 to 16) identified in (B2) or (AB2). Examples of an antibody satisfying (A2), (B2), (AB2), or (C2) include "210309-1-C" described in Examples below.

The heavy chain variable region (SEQ ID NO: 27) identified in (C3) includes the heavy chain CDRs 1 to 3 (SEQ ID NO: 21 to 23) identified in (A3) or (AB3). The light chain variable region (SEQ ID NO: 29) identified in (C3) includes the light chain CDRs 1 to 3 (SEQ ID NO: 24 to 26) identified in (B3) or (AB3). Examples of an antibody satisfying (A3), (B3), (AB3), or (C3) include "210309-1-G" described in Examples below.

The heavy chain variable region (SEQ ID NO: 37) identified in (C4) includes the heavy chain CDRs 1 to 3 (SEQ ID NO: 31 to 33) identified in (A4) or (AB4). The light chain variable region (SEQ ID NO: 39) identified in (C4) includes the light chain CDRs 1 to 3 (SEQ ID NO: 34 to 36) identified in (B4) or (AB4). Examples of an antibody satisfying (A4), (B4), (AB4), or (C4) include "210309-2-A" described in Examples below.

The heavy chain variable region (SEQ ID NO: 47) identified in (C5) includes the heavy chain CDRs 1 to 3 (SEQ ID NO: 41 to 43) identified in (A5) or (AB5). The light chain variable region (SEQ ID NO: 49) identified in (C5) includes the light chain CDRs 1 to 3 (SEQ ID NO: 44 to 46) identified in (B5) or (AB5). Examples of an antibody satisfying (A5), (B5), (AB5), or (C5) include "210309-2-D" described in Examples below.

The heavy chain variable region (SEQ ID NO: 57) identified in (C6) includes the heavy chain CDRs 1 to 3 (SEQ ID NO: 51 to 53) identified in (A6) or (AB6). The light chain variable region (SEQ ID NO: 59) identified in (C6) includes the light chain CDRs 1 to 3 (SEQ ID NO: 54 to 56) identified in (B6) or (AB6). Examples of an antibody satisfying (A6), (B6), (AB6), or (C6) include "210310-1-D" described in Examples below.

The heavy chain variable region (SEQ ID NO: 67) identified in (C7) includes the heavy chain CDRs 1 to 3 (SEQ ID NO: 61 to 63) identified in (A7) or (AB7). The light chain variable region (SEQ ID NO: 69) identified in (C7) includes the light chain CDRs 1 to 3 (SEQ ID NO: 64 to 66) identified in (B7) or (AB7). Examples of an antibody satisfying (A7), (B7), (AB7), or (C7) include "210420-4-E" described in Examples below.

The heavy chain variable region (SEQ ID NO: 77) identified in (C8) includes the heavy chain CDRs 1 to 3 (SEQ ID NO: 71 to 73) identified in (A8) or (AB8). The light chain variable region (SEQ ID NO: 79) identified in (C8) includes the light chain CDRs 1 to 3 (SEQ ID NO: 74 to 76) identified in (B8) or (AB8). Examples of an antibody satisfying (A8), (B8), (AB8), or (C8) include "210420-1-H" described in Examples below.

The heavy chain variable region (SEQ ID NO: 87) identified in (C9) includes the heavy chain CDRs 1 to 3 (SEQ ID NO: 81 to 83) identified in (A9) or (AB9). The light chain variable region (SEQ ID NO: 89) identified in (C9) includes the light chain CDRs 1 to 3 (SEQ ID NO: 84 to 86) identified in (B9) or (AB9). Examples of an antibody satisfying (A9), (B9), (AB9), or (C9) include "210420-3-E" described in Examples below.

The heavy chain variable region (SEQ ID NO: 97) identified in (C10) includes the heavy chain CDRs 1 to 3 (SEQ ID NO: 91 to 93) identified in (A10) or (AB10). The light chain variable region (SEQ ID NO: 99) identified in (C10) includes the light chain CDRs 1 to 3 (SEQ ID NO: 94 to 96) identified in (B10) or (AB10). Examples of an antibody satisfying (A10), (B10), (AB10), or (C10) include "211222-1-G" described in Examples below.

The heavy chain variable region (SEQ ID NO: 107) identified in (C11) includes the heavy chain CDRs 1 to 3 (SEQ ID NO: 101 to 103) identified in (A1 1) or (AB11). The light chain variable region (SEQ ID NO: 109) identified in (C11) includes the light chain CDRs 1 to 3 (SEQ ID NO: 104 to 106) identified in (B11) or (AB11). Examples of an antibody satisfying (A1 1), (B11), (AB11), or (C11) include "211222-1-A" described in Examples below.

SEQ ID NO: 1, SEQ ID NO: 21, SEQ ID NO: 31, and SEQ ID NO: 41 have a same amino acid sequence. SEQ ID NO: 2 and SEQ ID NO: 32 have a same amino acid sequence. SEQ ID NO: 6, SEQ ID NO: 16, SEQ ID NO: 26, SEQ ID NO: 36, and SEQ ID NO: 46 have a same amino acid sequence. SEQ ID NO: 15, SEQ ID NO: 25, SEQ ID NO: 35, SEQ ID NO: 45, SEQ ID NO: 65, SEQ ID NO: 75, SEQ ID NO: 85, and SEQ ID NO: 105 have a same amino acid sequence. SEQ ID NO: 24, SEQ ID NO: 34, SEQ ID NO: 54, SEQ ID NO: 94, and SEQ ID NO: 104 have a same amino acid sequence. SEQ ID NO: 51, SEQ ID NO: 91, and SEQ ID NO: 101 have a same amino acid sequence. SEQ ID NO: 52 and SEQ ID NO: 92 have a same amino acid sequence. SEQ ID NO: 53, SEQ ID NO: 93, and SEQ ID NO: 103 have a same amino acid sequence. SEQ ID NO: 55 and SEQ ID NO: 95 have a same amino acid sequence. SEQ ID NO: 56, SEQ ID NO: 66, SEQ ID NO: 76, SEQ ID NO: 86, SEQ ID NO: 96, and SEQ ID NO: 106 have a same amino acid sequence. SEQ ID NO: 61, SEQ ID NO: 71, and SEQ ID NO: 81 have a same amino acid sequence. SEQ ID NO: 62, SEQ ID NO: 72, and SEQ ID NO: 82 have a same amino acid sequence. SEQ ID NO: 63, SEQ ID NO: 73, and SEQ ID NO: 83 have a same amino acid sequence. SEQ ID NO: 64, SEQ ID NO: 74, and SEQ ID NO: 84 have a same amino acid sequence.

The above antibody may be a functional fragment of an antibody. Herein, the "functional fragment of an antibody" refers to a partial fragment of an antibody (i.e. immunoglobulin), which retains at least one action against antigens. Examples of the partial fragment include F(ab')2, Fab, Fv, disulfide-bonded Fv, single-stranded antibodies (scFv, VH-VL), VH, and polymers thereof, as well as a fusion thereof with the heavy chain CH3 region, and also include various CDRs such as CDR1, CDR2, and CDR3, and a linked assembly of these CDRs, as well as a fusion of these CDRs or the CDR linked assembly with a heavy chain CH3 region. That means, the antibodies according to the present disclosure include partial fragments of antibodies as described above. A partial fragment of the antibody is referred to as an "antibody fragment" in some cases.

When the aforementioned antibody is a functional fragment, the antibody has, for example, the following effects. That means, when the anti-LPA1 antibody according to the present disclosure is applied for a medicament as described below, use of a full-length antibody such as IgG type may cause damage to a target tissue leading to side effects, in addition to inhibited cell functions via a target receptor. In such a case, the side effects can be easily avoided by adopting the "functional fragment of antibody" using only a variable region.

The above antibody may be a multispecific antibody. A multispecific antibody according to this embodiment has at least a first specific binding property that the antibody binds specifically to the extracellular domain of human LPA1 and not specifically to the extracellular domains of human LPA2 and human LPA3, and a second specific binding property different from the first specific binding property. The second specific binding property may be targeted to human LPA1 or to other target molecules. Examples of the multispecific antibody include a diabody as a type of bispecific antibodies.

The class (isotype) of the above antibodies is not particularly limited. For example, the antibodies may belong to any class of IgG, IgM, IgA, IgD, IgE and the like. Furthermore, the subclass of the above antibodies is not particularly limited, neither. For example, if the antibody belongs to the IgG class, the subclass thereof may be any of IgG1, IgG2, IgG3, IgG4, and the like.

In a preferable embodiment, the above antibodies have an activity of blocking LPA1-dependent cell functions. The LPA1-dependent cell functions are induced through activation of a protein such as trimeric G proteins and β-arrestin, which is conjugated to an intracellular portion of LPA1 to act for intracellular signaling. The LPA1-dependent activation of the cell functions is induced by stimulation of an LPA1 ligand or an LPA1 ligand-independent high expression of LPA1. Examples of the cell functions include a change in intracellular cyclic adenosine monophosphate (cAMP), a change in intracellular calcium ions, binding of guanosine triphosphate (GTP) to a low molecular weight G protein Rho, cell proliferation, cell migration, production of cytokines and chemokines, and cell transformation.

The extracellular domain of LPA1 to which the above antibodies specifically bind may be any of an N-terminal domain, an extracellular first loop domain, an extracellular second loop domain, and an extracellular third loop domain. The above antibodies may bind to only one of these extracellular domains or to two or more of them.

The present disclosure encompasses antibodies that are "functionally equivalent" to the anti-LPA1 antibodies described above. The functionally equivalent antibodies include antibodies having the same epitopes as of the anti-LPA1 antibodies. For example, epitopes of eleven types of anti-LPA1 antibodies specifically described in Examples below are analyzed by an epitope mapping method using a partial peptide of LPA1 or the like. Then, a synthetic peptide including identified epitopes can be used as an antigen to obtain an anti-LPA1 antibody that binds to the same epitopes as the above eleven anti-LPA1 antibodies. Furthermore, amino acid sequences of a heavy chain variable region and a light chain variable region of the obtained anti-LPA1 antibody can be determined to identify amino acid sequences of the heavy chain CDRs 1 to 3 and the light chain CDRs 1 to 3.

As an example of the antibodies functionally equivalent to the above antibodies, the present disclosure encompasses an antibody that binds specifically to the extracellular domain of human LPA1 and not specifically to the extracellular domains of human LPA2 and human LPA3 and satisfies any one of the (C1') to (C11') described above. In (C1') to (C11'), the number of substituted, added, or deleted amino acids is preferably 1 to 8, more preferably 1 to 5, particularly preferably 1 to 3. The identity of the amino acid sequences described above is preferably 92% or higher, more preferably 95% or higher, and particularly preferably 97% or higher. In a preferable embodiment, the antibody has an activity of blocking the LPA1-dependent cell functions.

Examples of a method for determining whether epitopes are identical between two antibodies include a method using a competition experiment. For example, if binding between the above eleven anti-LPA1 antibodies or functional fragments thereof as first antibodies and the receptors is competitively inhibited by second antibodies to be tested, the second antibodies are considered to bind to the same epitopes as for the first antibodies. As an example of the antibodies that are functionally equivalent to the above antibodies, the present disclosure encompasses second antibodies that bind specifically to the extracellular domain of human LPA1 and not specifically to the extracellular domains of human LPA2 and human LPA3, and competitively inhibit the binding between the above antibodies (first antibodies) and the receptors. In a preferable embodiment, the second antibodies have an activity of blocking the LPA1-dependent cell functions.

<Humanized Antibody>

The present disclosure encompasses the above antibodies that are humanized antibodies. The humanized antibodies refer to antibodies in which the CDRs are derived from non-human animals and other regions (e.g., framework regions and constant regions) are derived from humans. Methods for constructing and producing humanized antibodies are described later.

<Chimeric Antibody>

The present disclosure encompasses the above antibodies that are chimeric antibodies. The chimeric antibodies refer to antibodies in which the heavy chain variable region (VH) and light chain variable region (VL) are derived from non-human animals, and other regions such as the heavy chain constant region (CH) and light chain constant region (CL) are derived from humans. Methods for constructing and producing chimeric antibodies are described later.

<Nucleic Acid>

The present disclosure encompasses nucleic acids (DNA) encoding the above antibodies. The nucleic acids include, e.g., a first nucleic acid encoding the heavy chain variable region and/or a second nucleic acid encoding the light chain variable region.

The heavy chain variable region which the first nucleic acid encodes includes, e.g., a heavy chain CDR1 including an amino acid sequence represented by SEQ ID NO: 1, 11, 21, 31, 41, 51, 61, 71, 81, 91, or 101, a heavy chain CDR2 including an amino acid sequence represented by SEQ ID NO: 2, 12, 22, 32, 42, 52, 62, 72, 82, 92, or 102, and a heavy chain CDR3 including an amino acid sequence represented by SEQ ID NO: 3, 13, 23, 33, 43, 53, 63, 73, 83, 93, or 103. The heavy chain variable region which the first nucleic acid encodes includes, e.g., the heavy chain CDRs 1 to 3 identified in any one of (A1) to (A1 1) above. The heavy chain variable region which the first nucleic acid encodes is identified e.g. in any one of (C1) to (C11) above. The heavy chain variable region which the first nucleic acid encodes is identified e.g. in any one of (C1') to (C11') above.

The light chain variable region which the second nucleic acid encodes includes, e.g., a light chain CDR1 including an amino acid sequence represented by SEQ ID NO: 4, 14, 24, 34, 44, 54, 64, 74, 84, 94, or 104, a light chain CDR2 including an amino acid sequence represented by SEQ ID NO: 5, 15, 25, 35, 45, 55, 65, 75, 85, 95, or 105, and a light chain CDR3 including an amino acid sequence represented by SEQ ID NO: 6, 16, 26, 36, 46, 56, 66, 76, 86, 96, or 106. The light chain variable region which the second nucleic acid encodes includes, e.g., heavy chain CDRs 1 to 3 identified in any one of (B1) to (B11) above. The light chain variable region which the second nucleic acid encodes is identified e.g. in any one of (C1) to (C11) above. The light chain variable region which the second nucleic acid encodes is identified in e.g., any one of (C1') to (C11') above.

The above nucleic acids may be incorporated into a vector. The vector is selected as appropriate depending on a type or the like of a host cell to be transduced with the vector. Examples of the vector include a gene therapy vector. In the case of a gene therapy vector, the vector itself can be directly administered into a living body.

<Cell>

The present disclosure encompasses a cell containing the above nucleic acids. Examples of the cell include a cell containing a vector into which the above nucleic acids are incorporated. The type of the cell is not particularly limited as long as the cell can express the above nucleic acids, e.g., the above vector is functional in the cell. Examples of the cell include animal cells (e.g., COS cells, CHO cells), yeast, bacteria (e.g., *E. coli*), plant cells, and insect cells.

<Method for Producing Antibody>

The above antibodies can be produced using a genetic recombination method. That means, recombinant cells that express the above nucleic acids can be constructed to obtain the above antibodies from culture medium of the cells.

<Construction and Preparation of Humanized Antibody>

A method for constructing and producing humanized antibodies will be explained. As an example, a method for constructing and producing humanized antibodies having the heavy chain CDRs 1 to 3 and the light chain CDRs 1 to 3 identified in (AB1) above will be described. As DNAs encoding each CDR, DNAs coding for the amino acid sequences presented in SEQ ID NO: 1 to 6 are first prepared. The DNAs can be prepared by using a known method such as PCR. The DNA can also be prepared by chemical synthesis.

Next, these DNAs are used to prepare DNAs encoding variable regions in which the heavy chain CDRs 1 to 3 are implanted into a framework region (FR) of a VH in any human antibody. Similarly, DNAs coding for variable regions in which the light chain CDRs 1 to 3 are implanted into an FR of a VL in any human antibody are prepared. Each DNA prepared is inserted into a vector having sequences coding for a CH or CL of a human antibody to construct a humanized antibody expression vector. The constructed expression vector is introduced into a host cell to obtain a recombinant cell that expresses a humanized antibody. Then, this recombinant cell is cultured to obtain a desired humanized antibody from the culture supernatant.

Humanized antibodies having the heavy chain CDRs 1 to 3 and light chain CDRs 1 to 3 identified in (AB2) to (AB 11) above can be constructed and produced by the same method.

<Construction and Preparation of Chimeric Antibody>

A method for constructing and producing a chimeric antibody will be explained. As an example, a method for constructing and producing a chimeric antibody having the heavy chain variable region (VH) and light chain variable region (VL) identified in (C1) above will be described. As a DNA coding for the VL, a DNA encoding the amino acid sequence represented by SEQ ID NO: 7 is first prepared. As a DNA encoding the VL, a DNA encoding the amino acid sequence represented by SEQ ID NO: 9 is prepared. The DNA can be prepared by using a known method such as PCR. The DNA can also be prepared by chemical synthesis.

The obtained DNAs encoding the VH or VL are each inserted into a vector having a sequence coding for the CH or CL respectively of a human antibody to construct a chimeric antibody expression vector. The vector having the sequence encoding the CH or CL of the human antibody can be commercially available. The constructed expression vector is introduced into a host cell to obtain a recombinant cell that expresses a chimeric antibody. Then, the recombinant cell is cultured to obtain a desired chimeric antibody from the culture supernatant.

Chimeric antibodies having the VH and VL identified in (C2) to (C11) above can also be constructed and produced by the same method.

<Method for Producing Multispecific Antibody>

As a method for producing a multispecific antibody, for example, the anti-human LPA1 antibody according to the present disclosure or a fragment thereof is linked with another antibody or a fragment thereof. As another example, the anti-human LPA1 antibody according to the present disclosure or a fragment thereof and another antibody or a fragment thereof are co-expressed in a host cell. Examples of other linking methods include chemical coupling, gene fusion, and non-covalent association.

Examples of practically used multispecific antibodies (bispecific antibodies) include BLINCYTO® that binds to CD3 and CD19. Other examples include HEMLIBRA® that binds to coagulation factor IXa and coagulation factor X. The techniques for producing multispecific antibodies are known in the art, and these known production techniques can also be applied to the anti-human LPA1 antibody according to the present disclosure.

<Purification Method>

The method for purifying the above antibodies is not particularly limited, and any known method can be used. For example, a culture supernatant of the above recombinant cell can be collected to purify the above antibodies by combining known methods such as various types of chromatography, salt precipitation, dialysis, and membrane separation. If the isotype of the antibody is IgG, the antibody can also be easily purified by affinity chromatography using protein A.

<Modified Antibody>

The antibodies according to the present disclosure may be modified antibodies bonded with other molecules. Examples of other molecules include peptides, proteins, low molecular weight compounds, radioisotopes, and light absorbers. Examples of the method for bonding the antibodies with other molecules include chemical coupling, gene fusion, and non-covalent association. If other molecules to be bonded are antibodies, the modified antibodies can be multispecific antibodies. In this regard, multispecific antibodies can be regarded as a type of modified antibodies.

In a preferable embodiment, the above modified antibodies are antibody drug conjugates (ADC). Examples of the drug to be conjugated include anti-fibrosis agents; low molecular weight anticancer drugs (cytotoxins, chemotherapeutic drugs); biologically active proteins or polypeptides such as cytokines; radioisotopes; and light absorbers. These drugs can be conjugated with the antibodies directly or indirectly via linkers or chelating agents to produce antibody drug conjugates.

Examples of practically used antibody drug conjugates include: ENHERTZ® containing trastuzumab bonded with a camptothecin derivative, as an antibody drug conjugate prepared by conjugation of the antibody with a low molecular weight anticancer drug; ZEVALIN® containing an anti-CD20 monoclonal antibody labeled with yttrium 90 ($^{90}$Y), as an antibody drug conjugate prepared by conjugation of the antibody with a radioisotope; and ACALUX® containing cetuximab bonded with IR Dye 700DX, as an antibody drug conjugate prepared by conjugation of the antibody with a light absorber. The drugs contained in these antibody drug conjugates can also be applied to the anti-human LPA1 antibody according to the present disclosure. Furthermore, examples of suitable drugs used for the antibody drug conjugates are known in the art, and these known drugs can also be applied to the anti-human LPA1 antibody according to the present disclosure.

<Medicament>

The present disclosure encompasses a medicament containing the above antibody as an active ingredient. The medicament may be a pharmaceutical composition containing the above antibody and a pharmaceutically acceptable carrier. Preferably, the medicament blocks the LPA1-dependent cell functions.

In a preferable embodiment, the above medicament is used for treating a disease, a disorder, or a symptom, causally involving the LPA1-dependent cell dysfunction. Examples of the disease, the disorder, or the symptom, causally involving the LPA1-dependent cell dysfunction include fibroses selected from a group consisting of hepatic fibrosis, kidney fibrosis, pulmonary fibrosis, skin fibrosis, cardiovascular fibrosis, gastrointestinal fibrosis, and other fibrous diseases.

Examples of the liver fibrosis include fibrosis selected from a group consisting of nonalcoholic steatohepatitis (NASH), nonalcoholic fatty liver disease (NAFLD), liver cirrhosis, ischemia reperfusion, post liver transplantation disorder, necrotizing hepatitis, hepatitis B, hepatitis C, primary biliary cirrhosis, and primary sclerosing cholangitis. The liver cirrhosis is caused, e.g., by at least one selected from a group consisting of alcoholic induction, drug induction, and chemical induction.

Examples of the kidney fibrosis include fibroses selected from a group consisting of proliferative glomerulonephritis, sclerosing glomerulonephritis, nephrogenic fibrosing dermopathy, diabetic nephropathy, renal tubulointerstitial fibrosis, and focal segmental glomerulosclerosis.

Examples of the pulmonary fibrosis include fibroses selected from a group consisting of lung interstitial fibrosis, drug-induced sarcoidosis, pulmonary fibrosis, idiopathic pulmonary fibrosis, asthma, chronic obstructive lung disease, diffuse alveolar damage disease, pulmonary hypertension, and neonatal bronchopulmonary malformation.

Examples of the skin fibrosis include fibroses selected from a group consisting of scleroderma, keloid scarring, psoriasis, hypertrophic scarring, and pseudo-scleroderma.

Examples of the cardiovascular fibrosis include fibroses selected from a group consisting of atherosclerosis, coronary artery restenosis, congestive cardiomyopathy, heart failure, heart transplantation, and myocardial fibrosis.

Examples of the gastrointestinal fibrosis include fibroses selected from a group consisting of collagenous colitis, villous atrophy, crypt hyperplasia, polyp formation, Crohn's fibrosis, gastric ulcer healing, or scar after abdominal adhesion surgery.

The fibrosis may be caused by a bone-related fiberization disease and have rheumatoid pannus formation.

Other examples of the disease, the disorder, and the symptom, causally involving the LPA1-dependent cell dysfunction include cell proliferative diseases such as hematological cancer and solid carcinoma (tumor cell proliferation, tumor infiltration and metastasis, and controlled angiogenesis).

Examples of the hematological cancer include hematological cancers selected from a group consisting of acute myeloid leukemia, acute lymphoblastic leukemia, chronic myeloid leukemia, chronic lymphocytic leukemia, and non-Hodgkin's lymphoma.

Examples of the solid carcinoma include solid carcinomas selected from a group consisting of breast cancer, malignant breast tumor, gastric cancer, melanoma, non-small-cell lung cancer, pulmonary adenocarcinoma, gastric cancer, pancreatic cancer, ovarian cancer, uterine cancer, cervical cancer, hepatoma, prostate cancer, urothelial cancer, renal cell cancer, and various squamous cell cancers. Examples of the squamous cell cancer include squamous cell cancers selected from a group consisting of oral squamous cell carcinoma, esophageal squamous cell carcinoma, and pharyngeal squamous cell carcinoma.

Other examples of the disease, the disorder, or the symptom, causally involving the LPA1-dependent cell dysfunction include: pains including fibromyalgia, cancer pain, and diabetic neuropathy; inflammatory diseases and autoimmune disease, including rheumatoid arthritis, sepsis, chronic obstructive lung disease, inflammatory bowel disease, implanted organ rejection, Guillain-Barre syndrome, and multiple sclerosis; metabolic diseases including obesity and insulin-resistant diabetes; cardiovascular disorders including stroke, hypertensive nephropathy, and Raynaud's phenomenon; nervous system disorders including hydrocephalus, schizophrenia, depression, and dementia; urologic diseases including prostatic hyperplasia and urinary incontinence; and ophthalmological diseases including ischemic retinopathy, diabetic retinopathy, and age-related macular degeneration.

<Administration Method>

The above medicament can be administered orally or parenterally, and systemically or locally. Examples of the dosage forms include an injection dosage form, a transnasal dosage form, a transpulmonary dosage form, and a transdermal dosage form. In the case of the injection dosage form, the medicament can be administered systemically or locally, e.g., by intravenous injection, intramuscular injection, intraperitoneal injection, subcutaneous injection, or the like. The administration method can be selected as appropriate depending on age and symptoms of a patient. A dose of the above antibodies can be selected within a range of 0.0001 mg to 1000 mg per kilogram of body weight. Alternatively, for example, the dose can be selected within a range of 0.001 to 100,000 mg/body weight. However, the dose of the antibodies is not limited to these ranges.

<Formulation>

The above medicament can be formulated according to an ordinary method (e.g., Remington's Pharmaceutical Science, latest edition, Mark Publishing Company, Easton, U.S.A.). The medicament can contain pharmaceutically acceptable carriers or additives. Examples of the carriers or the additives include, but are not limited to, surfactants (e.g., polyethylene glycol (PEG), Tween), excipients, antioxidants (e.g., ascorbic acid), colorants, fragrant agents, preservatives, stabilizers, buffers (e.g., phosphoric acid, citric acid, other organic acids), chelating agents (e.g., ethylene diamine tetra acetic acid (EDTA)), suspensions, isotonizing agents, binders, disintegrators, lubricants, fluidity accelerators, and flavoring agents, and other commonly used carriers or the like can be used as appropriate. Specific examples of the carriers or the additives include light anhydrous silicic acid, lactose, crystalline cellulose, mannitol, starch, carmellose calcium, carmellose sodium, hydroxypropyl cellulose, hydroxypropylmethyl cellulose, polyvinylacetal diethylaminoacetate, polyvinylpyrrolidone, gelatin, medium-chain fatty acid triglyceride, polyoxyethylene hardened castor oil 60, saccharose, carboxymethyl cellulose, corn starch, and inorganic salts. The medicament may contain other low molecular weight polypeptides; proteins such as serum albumin, gelatin, and immunoglobulin; and amino acids such as glycine, glutamine, asparagine, arginine, and lysine.

When the medicament is in an aqueous solution for injection, the medicament may be saline, an isotonic solution containing glucose or other auxiliary agents, such as D-sorbitol, D-mannose, D-mannitol, sodium chloride, and they may be used in combination with an appropriate solubilizer, e.g., an alcohol (e.g., ethanol), a polyalcohol (e.g., propylene glycol, PEG), a nonionic surfactant (polysorbate 80, HCO-50), or the like. If necessary, the above antibodies can be encapsulated in microcapsules (e.g., made of hydroxymethyl cellulose, gelatin, poly[methyl methacrylate]) or can be configured as a colloidal drug delivery system (e.g., liposomes, albumin microspheres, microemulsions, nanoparticles, and nanocapsules (e.g., see "Remington's Pharmaceutical Science 16th edition", Oslo Ed., 1980).

Furthermore, techniques for sustained release of drugs are known and can be applied to the above medicament (Langer et. al., J. Biomed. Master. Res. 15: 162-277 (1981); Langer, Chem. Tech. 12: 9 (8-105) (1982); U.S. Pat. No. 3,773,919; EP Patent No. 58,481; Sidman et. al., Biopolymers 22: 547-556 (1983); EP Patent No. 133,988).

<Application for Gene Therapy>

The above nucleic acid may be incorporated into a gene therapy vector or an mRNA that can be translated into a protein in vivo, to prepare a gene therapeutic drug. Examples of the method for administering the gene therapeutic drug (recombinant vector) include a direct administration method using naked plasmids, as well as a method in which the drug is packed into liposomes or the like for administration, a method in which the drug is incorporated into various virus vectors such as retrovirus vectors, adenovirus vectors, vaccinia virus vectors, poxvirus vectors, adeno-associated virus vectors, and hemagglutinating virus of Japan (HVJ) vectors (see Adolph, "Viral Genome Methods", CRC Press, Florid (1996)), and a method in which the drug is applied on bead carriers such as colloidal gold particles for administration (e.g., WO 93/17706).

The gene therapeutic drug may be administered by any method as long as the antibodies are expressed in vivo and can exert their effects. Preferably, a sufficient amount of the drug is administered through an appropriate parenteral route, such as intravenous route, intraperitoneal route, subcutaneous route, intradermal route, intra-adipose route, intramammary route, inhalation route, intramuscular route, or the like by a method using injection, infusion, gas inductive particle bombardment (using e.g., an electron gun), mucosal route using collunarium or the like. Furthermore, the gene therapeutic drug may be administered ex vivo by a process in which the drug is introduced into cells using liposome transfection, particle bombardment (U.S. Pat. No. 4,945, 050), or viral infection, and the cells are reintroduced into the animal.

Furthermore, the present disclosure also includes a treatment method and a therapeutic drug regarding a disease of a mammal suffering from a disease or an illness caused by an LPA1-dependent abnormal cell hyperfunction.

Herein, "treatment" means prevention or alleviation of progression and exacerbation of a disease symptom in a mammal that is at risk of suffering from or has suffered from the disease. Thereby, the "treatment" is used as a mean of a therapeutic treatment aimed to prevent or alleviate progression and exacerbation of various symptoms and the like of the disease.

The term "disease" refers to all diseases that develop due to the LPA1-dependent abnormal cell hyperfunction, and conceptually includes, but is not limited to, hepatic fibrosis, kidney fibrosis, pulmonary fibrosis, skin fibrosis, cardiovascular fibrosis, gastrointestinal fibrosis, and other fibrosis diseases, as well as hematological cancer, solid carcinoma, pain, inflammatory diseases, autoimmune diseases, metabolic diseases, cardiovascular disorders, nervous system disorders, urologic diseases, and ophthalmological diseases.

The "mammal" to be treated means any animal classified into mammals, and examples thereof include, but are not limited to, humans, as well as pet animals such as dogs, cats, and rabbits, and domestic animals such as cattle, pigs, sheep, and horses. Humans are particularly preferable "mammals".

<Antibody-Immobilized Carrier>

The present disclosure encompasses a carrier to which the above antibodies are immobilized (antibody-immobilized carrier). In a preferable embodiment, the antibody-immobilized carrier is used to remove LPA1-expressing cells from a body fluid by bringing the carrier into contact with the body fluid containing the LPA1-expressing cells. Examples of the body fluid include blood. Only one type or two or more types of the antibodies may be immobilized to the carrier.

As a specific form of the antibody-immobilized carrier according to the present disclosure, the antibodies are immobilized to a water-insoluble carrier, which is charged into a container. Any material can be used as the water-insoluble carrier, but examples of the material suitable in terms of formability, sterility, and low cytotoxicity include: synthetic polymers such as polyethylene, polypropylene, polystyrene, acrylic resin, nylon, polyester, polycarbonate, polyacrylamide, and polyurethane; natural polymers such as agarose, cellulose, cellulose acetate, chitin, chitosan, and alginate; inorganic materials such as hydroxyapatite, glass, alumina, and titania; and metal materials such as stainless steel and titanium.

Examples of the shape of the carrier include granular shape, cotton shape, woven fabric shape, non-woven fabric shape, sponge-like porous shape, and flat plate shape, but granular shape, cotton shape, woven fabric shape, non-woven fabric shape, sponge-like porous shape are preferable in that these materials have a large surface area per volume. For example, peripheral blood can be passed through a porous filter prepared by previously charging an antibody-immobilized water-insoluble carrier into a container, to efficiently remove disease-related LPA1-expressing cells.

An LPA1-expressing cell removal kit can be prepared by combining the antibody-immobilized carrier according to the present disclosure with other components. Examples of the other components include an anticoagulant, and an extracorporeal circulation circuit.

<Other Disclosures>

The present disclosure encompasses a method for treating a disease, disorder, or symptom, including administering an effective amount of the above antibodies to a patient suffering from the disease, disorder, or symptom involving an LPA1-dependent cell dysfunction. The present disclosure encompasses the above antibodies for use in treating a disease, disorder, or symptom involving an LPA1-dependent cell dysfunction. The present disclosure encompasses use of the above antibodies for the manufacture of a medicament for the treatment of a disease, disorder, or symptom involving an LPA1-dependent cell dysfunction. The aforementioned diseases, disorders, or symptoms include at least tissue fibrosis, cell proliferative disease, pain, inflammatory disease, autoimmune disease, metabolic disease, cardiovascular disorder, urologic disease, or ophthalmological disease.

EXAMPLES

[Example 1] Mouse Immunization for Preparation of Anti-LPA1 Antibody (1) Construction of LPA1-GroEL Subunit Fusion Protein-Expressing Gene Immunization Vector An artificial gene added with a GCTAGC sequence at the 5' end and a GTCGAC sequence at the 3' end was synthesized using, as a base, a human LPA1 (NP_001392, SEQ ID NO: 111) that had been registered in National Center for Biotechnology Information (NCBI) GenBank. This artificial gene was introduced into a cloning vector, and then the resulting vector was cleaved at NheI and Sal sites to prepare DNA fragments. pCI-hCCR7 GroEL (described in WO 2012/043533 and JP Patent No. 5315495) was digested with restriction enzymes NheI and Sal, into which the prepared DNA fragments were inserted, to construct an immunization vector pCI-hLPA1 GroEL. This vector expresses a fusion protein of the human LPA1 and GroEL.

Instead of the human LPA1, a mouse LPA1 (NP_034466, SEQ ID NO: 112) was subjected to the same procedure to construct an immunization vector pCI-mLPA1 GroEL. This vector expresses a fusion protein of the mouse LPA1 and GroEL.

(2) DNA Immunization

The vector pCI-hLPA1 GroEL or pCI-mLPA1 GroEL was dissolved at a concentration of 2 mg/mL in phosphate-buffered saline (PBS) to prepare an immunization composition. 8-week-old mice of various strains were immunized by dosing 25 μL of this immunization composition to each thigh muscle of all legs using in vivo electroporation (Day 0). Thus, the both legs were dosed with 50 g each of pCI-hLPA1 GroEL or pCI-mLPA1 GroEL, i.e. one mouse was immunized with 100 g of DNA per one intervention. Subsequently, the same DNA immunization was performed on day 14, day 28, day 42, and day 56. Furthermore, blood samples were collected before the immunization and 21, 35, and 63 days after the immunization, to prepare serum.

(3) Preparation of LPA1-Stably Expressing Cell

An artificial gene was synthesized using, as a base, a human LPA1 (NP_001392, SEQ ID NO: 111) that had been registered in NCBI gene bank, and introduced into a pCIneo vector (Promega), to construct pCIneo-hLPA1. pCIneo-hLPA1 was introduced into CHO-K1 cell using Lipofectamine 2000 (Thermo Fisher Scientific, Inc.). The resulting cells were cultured in a culture medium containing G418 (Promega) to clone G418-resistant cells that stably expressed human LPA1 (hereinafter referred to as "human LPA1-stably expressing CHO cells").

An artificial gene was synthesized using, as a base, a mouse LPA1 (NP_034466, SEQ ID NO: 112) that had been registered in NCBI gene bank, and introduced into pEF5/FRT/V5-DEST (Thermo Fisher Scientific, Inc.) to construct pEF-FRT-mLPA1. pEF-FRT-mLPA1 and pOG44 plasmid (Thermo Fisher Scientific, Inc.) were simultaneously introduced into Flp-In-CHO cell (Thermo Fisher Scientific, Inc.) using Lipofectamine 2000. The resulting cell was cultured in a culture medium containing hygromycin (Thermo Fisher Scientific, Inc.) to clone a hygromycin-resistant cell that stably expressed mouse LPA1 (hereinafter referred to as "mouse LPA1-stably expressing CHO cells").

(4) Evaluation for Binding Property of Serum Antibody to Human LPA1 and Mouse LPA1 by Flow Cytometry The human LPA1-stably expressing CHO cell, mouse LPA1-stably-expressing CHO cell, and a CHO-K1 cell or CHO-FlpIn cell (hereinafter referred to as "negative control cell") were washed with a fluorescence-activated cell sorting (FACS) buffer (PBS containing 1% of fetal bovine serum (FBS)), to which Fc Block (Cytek Biosciences, Inc.) was added in an amount of 1/500 of the cell suspension to block the cells at 4° C. for 30 minutes. After the blocking, each cell was incubated with 50 time-diluted pre- and post-immunization serums. Furthermore, each cell was washed with FACS buffer, to which a phycoerythrin-labeled anti-mouse IgG antibody (SouthernBiotech) was added as a secondary antibody. Then, the binding of the anti-human LPA1 anti-body and anti-mouse LPA1 antibody in serum to each cell was evaluated using a flow cytometer iQue (Sartorius AG). The serum after the immunization contained antibodies that bound to the human LPA1-stably expressing CHO cell or the mouse LPA1-stably expressing CHO cell but did not bind to the negative control cells. Individuals with increased specific antibody titers against LPA1 were boosted and sampled.

(5) Boosting Using Transient Expression Cell and Sampling

HEK293FT cell (Thermo Fisher Scientific, Inc.) was transfected with the vector pCI-hLPA1 or pCI-mLPA1 using Lipofectamine 2000 to transiently express human LPA1 or mouse LPA1. This cell was injected into spleen and abdominal cavities of individuals with an increased antibody titer, and 3 days later, spleen, inguinal lymph node, and iliac lymph node were sampled. Splenocytes and lymph node-derived cells were separated from each tissue sample, then suspended in CELLBANKER 1plus (Nippon Zenyaku Kogyo Co., Ltd.), and stored at −80° C. until sorting of specific antibody-producing lymphocytes.

[Example 2] Preparation of Antibody (1) Selection of Specific Antibody-Producing Lymphocyte Using Microwell The specific antibody-producing lymphocytes were selected using microwells in accordance with a method described in WO 2020/171020 and JP Patent No. 6881801. That means, the human LPA1-stably expressing CHO cell or the mouse LPA1-stably expressing CHO cell was respectively suspended in F-12 culture medium (10% FBS, containing Penicillin/Streptomycin) to prepare a cell suspension at $3.5 \times 10^5$ cells/500 µL. The cell suspension was put into a microchamber (AS ONE Corporation.) for cell picking systems. The microchamber was subjected to centrifugation at 300 rpm for 1 minute five times to prepare the suspension such that one or two human LPA1-stably expressing CHO cells or mouse LPA1-stably expressing CHO cells were contained in each microwell. The micro chamber was washed with F-12 culture medium, to which 500 µL of F-12 culture medium was added, which was incubated in a $CO_2$ incubator at 37° C. for 1 h so that the human LPA1-stably expressing CHO cell or the mouse LPA1-stably expressing CHO cell adhered to bottom faces of the microwells. To the microwells, CytoRed solution (Dojin Molecular Technologies, Inc.) in a concentration adjusted to 10 nM by F-12 culture medium was added, which was incubated at 37° C. for another 1 hour to stain the CHO cells. The microchamber was washed with F-12 culture medium three times to remove excess CytoRed, and then 1 mL of F-12 medium was charged into the microchamber.

Antibody-producing cells were concentrated from the cells collected in Example 1 (5) after the DNA immunization using EasySep Mouse Biotin Positive Selection Kit (STEMCELL Technologies). In 500 µL of F-12 culture medium, $1.1 \times 10^5$ antibody-producing cells were suspended and charged into a microchamber. The microchamber was subjected to centrifugation at 300 rpm for 1 minute five times to prepare the suspension such that one or two antibody-producing cells were contained in each microwell. The micro chamber was washed with the culture medium, to which an appropriate amount of culture medium was added, which was incubated at 37° C. for 30 minutes to secrete antibodies from the antibody producing cells. The microwells were washed to remove the supernatant, to which Alexa Fluor 488-labeled anti-mouse IgG antibody (Abcam) diluted by 500 times in RPMI 1640 (containing 10% FBS) was added and incubated at 37° C. for 30 minutes. The microwells were washed with RPMI 1640 (phenol red-free, containing 1% FBS) three times, to which 1 mL of RPMI1640 was added. The microchamber was set to a cell picking system (AS ONE Corporation.) to acquire information on a transmitted light image and two fluorescence images of all microwells. Fluorescence of CytoRed was detected at an excitation wavelength of 543 nm and a fluorescent wavelength of 593 nm. Fluorescence of Alexa Fluor 488 was detected at an excitation wavelength of 482 nm and a fluorescent wavelength of 536 nm. From microwells that could be determined to have antibodies binding to the surfaces of the human LPA1-stably expressing CHO cells or mouse LPA1-stably expressing CHO cells based on scan images of transmitted light, CytoRed, and Alexa Fluor 488, antibody-producing cells were collected in the cell lysate using a capillary with a diameter of several m to several tens of m (AS ONE Corporation.)

(2) Isolation of Antibody Gene from Collected Antibody-Producing Cell

An antibody gene was obtained from the antibody producing cells by MAGrahd method (Kurosawa N, Yoshioka M, Fujimoto R, Yamagishi F, Isobe M. "Rapid production of antigen-specific monoclonal antibodies from a variety of animals", BMC Biol. 2012; 10: 80). In other words, a cell-derived mRNA was captured on an oligo dT magnet by mixing 5 µL of cell lysate collected in (1) with 5 g of oligo dT magnet. The oligo dT magnet was washed with a washing solution using MAGrahd reactor tray and neodymium magnet, and then a cDNA was synthesized by a reverse transcription reaction. The magnet was further washed, and then a 5'-terminal translational reaction was performed. Using the synthesized cDNA, genes on the antibody heavy chain variable region (VH region) and genes on the antibody light chain variable region (VL region) were isolated and amplified by 5' racePCR. In order to enhance the specificity of the amplified product, PCR was repeated twice. In the first PCR, a first forward primer (SEQ ID NO: 113) that amplified the VH and VL regions in common, a VH first reverse primer (SEQ ID NO: 114) that specifically amplified the VH region, and a VL first reverse primer (SEQ ID NO: 115) that specifically amplified the VL region were mixed and used. In the second PCR, the amplified product in the first PCR was used as a template, and, for amplification of the VH region, a second forward primer (SEQ ID NO: 116) and a VH second reverse primer (SEQ ID NO: 117) that specifically amplified the VH region were used as primers, and for amplification of the VL region, a second forward primer (SEQ ID NO: 116) and a VL second reverse primer (SEQ ID NO: 118) that specifically amplified the VL region were used as primers. As a result of an agarose gel electrophoresis for the sample after the second PCR, a gene amplified product corresponding to the VH region was found at a position of approximately 750 bp, and a gene amplified product corresponding to the VL region was found at a position of approximately 550 bp.

(3) Construction of Antibody Expression Unit

An antibody expression unit was constructed by TS-jPCR method (Yoshioka M, Kurosawa N, Isobe M. "Target-selective joint polymerase chain reaction: a robust and rapid method for high-throughput production of recombinant monoclonal antibodies from single cells.", BMC Biotechnol., 2011; 11: 75). That means, the VH region gene amplified in (2), an antibody heavy chain constant region gene, and a gene including a promoter region necessary for gene expression were fused by PCR to construct an antibody expression unit that expressed a full-length antibody heavy chain. Similarly, the VL region gene amplified in (2), an antibody light chain constant region gene, and a gene including a promoter region necessary for gene expression were fused by PCR to construct an antibody expression unit that expressed a full-length antibody light chain.

(4) Introduction of Antibody Expression Unit into Mammalian Cell

Expi293F cells (Thermo Fisher Scientific, Inc.) were seeded to a cell culture 6-well plate at $7.5 \times 10^6$ cells/3 mL/well. Two types, heavy and light chain antibody expression units constructed in (3) were co-introduced into Expi293F cells using Expifectamine 293 Reagent (Thermo Fisher Scientific, Inc.). On day 5 after the introduction, a cell supernatant was collected and used to evaluate the binding properties of the produced antibodies.

(5) Evaluation for Binding Property of Antibody Using Flow Cytometry

The human LPA1-stably expressing CHO cell or mouse LPA1-stably expressing CHO cell, and a negative control cell were washed with FACS buffer and suspended in FACS buffer at a cell concentration of $1 \times 10^7$ cells/mL. To this suspension, Fc Block (Cytek Biosciences, Inc.) was added in an amount of $1/500$ of the cell suspension, to block the cells at 4° C. for 30 minutes. After the blocking, the cells were suspended at $2 \times 10^5$ cells/50 µL. This cell suspension was mixed with the cell supernatant collected in (4) and incubated at 4° C. for 1 hour. After the incubation, the cells were washed with 100 µL of FACS buffer twice. As a secondary antibody, a phycoerythrin-labeled anti-mouse IgG antibody (SouthernBiotech) dilution was added to wells at 50 µL/well and incubated at 4° C. for 1 hour. The cells were washed with 100 µL of FACS buffer twice and then suspended in 80 µL of FACS buffer, and a fluorescence intensity of the cell surface was measured using a flow cytometer iQue (Sartorius AG) to evaluate the binding property of the antibodies. An antibody unit that bound to the human LPA1-stably expressing CHO cell or mouse LPA1-stably expressing CHO cell and did not bind to the negative control cell was designated as a primary hit antibody.

[Example 3] Screening of Antibody by Evaluating Inhibition of Intracellular cAMP Signaling A purified antibody was prepared from a culture supernatant corresponding to the primary hit antibody in Example 2 by Protein A affinity purification according to an ordinary method and subjected to the following evaluation. A concentration of intracellular cyclic adenosine monophosphate (cAMP) was measured using LANCE Ultra cAMP Kit (PerkinElmer, Inc.).

The human LPA1-stably expressing CHO cell or mouse LPA1-stably expressing CHO cell was cultured in an FBS-free Ham's F-12 culture medium containing 0.5% of BSA, 100 units/mL of penicillin, and 100 g/mL of streptomycin for 24 hours. The cells were collected from the cell culture dish by an enzyme-free cell dissociation buffer (Thermo Fisher Scientific, Inc.) and washed with Hanks' Balanced Salt Solution (HBSS). The cells were suspended at $2 \times 10^5$ cells/mL in a stimulation buffer (HBSS containing 5 mM of HEPES, 0.5 mM of 3-isobutyl-1-methylxanthine (IBMX), and 0.1% of BSA), and dispensed into OptiPlate-96 well (PerkinElmer, Inc.) at 12.5 µL (2,500 cells)/well. The antibodies diluted to 400 nM in the stimulation buffer was added to the wells at 6.25 L/well (final concentration: 100 nM) and allowed to stand for 15 minutes at room temperature. Subsequently, a mixture of 12 M Forskolin (final concentration: 3 µM) and 200 nM of oleoyl-L-α-lysophosphatidic acid sodium salt (Merck KGaA) (final concentration: 50 nM) was added to wells at 6.25 µL/well, and allowed to stand at room temperature for 30 minutes. An Eu-cAMP tracer solution and a ULight-anti-cAMP antibody solution, which had been diluted in a cAMP Detection Buffer appended to the kit according to the manufacturer's instruction, were added to the wells at 12.5 µL/well respectively, and allowed to stand at room temperature for 1 hour. Then, a time-resolved fluorescence resonance energy transfer (TR-FRET) was measured using a plate reader EnVision 2104 (Perkin-Elmer, Inc.). For an inhibition rate (%), a value measured in adding Forskolin and lysophosphatidic acid was standardized as 0% inhibition rate and a value measured in adding only Forskolin was standardized as 100% inhibition rate, and the inhibition rate was calculated as a relative intracellular cAMP signaling inhibition rate (%).

Among the primary hit antibodies, eleven types of antibodies: 210309-1-C, 210309-1-G, 210309-2-A, 210309-2-D, 210309-4-A, 210310-1-D, 210420-4-E, 210420-1-H, 210420-3-E, 211222-1-G, and 211222-1-A, which inhibited lysophosphatidic acid-induced intracellular cAMP signaling in the human LPA1-expressing cell and mouse LPA1-expressing cell, were selected as antibodies having the activity of blocking the LPA1-dependent cell functions.

Table 1 presents, for the eleven antibodies, antigen types from which the antibodies were obtained, and lysophosphatidic acid-induced intracellular cAMP signaling inhibition rates of the antibodies in the human and mouse LPA1-expressing cells.

TABLE 1

| Antibody | Antigen | Intracellular cAMP signaling inhibition (Inhibition rate %/100 nM) | |
| | | Human LPA1-expressing cell | Mouse LPA1-expressing cell |
| --- | --- | --- | --- |
| 210309-1-C | Human LPA1 | 47 | 20 |
| 210309-1-G | Human LPA1 | 34 | 36 |
| 210309-2-A | Human LPA1 | 32 | 32 |
| 210309-2-D | Human LPA1 | 51 | 53 |
| 210309-4-A | Human LPA1 | 95 | 50 |
| 210310-1-D | Human LPA1 | 22 | 25 |
| 210420-4-E | Mouse LPA1 | 24 | 46 |
| 210420-1-H | Mouse LPA1 | 22 | 37 |
| 210420-3-E | Mouse LPA1 | 44 | 50 |
| 211222-1-G | Human LPA1 | 22 | 49 |
| 211222-1-A | Human LPA1 | 1 | 30 |

[Example 4] Screening of Antibody by Flow Cytometry Evaluation of Binding to Lysophosphatidic Acid Receptor To evaluate the binding specificity of lysophosphatidic acid receptor subtypes to LPA1, LPA2, and LPA3, artificial genes added with a FLAG tag sequence at 5' terminal were synthesized by using, as a base, human LPA1 (SEQ ID NO: 111), mouse LPA1 (SEQ ID NO: 112), as well as human LPA2 (NP_004711, SEQ TD NO: 119), mouse LPA2 (NP_064412, SEQ TD NO: 120), human LPA3 (NP_036284, SEQ ID NO: 121), and mouse LPA3 (NP_075359, SEQ ID NO: 122) which had been registered in Genflank. BTEK293FT cell was transfected with 10 µg of an expression vector carrying each synthetic gene using Lipofectamine 2000, to prepare a human LPA1 gene transfected cell, a mouse LPA1 gene transfected cell, a human LPA2 gene transfected cell, a mouse LPA2 gene transfected cell, a human LPA3 gene transfected cell, and a mouse LPA3 gene transfected cell.

le;3qThe next day, the cells were washed with PBS, then detached from the cell culture dishes by an enzyme-free cell dissociation buffer (Thermo Fisher Scientific, Inc.), then washed with PBS, and then collected by centrifugation. Goat serum (Thermo Fisher Scientific, Inc.) was diluted by 2 times in FACS buffer (PBS containing 1% o of FBS), into which the cells were suspended at $1 \times 10^7$ cells/mL. This suspension was allowed to stand at 4° C. for 30 minutes to block the cells. The cells were collected by centrifugation and suspended in FACS buffer at $4 \times 10^6$ cells/mL, and this suspension was dispensed into a V-bottom 96-well plate (Thermo Fisher Scientific, Inc.) at 25 µL ($1 \times 10^5$ cells)/well.

To the plate, 25 g/mL of eleven types of antibodies selected in Example 3 (210309-1-C, 210309-1-G, 210309-2-A, 210309-2-D, 210309-4-A, 210310-1-D, 210420-4-E, 210420-1-H, 210420-3-E, 211222-1-G, 211222-1-A), 20 g/mL of anti-FLAG mouse IgG antibody (Sigma-Aldrich Co. LLC) or mouse isotype control antibody (Fujifilm Wako Pure Chemicals Corporation) were added at 25 L/well, and allowed to stand at 4° C. for 1 hour. The cells were collected by centrifugation and washed with 120 µL of FACS buffer. This washing operation was repeated twice. To the cell sediment, 25 µL each of Goat Anti-Mouse IgG H&L (DyLight 650) (Abcam) that was a secondary antibody diluted by 500 times in FACS buffer was dispensed, then suspended, and then allowed to stand at 4° C. for 1 hour. The cells were washed twice, then suspended in 50 µL of FACS buffer, and the whole content thereof was transferred to a V-bottom 96-well plate (Greiner), to measure the binding of antibodies to the cells using a flow cytometer (Agilent Novocyte).

Figure 1B:
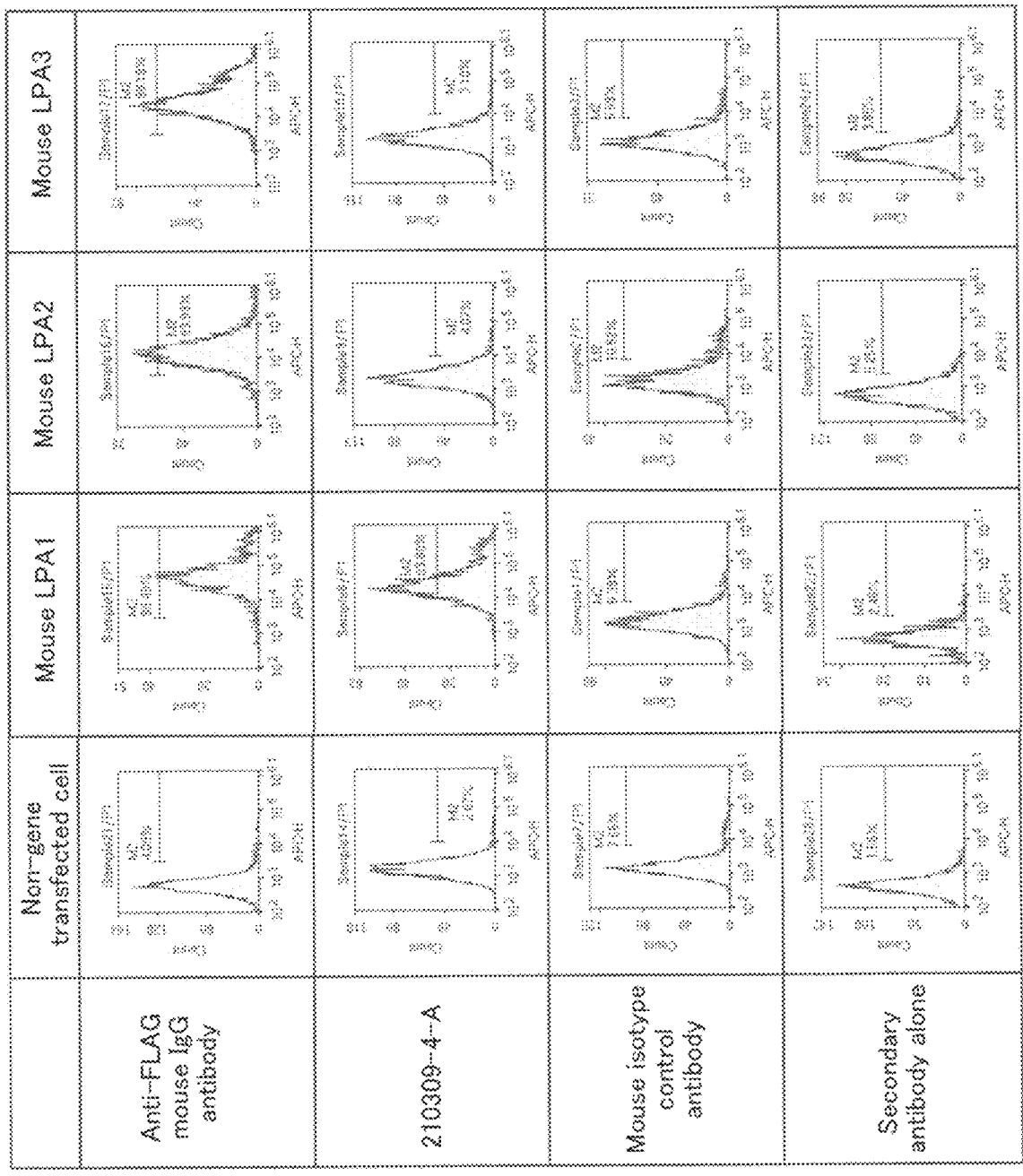
FIG. 1B is a histogram presenting results of flow cytometry performed in Example 4, showing binding properties between an antibody and mouse LPA1 to LPA3.
Figure 2A:
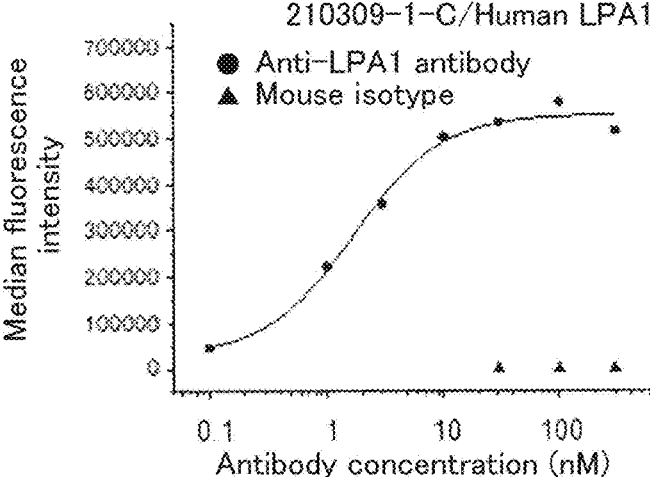
FIG. 2A is a graph presenting an evaluation result of a binding property of an antibody (210309-1-C) to a human LPA1-stably expressing CHO cell.
Figure 2B:
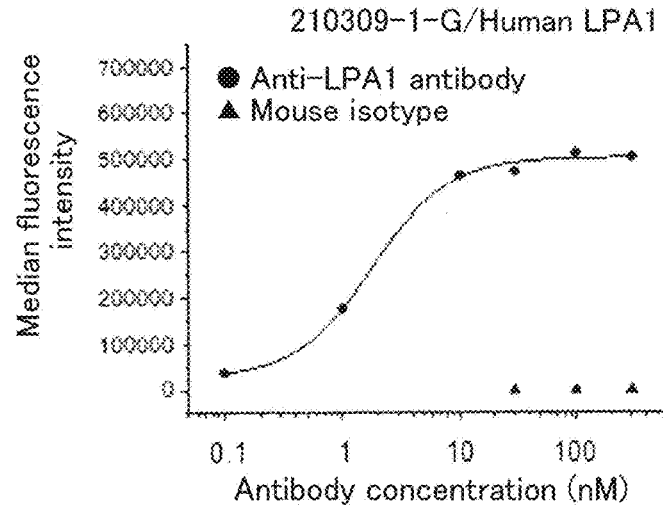
FIG. 2B is a graph presenting an evaluation result of a binding property of an antibody (210309-1-G) to a human LPA1-stably expressing CHO cell.
Figure 2C:
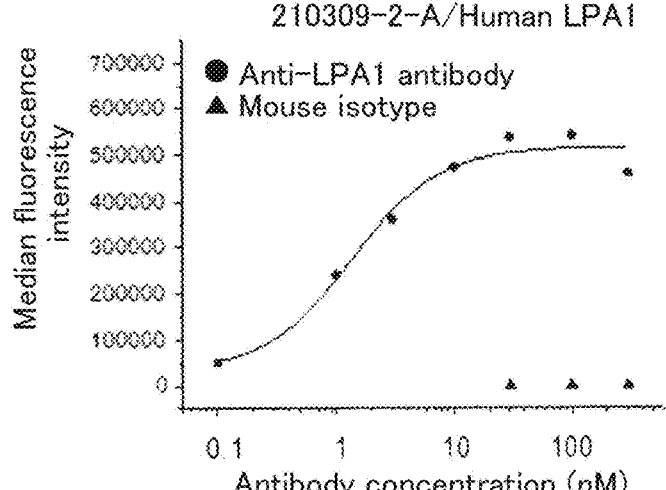
FIG. 2C is a graph presenting an evaluation result of a binding property of an antibody (210309-2-A) to a human LPA1-stably expressing CHO cell.
Figure 2D:
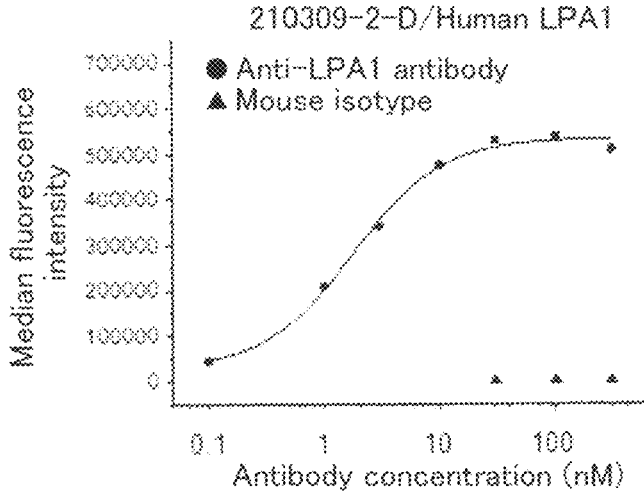
FIG. 2D is a graph presenting an evaluation result of a binding property of an antibody (210309-2-D) to a human LPA1-stably expressing CHO cell.
Figure 2E:
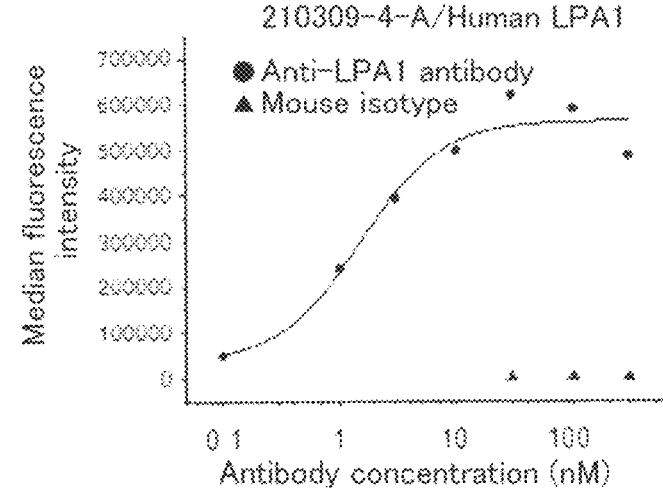
FIG. 2E is a graph presenting an evaluation result of a binding property of an antibody (210309-4-A) to a human LPA1-stably expressing CHO cell.
Figure 2F:
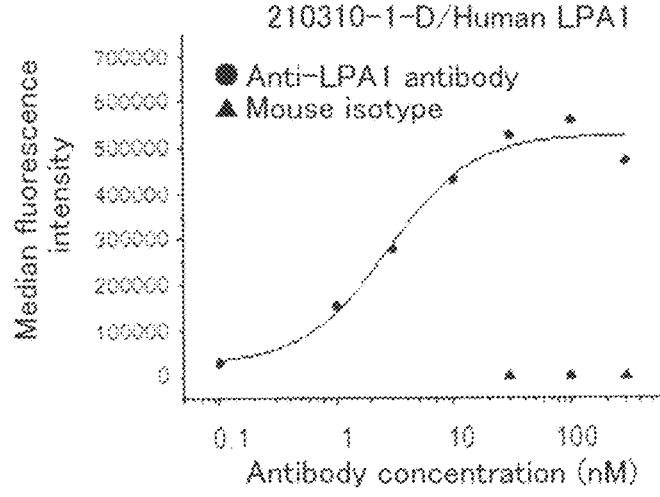
FIG. 2F is a graph presenting an evaluation result of a binding property of an antibody (210310-1-D) to a human LPA1-stably expressing CHO cell.
Figure 2G:
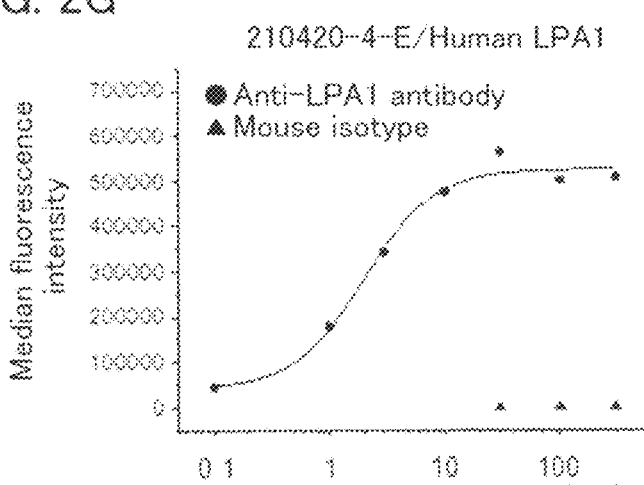
FIG. 2G is a graph presenting an evaluation result of a binding property of an antibody (210420-4-E) to a human LPA1-stably expressing CHO cell.
Figure 2H:
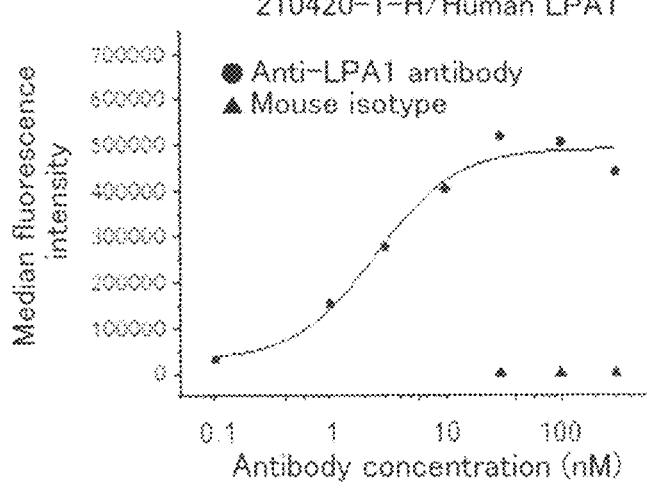
FIG. 2H is a graph presenting an evaluation result of a binding property of an antibody (210420-1-H) to a human LPA1-stably expressing CHO cell.
Figure 2I:
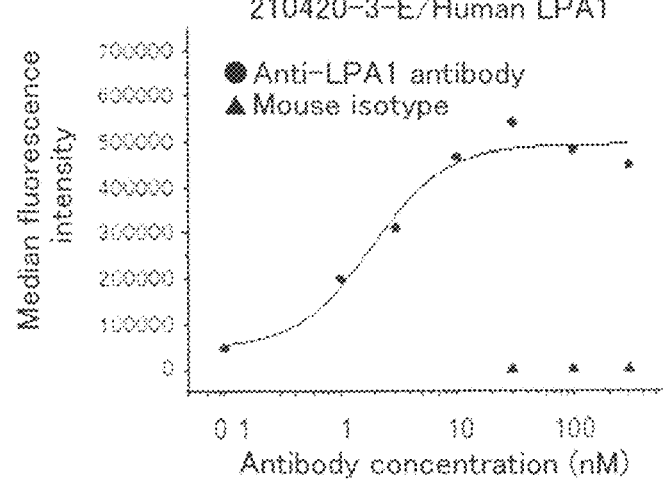
FIG. 2I is a graph presenting an evaluation result of a binding property of an antibody (210420-3-E) to a human LPA1-stably expressing CHO cell.
Figure 2J:
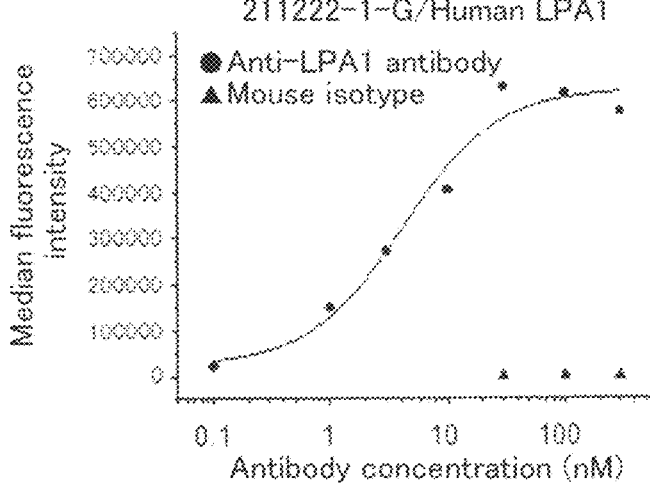
FIG. 2J is a graph presenting an evaluation result of a binding property of an antibody (211222-1-G) to a human LPA1-stably expressing CHO cell.
Figure 2K:
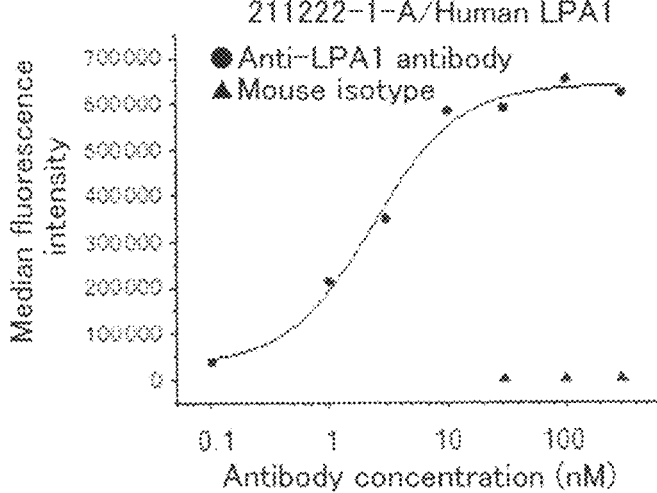
FIG. 2K is a graph presenting an evaluation result of a binding property of an antibody (211222-1-A) to a human LPA1-stably expressing CHO cell.
Figure 3A:
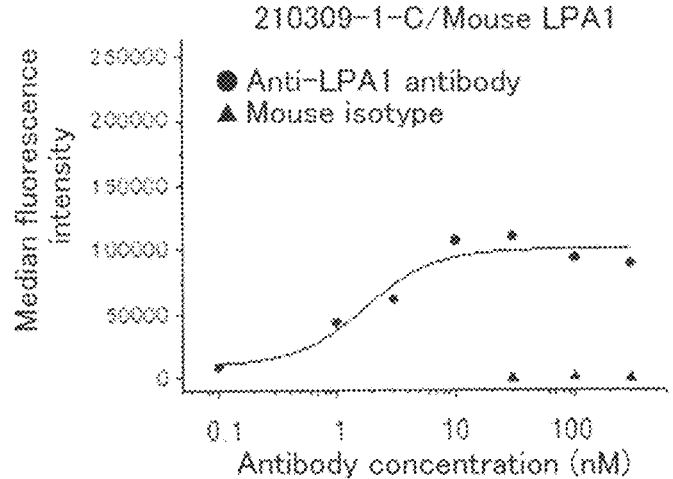
FIG. 3A is a graph presenting an evaluation result of a binding property of an antibody (210309-1-C) to a mouse LPA1-stably expressing CHO cell.
Figure 3B:
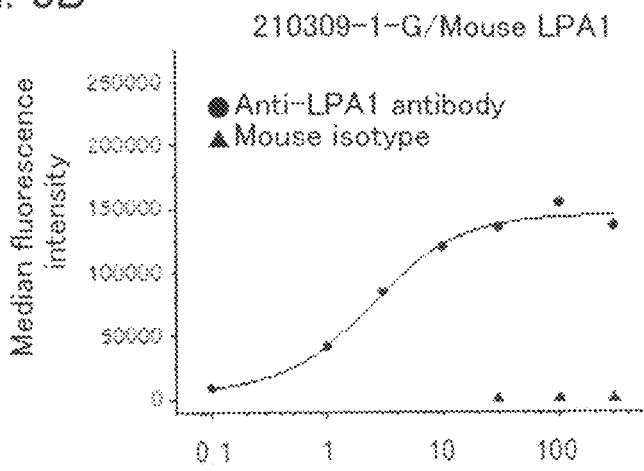
FIG. 3B is a graph presenting an evaluation result of a binding property of an antibody (210309-1-G) to a mouse LPA1-stably expressing CHO cell.
Figure 3C:
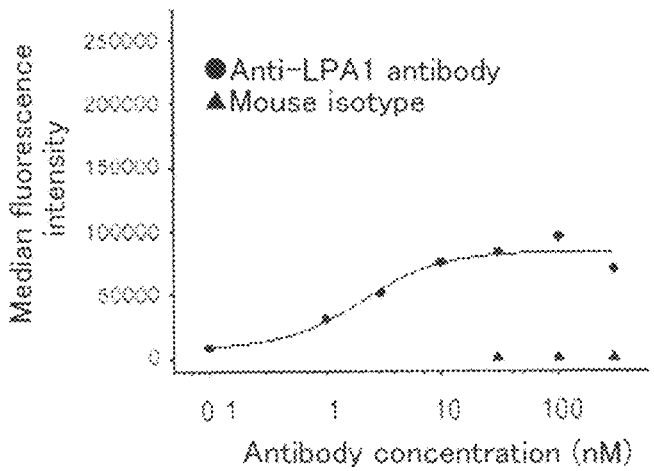
FIG. 3C is a graph presenting an evaluation result of a binding property of an antibody (210309-2-A) to a mouse LPA1-stably expressing CHO cell.
Figure 3D:
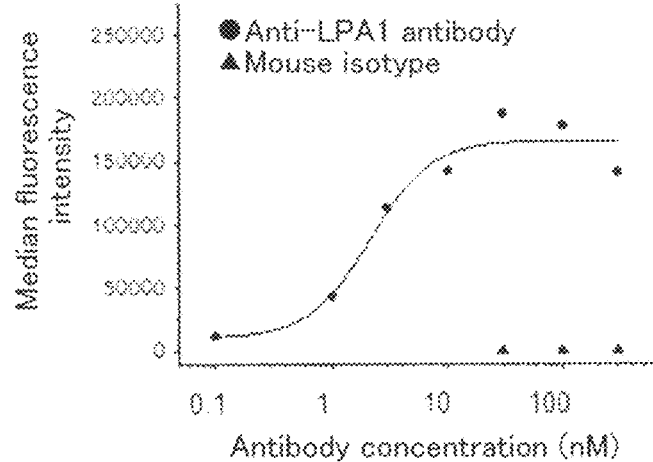
FIG. 3D is a graph presenting an evaluation result of a binding property of an antibody (210309-2-D) to a mouse LPA1-stably expressing CHO cell.
Figure 3E:
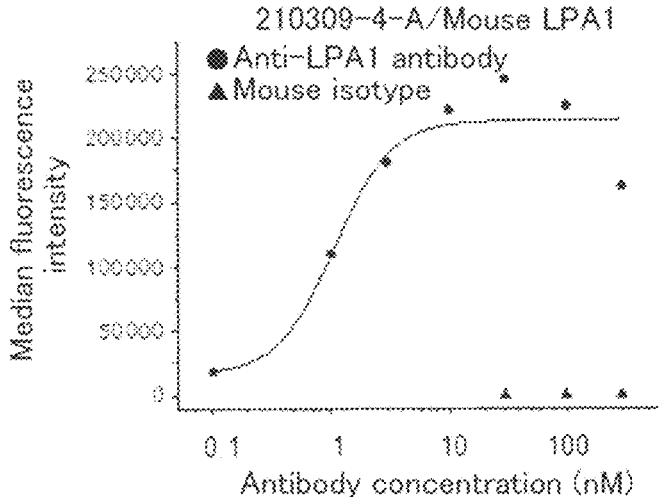
FIG. 3E is a graph presenting an evaluation result of a binding property of an antibody (210309-4-A) to a mouse LPA1-stably expressing CHO cell.
Figure 3F:
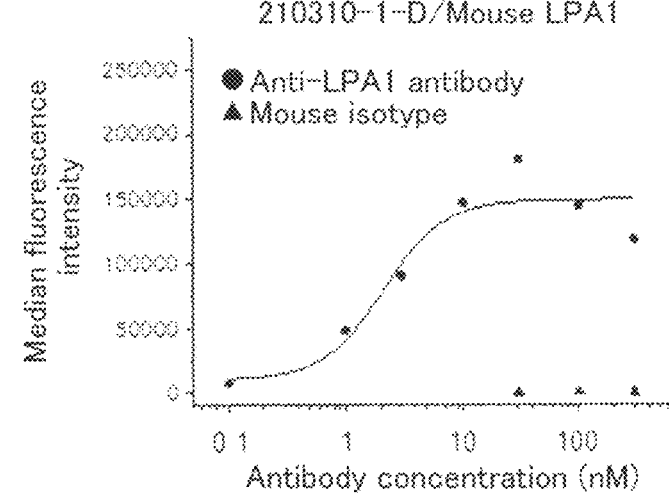
FIG. 3F is a graph presenting an evaluation result of a binding property of an antibody (210310-1-D) to a mouse LPA1-stably expressing CHO cell.
Figure 3G:
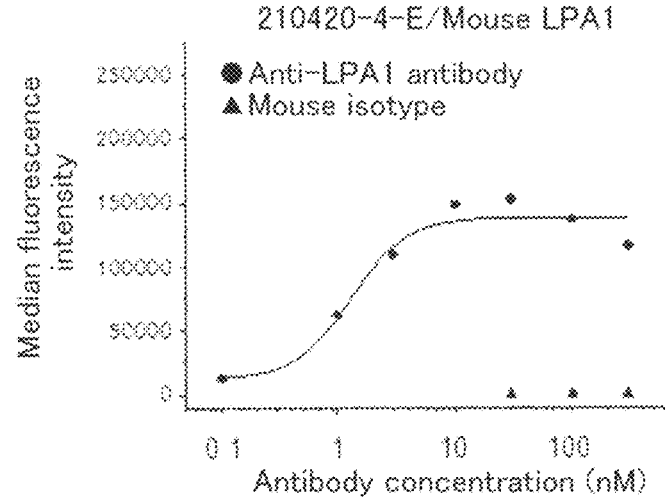
FIG. 3G is a graph presenting an evaluation result of a binding property of an antibody (210420-4-E) to a mouse LPA1-stably expressing CHO cell.
Figure 3H:
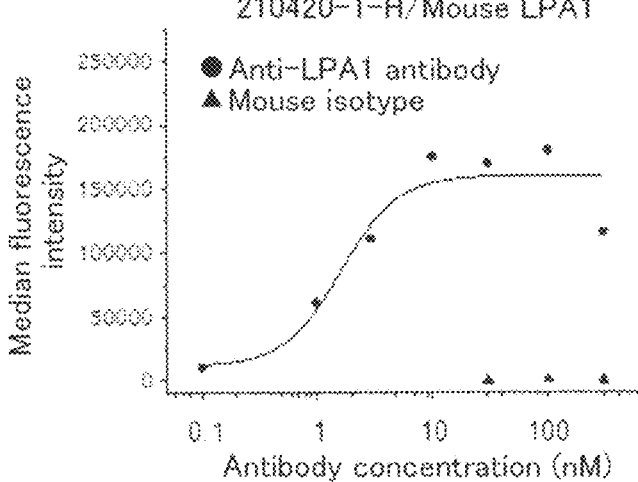
FIG. 3H is a graph presenting an evaluation result of a binding property of an antibody (210420-1-H) to a mouse LPA1-stably expressing CHO cell.
Figure 3I:
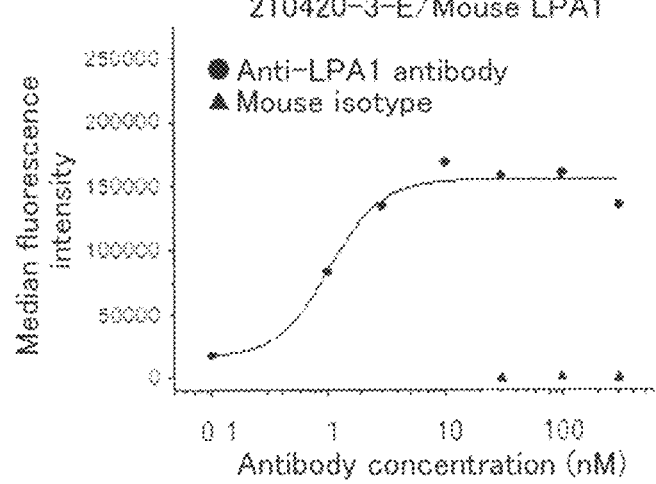
FIG. 3I is a graph presenting an evaluation result of a binding property of an antibody (210420-3-E) to a mouse LPA1-stably expressing CHO cell.
Figure 3J:
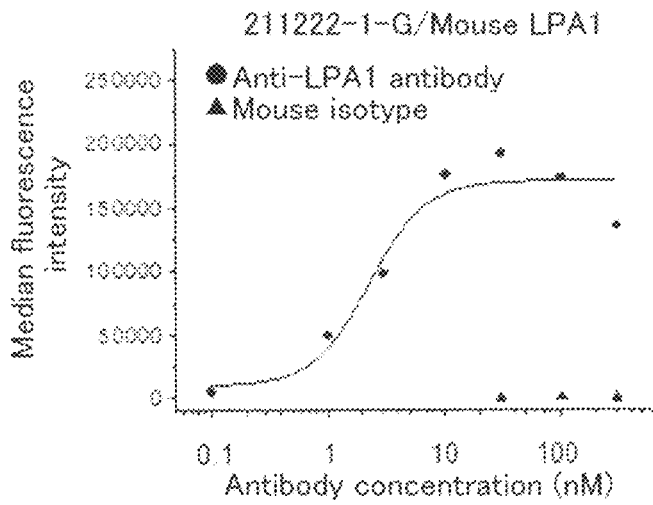
FIG. 3J is a graph presenting an evaluation result of a binding property of an antibody (211222-1-G) to a mouse LPA1-stably expressing CHO cell.
Figure 3K:
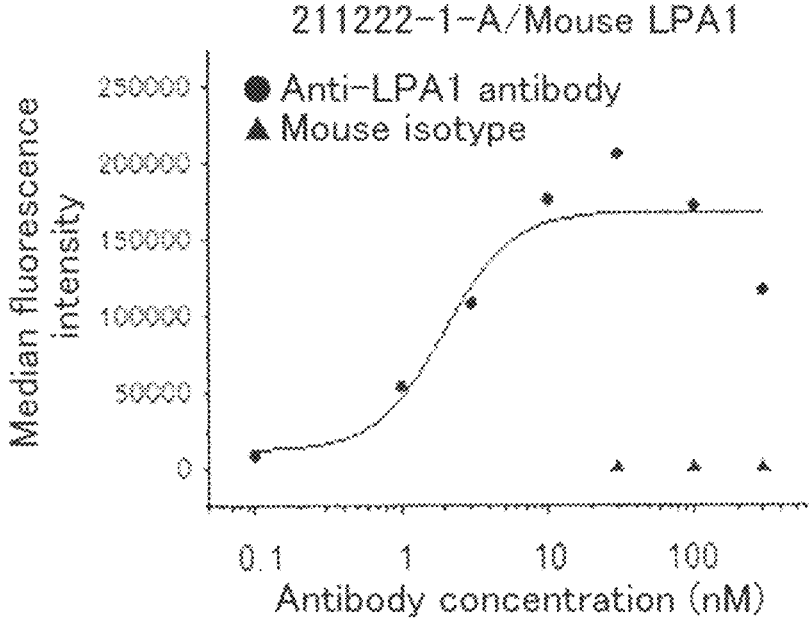
FIG. 3K is a graph presenting an evaluation result of a binding property of an antibody (211222-1-A) to a mouse LPA1-stably expressing CHO cell.

As representative examples, histograms of 210309-4-A measured by the flow cytometer are presented in FIG. 1. It was investigated whether or not a rightward shift of the histogram was caused in the case using the gene transfected cells compared to the case using the non-transfected cells. First, in the case using the anti-FLAG mouse IgG antibody as the primary antibody, all of the human LPA1 gene transfected cell, the human LPA2 gene transfected cell, the human LPA3 gene transfected cell, the mouse LPA1 gene transfected cell, the mouse LPA2 gene transfected cell, and the mouse LPA3 gene transfected cell showed the rightward shifts. On the other hand, in the case using the mouse isotype control antibody as the primary antibody or the case using the secondary antibody alone, all gene transfected cells showed no rightward shift. From this finding, it was confirmed that all receptors were expressed on the cell surface.

On the other hand, in the case using 210309-4-A as the primary antibody, only the human LPA1 gene transfected cell and mouse LPA1 gene transfected cell showed rightward shifts in the histograms. From this finding, it was confirmed that 210309-4-A bound specifically to the human LPA1 and mouse LPA extracellular domains but not to any of the human LPA2, human LPA3, mouse LPA2, and mouse LPA3 extracellular domains.

For antibodies other than 210309-4-A, the same results as in FIG. 1 were obtained.

The binding specificities of the eleven antibodies including antibodies other than 210309-4-A are presented in Table 2. Antibodies showing a rightward shift in the histogram were indicated as "+", antibodies showing no rightward shift were indicated as "−". It was observed that all the eleven antibodies bound specifically to the extracellular domains of the human LPA1 and mouse LPA but not to all extracellular domains of the human LPA2, human LPA3, mouse LPA2, and mouse LPA3, and the eleven antibodies were confirmed to bind specifically to the extracellular domain of the human LPA1 but not specifically to the extracellular domains of the human LPA2 and human LPA3.

TABLE 2

| Antibody | Binding specificity | | | | | |
| | Human LPA1 | Human LPA2 | Human LPA3 | Mouse LPA1 | Mouse LPA2 | Mouse LPA3 |
| --- | --- | --- | --- | --- | --- | --- |
| 210309-1-C | + | − | − | + | − | − |
| 210309-1-G | + | − | − | + | − | − |
| 210309-2-A | + | − | − | + | − | − |
| 210309-2-D | + | − | − | + | − | − |
| 210309-4-A | + | − | − | + | − | − |
| 210310-1-D | + | − | − | + | − | − |
| 210420-4-E | + | − | − | + | − | − |
| 210420-1-H | + | − | − | + | − | − |
| 210420-3-E | + | − | − | + | − | − |
| 211222-1-G | + | − | − | + | − | − |
| 211222-1-A | + | − | − | + | − | − |

[Example 5] CDR Sequencing in Antibody Heavy Chain Variable Region and Antibody Light Chain Variable Region The eleven antibody genes 210309-1-C, 210309-1-G, 210309-2-A, 210309-2-D, 210309-4-A, 210310-1-D, 210420-4-E, 210420-1-H, 210420-3-E, 21 1222-1-G, and 211222-1-A selected in Example 3 were cloned into pET vector by a homologous sequence-selective recombination cloning (Kurosawa N, Yoshioka M, and Isobe M., "Target-selective homologous recombination cloning for high-throughput generation of monoclonal antibodies from single plasma cells", BMC Biotechnol., 2011; 11: 39). Furthermore, to analyze the sequence of the cloned antibody heavy chain variable region (VH region), the VH region was sequenced by a sequence analysis using the VH second reverse primer (SEQ ID NO: 117) used in Example 2. Similarly, to analyze the sequence of the cloned antibody light chain variable region (VL region), the VL region was sequenced by a sequence analysis using the VL second reverse primer (SEQ ID NO: 118) used in Example 2. For determination of the CDR, Kabat numbering method and JMGT numbering method are combined for analysis, a region comprehensively including regions determined by the both numbering methods was determined as the CDR.

Amino acid sequences (AA) of the heavy chain variable region, the heavy chain CDRs 1 to 3, the light chain variable region, and the light chain CDRs 1 to 3 of each antibody, as well as the nucleotide sequences of DNAs individually coding for the heavy chain variable region and light chain variable region of each antibody are summarized in Tables 3-1 to 3-11.

TABLE 3-1

| | TABLE 3-1: 210309-4-A | | |
|---|---|---|---|
| SEQ ID NO: | Region | Type | Sequence |
| 1 | Heavy chain CDR1 | AA | GYTFTSYGIS |
| 2 | Heavy chain CDR2 | AA | EIYPRSGNTYYNEKFKG |
| 3 | Heavy chain CDR3 | AA | ARESISRRLGWNEDV |
| 4 | Light chain CDR1 | AA | RASENIYSFLA |
| 5 | Light chain CDR2 | AA | NAKTLTE |
| 6 | Light chain CDR3 | AA | QHHYGPPLT |
| 7 | Heavy chain variable region | AA | QVQLQQSGAELARPGASVKLSCKASGYTFTSYGISWVKQRTGQGLEWIGEIY PRSGNTYYNEKFKGKATLTADKSSSTAYMELRSLTSEDSAVYFCARESISRR LGWNEDVWGTGTTVTVSS |
| 8 | Heavy chain variable region | DNA | caggttcagctgcagcagtctggagctgagctggcgaggcctggggcttcag tgaagctgtcctgcaaggcttctggctacaccttcacaagctatggtataag ctgggtgaagcagagaactggacagggccttgagtggattggagagatttat cctagaagtggtaatacttactacaatgagaagttcaagggcaaggccacac tgactgcagacaaatcctccagcacagcgtacatggagctccgcagcctgac atctgaggactctgcggtctatttctgtgcaagagagtctatatcacgacgg ctaggctggaacttcgatgtctggggcacagggaccacggtcaccgtctcct ca |
| 9 | Light chain variable region | AA | DIHMTQSPASLSASVGETVTITCRASENIYSFLAWYQQKQGKSPHLVVYNAK TLTEGVPSRFSGSGSGTHFSLKINSLQPEDFGIYYCQHHYGPPLTFGAGTKL ELK |
| 10 | Light chain variable region | DNA | gacatccacatgactcagtctccagcctccctatctgcatctgtgggagaaa ctgtcaccatcacatgtcgagcaagtgagaatatttacagttttttagcatg gtatcagcagaaacagggaaaatctcctcacctcgtggtctacaatgcaaag accttaacagaaggtgtgccatcaaggttcagtggcagtggatcaggcacac acttttctctgaagatcaacagccttcagcctgaagattttgggatttatta ctgtcaacatcattatggtcctcctctcacgttcggtgctgggaccaagctg gagctgaaa |

TABLE 3-2

| | TABLE 3-2: 210309-1-C | | |
|---|---|---|---|
| SEQ ID NO: | Region | Type | Sequence |
| 11 | Heavy chain CDR1 | AA | GYSFTAYGIS |
| 12 | Heavy chain CDR2 | AA | EIYPRSGNTYYSEKFKG |
| 13 | Heavy chain CDR3 | AA | ARESLLKRLGWYFDV |
| 14 | Light chain CDR1 | AA | RASQNIYSFLA |
| 15 | Light chain CDR2 | AA | NAKTLAE |
| 16 | Light chain CDR3 | AA | QHHYGPPLT |
| 17 | Heavy chain variable region | AA | QVHLQQSGAELARPGASVKLSCKASGYSFTAYGISWVQQRTGQGLEWIGEIY PRSGNTYYSEKFKGKATLTADKSSSTAYMELRSLTSEDSAVYFCARESLLKR LGWYFDVWGTGTTVTVSS |
| 18 | Heavy chain variable region | DNA | caggttcatctgcagcagtctggagctgagctggcgaggcctggggcttcag tgaagctgtcctgcaaggcttctggctacagcttcacagcctatggtataag ctgggtgcagcagagaactggacagggccttgagtggattggagagatttat ccaagaagtggtaatacttactacagtgagaagttcaagggcaaggccacac tgactgcagacaaatcctccagtacagcgtacatggagctccgcagcctgac atctgaggactctgcggtctatttctgtgcaagagagtctctattaaaacgg ctaggctggtacttcgatgtctggggcacagggaccacggtcaccgtctcct ca |

TABLE 3-2-continued

| SEQ ID NO: | Region | Type | Sequence |
|---|---|---|---|
| | TABLE 3-2: 210309-1-C | | |
| 19 | Light chain variable region | AA | DIQMTQSPASLSASVGETVTITCRASQNIYSFLAWYQQKQGNSPQLLVYNAK TLAEGVPSRFSGSGSGTQFSLKINSLQPEDFGSYYCQHHYGPPLTFGVGTKL ELK |
| 20 | Light chain variable region | DNA | gacatccagatgactcagtctccagcctccctatctgcatctgtgggagaaa ctgtcaccatcacatgtcgagcaagtcagaatatttacagttttttagcatg gtatcagcagaaacagggaaattctcctcagctcctggtctataatgcaaaa accttagcagaaggtgtgccatcaaggttcagtggcagtggatcaggcacac agttttctctgaagatcaacagcctgcagcctgaagattttgggagttatta ctgtcaacatcattatggtcctcctctcacgttcggtgttgggaccaagctg gagctgaaa |

TABLE 3-3

| SEQ ID NO: | Region | Type | Sequence |
|---|---|---|---|
| | TABLE 3-3: 210309-1-G | | |
| 21 | Heavy chain CDR1 | AA | GYTFTSYGIS |
| 22 | Heavy chain CDR2 | AA | EIYPRSGVTYYNEKFKG |
| 23 | Heavy chain CDR3 | AA | ARESISLRLGWYFDV |
| 24 | Light chain CDR1 | AA | RASENIYRELA |
| 25 | Light chain CDR2 | AA | NAKTLAE |
| 26 | Light chain CDR3 | AA | QHHYGPPLT |
| 27 | Heavy chain variable region | AA | QVQLQQSGAELARPGASMKLSCRASGYTFTSYGISWVKQRTGQGLEWIGEIY PRSGVTYYNEKFKGRATLTADKSSSTAFMELRSLTSEDSAVYFCARESISLR LGWYFDVWGTGTTVTVSS |
| 28 | Heavy chain variable region | DNA | caggttcagctgcagcagtctggagctgagctggcgaggcctggggcttcaa tgaagctgtcctgcagggcttctggctacaccttcacaagctatggtataag ctgggtgaagcagagaactggacagggccttgagtggattggagagatttat cccagaagtggtgttacttactacaatgagaagttcaaggggtagggccacac tgactgcagacaaatcctccagcacagcgttcatggagctccgcagcctgac atctgaggactctgcggtctatttctgtgcaagagagtctatatcactacga ctaggctggtacttcgatgtctggggcacagggaccacggtcaccgtctcct ca |
| 29 | Light chain variable region | AA | DIQMTQSPASLSASVGDTVTITCRASENIYRFLAWYQQKQRKSPHLLVYNAK TLAEGVPSRFSGSGSGTQFSLKINSLQPEDEGSYYCQHHYGPPLTFGAGTKL ELT |
| 30 | Light chain variable region | DNA | gacatccagatgactcagtctccagcctccctatctgcatctgtgggagata ctgtcaccatcacatgtcgagcaagtgagaatatttacaggtttttagcatg gtatcagcagaaacagagaaaatctccgcacctcctggtctataatgcaaaa accttagcagaaggtgtgccatcaaggttcagtggcagtggatcaggcacac agttttctctgaagatcaacagtctgcagcctgaagattttgggagttatta ttgtcaacatcattatggtcctccactcacgttcggtgctgggaccaagctg gagctgaca |

TABLE 3-4

| SEQ ID NO: | Region | Type | Sequence |
|---|---|---|---|
| | | | TABLE 3-4: 210309-2-A |
| 31 | Heavy chain CDR1 | AA | GYTFTSYGIS |
| 32 | Heavy chain CDR2 | AA | EIYPRSGNTYYNEKEKG |
| 33 | Heavy chain CDR3 | AA | ARESILLRLGWYFDV |
| 34 | Light chain CDR1 | AA | RASENIYRELA |
| 35 | Light chain CDR2 | AA | NAKTLAE |
| 36 | Light chain CDR3 | AA | QHHYGPPLT |
| 37 | Heavy chain variable region | AA | QVQLQQSGAELARPGASVKLSCKASGYTFTSYGISWVKQRTGQGLEWIGEIY PRSGNTYYNEKFKGRATLTADKSSSTAYMELRSLTSEDSAVYFCARESILLR LGWYFDVWGTGTTVTVSS |
| 38 | Heavy chain variable region | DNA | caggttcagctgcagcagtctggagctgagctggcgaggcctggggcttcag tgaagctgtcctgcaaggcttctggctacaccttcacaagctatggtataag ctgggtgaagcagagaactggacagggccttgagtggattggagagatttat cctagaagtggtaatacttactacaatgagaagttcaagggccagggccacac tgactgcagacaaatcctccagcacagcgtacatggagctccgcagcctgac atctgaggactctgcggtctatttctgtgcaagagagtctatattactacgg ctaggctggtacttcgatgtctggggcacagggaccacggtcaccgtctcct ca |
| 39 | Light chain variable region | AA | DIQMTQSPASLSASVGGTVTITCRASENIYRFLAWYQQKQGKSPQLLVYNAK TLAEGVPSRFSGSGSGTQFSLKINSLQPEDFGIYYCQHHYGPPLTFGAGTKL ELK |
| 40 | Light chain variable region | DNA | gacatccagatgactcagtctccagcctccctatctgcatctgtgggaggaa ctgtcaccatcacatgtcgagcaagtgagaatatttacaggtttttagcatg gtatcagcagaaacagggaaaatctcctcagctcctggtctataatgcaaaa accttagcagaaggtgtgccatcaaggttcagtggcagtggatcaggcacac agttttctctgaagatcaacagccttcagcctgaagattttgggatttatta ctgtcaacatcattatggtcctcctctcacgttcggtgctgggaccaagctg gagctgaaa |

TABLE 3-5

| SEQ ID NO: | Region | Type | Sequence |
|---|---|---|---|
| | | | TABLE 3-5: 210309-2-D |
| 41 | Heavy chain CDR1 | AA | GYTFTSYGIS |
| 42 | Heavy chain CDR2 | AA | EIYPRSGNTYYNEKVKG |
| 43 | Heavy chain CDR3 | AA | ARESIFLRLGWYFDV |
| 44 | Light chain CDR1 | AA | RASDNIYRFLA |
| 45 | Light chain CDR2 | AA | NAKTLAE |
| 46 | Light chain CDR3 | AA | QHHYGPPLT |
| 47 | Heavy chain variable region | AA | QVQLQQSGAELARPGASVKLSCKASGYTFTSYGISWVKQRTGQGLEWIGEIY PRSGNTYYNEKVKGATLTADKSSSTAYMELRSLTSEDSAVYFCARESIFLR LGWYFDVWGTGTTVTVSS |
| 48 | Heavy chain variable region | DNA | caggttcagctgcagcagtctggagctgagctggcgaggcctggggcttcag tgaagctgtcctgcaaggcttctggctacaccttcacaagctatggtataag ttgggtgaagcagagaactggacagggccttgagtggattggagagatttat cctagaagtggtaatacttactacaatgagaaggtcaagggccaaggccacac tgactgcagacaaatcctccagcacagcgtacatggagctccgcagcctgac atctgaggactctgcggtctatttctgtgcaagagagtctatattcctacgt ctaggctggtacttcgatgtctggggcacagggaccacggtcaccgtctcct ca |

TABLE 3-5-continued

| | TABLE 3-5: 210309-2-D | | |
|---|---|---|---|
| SEQ ID NO: | Region | Type | Sequence |
| 49 | Light chain variable region | AA | DIQMTQSPASLSASVGETVTITCRASDNIYRFLAWYQQKGKSPQLLVYNAK TLAEGVPSRFSGSGTGTQFSLKINSLQPEDFGIYYCQHHYGPPLTFGAGTKL ELK |
| 50 | Light chain variable region | DNA | gacatccagatgactcagtctccagcctccctatctgcatctgtgggagaaa ctgtcaccatcacatgtcgagcaagtgacaatatttacaggtttttagcatg gtatcagcagaaacagggaaaatctcctcagctcctggtctataatgcaaaa accttagcagaaggtgtgccatcaaggttcagtggcagtggaacaggcacac agtttctctgaagatcaacagtcttcagcctgaagattttgggatttatta ctgtcaacatcattatggtcctcctctcacgttcggtgctgggaccaagctg gagctgaaa |

TABLE 3-6

| | TABLE 3-6: 210310-1-D | | |
|---|---|---|---|
| SEQ ID NO: | Region | Type | Sequence |
| 51 | Heavy chain CDR1 | AA | GYTFTSFGVN |
| 52 | Heavy chain CDR2 | AA | QIYPRTGTTYHNERFKG |
| 53 | Heavy chain CDR3 | AA | AREGDRYSLAY |
| 54 | Light chain CDR1 | AA | RASENIYRELA |
| 55 | Light chain CDR2 | AA | NAKTLVE |
| 56 | Light chain CDR3 | AA | QHHYGIPLT |
| 57 | Heavy chain variable region | AA | QVQVQQSGAELARPGASVRLSCKASGYTFTSFGVNWVKQRTGQGLEWIGQIY PRTGTTYHNERFKGKATLTTDKSSSTAYMELRSLTSEDSAVYFCAREGDRYS LAYWGQGTLVTVSA |
| 58 | Heavy chain variable region | DNA | caggttcaggtacagcagtccggagctgagctggcgaggcctggggcatcag tgaggctgtcctgcaaggcttctggctacaccttcacaagctttggtgtaaa ctgggtgaagcagagaactggacagggccttgagtggattggacagatttat cctagaactggtactacttaccacaatgagaggttcaagggcaaggccacac tgactacagacaaatcctccagcacagcgtacatggagctccgcagcctgac atctgaggactctgcggtctatttctgtgcacgagagggagataggtactca cttgcttactggggccaagggactctggtcactgtctctgca |
| 59 | Light chain variable region | AA | DIQMTQSPASLSASVGETVTITCRASENIYRFLAWYQQKGKSPQLLVYNAK TLVEGVPSRFSGSGSGTQFSLKINNLQPEDEGSYYCQHHYGIPLTFGAGTKL ELK |
| 60 | Light chain variable region | DNA | gacatccagatgactcagtctccagcctccctatctgcatctgtgggagaaa ctgtcaccatcacatgtcgagcaagtgagaatatttacaggtttttagcatg gtatcagcagaaacagggaaaatctcctcagctcctggtctataatgcaaaa accttagtagaaggtgtgccatcaaggttcagtggcagtggatcaggcacac agtttctctgaagatcaacaacctacagcctgaagattttgggagttatta ctgtcaacatcattatggtattccgctcacgttcggtgctgggaccaagctg gagctgaaa |

TABLE 3-7

| | TABLE 3-7: 210420-4-E | | |
|---|---|---|---|
| SEQ ID NO: | Region | Type | Sequence |
| 61 | Heavy chain CDR1 | AA | GYTFASFGIS |
| 62 | Heavy chain CDR2 | AA | EIYPRSGTTYFNEKERG |

TABLE 3-7-continued

| SEQ ID NO: | Region | Type | Sequence |
|---|---|---|---|
| | | | TABLE 3-7: 210420-4-E |
| 63 | Heavy chain CDR3 | AA | AREGVRRYAMDY |
| 64 | Light chain CDR1 | AA | RASGNIYSFLA |
| 65 | Light chain CDR2 | AA | NAKTLAE |
| 66 | Light chain CDR3 | AA | QHHYGIPLT |
| 67 | Heavy chain variable region | AA | QLHLQQSGAELARPGASVRLSCKASGYTFASFGISWVKQRTGQGLEYIGEIY PRSGTTYFNEKFRGKATLSADKSSSTAYMELRSLTSEDSAVYFCAREGVRRY AMDYWGQGTSVTVSS |
| 68 | Heavy chain variable region | DNA | cagcttcacctgcagcagtctggagctgagctggcgaggcctggggcttcag tgaggctgtcctgcaaggcttctggctacaccttcgcaagtttggtataag ctgggtgaagcagagaactggacagggccttgaatacattggagagatttat cctagaagtggtactacttacttcaatgagaagttcaggggcaaggccacac tgagtgcagacaaatcatccagcacagcgtacatggagctccgcagcctgac atctgaggactctgcggtctatttctgtgcaagagagggagtacgacggtat gctatggactactggggtcaaggaacctcagtcaccgtctcctca |
| 69 | Light chain variable region | AA | DIQVTQSPASLSASVGETVTITCRASGNIYSFLAWYQQKQGKSPQLLVYNAK TLAEGVPSRFSGSGSGTQFSLKISSLQPEDEGSYYCQHHYGIPLTFGAGTKL DLK |
| 70 | Light chain variable region | DNA | gacatccaggtgactcagtctccagcctccctatctgcgtctgtgggagaaa ctgtcaccatcacatgtcgcgcaagtgggaatatttacagtttttttagcatg gtatcagcagaaacagggaaaatctcctcaactcctggtctataatgcaaaa actttagcagaaggtgtgccatcaaggttcagtggcagtggatcaggcacac agttttctctgaagatcagcagcctgcagcctgaagattttgggagttatta ctgtcaacatcattatggtattcctctcacgttcggtgctgggaccaagttg gacctgaaa |

TABLE 3-8

| SEQ ID NO: | Region | Type | Sequence |
|---|---|---|---|
| | | | TABLE 3-8: 210420-1-H |
| 71 | Heavy chain CDR1 | AA | GYTFASEGIS |
| 72 | Heavy chain CDR2 | AA | EIYPRSGTTYFNEKERG |
| 73 | Heavy chain CDR3 | AA | AREGVRRYAMDY |
| 74 | Light chain CDR1 | AA | RASGNIYSFLA |
| 75 | Light chain CDR2 | AA | NAKTLAE |
| 76 | Light chain CDR3 | AA | QHHYGIPLT |
| 77 | Heavy chain variable region | AA | QFQLQQSGAELARPGASVKLSCKASGYTFASFGISWVKQRTGQGLEYIGEIY PRSGTTYFNEKFRGKATLTADKSSSTAYMELRSLTSEDSAVYFCAREGVRRY AMDYWGQGTSVTVSS |
| 78 | Heavy chain variable region | DNA | cagtttcagctgcagcagtctggagctgagctggcgaggcctggggcttcag tgaagctgtcctgcaaggcttctggctacaccttcgcaagctttggtataag ctgggtgaaacagagaactggacagggccttgaatacattggagagatttat cctagaagtggtactacttacttcaatgagaaattcaggggcaaggccacac tgactgcagacaaatcatccagcacagcgtacatggagctccgcagcctgac atctgaggactctgcggtctatttctgtgcaagagaggggggtacgacggtat gctatggactactggggtcaaggaacctcagtcaccgtctcctca |
| 79 | Light chain variable region | AA | DIQVTQSPASLSASVGETVTITCRASGNIYSFLAWYQQKQGKSPQLLVYNAK TLAEGVPSRFSGSGSGTQFSLKISSLQPEDFGSYYCQHHYGIPLTFGGGTKL DLK |

TABLE 3-8-continued

| | | | TABLE 3-8: 210420-1-H | | | |
|---|---|---|---|

| SEQ ID NO: | Region | Type | Sequence |
|---|---|---|---|
| 80 | Light chain variable region | DNA | gacatccaggtgactcagtctccagcctccctatctgcgtctgtgggagaaa ctgtcaccatcacatgtcgcgcaagtgggaatatttacagttttttagcatg gtatcagcagaaacagggaaaatctcctcagctcctggtctataatgcaaaa accttagcagaaggtgtgccatcaaggttcagtggcagtggatcaggcacac agttttctctgaagattagcagcctgcagcctgaagattttgggagttatta ctgtcaacatcattatggtattcctctcacgttcggtggtgggaccaagttg gacctgaaa |

TABLE 3-9

| | | | TABLE 3-9: 210420-3-E | | | |
|---|---|---|---|

| SEQ ID NO: | Region | Type | Sequence |
|---|---|---|---|
| 81 | Heavy chain CDR1 | AA | GYTFASEGIS |
| 82 | Heavy chain CDR2 | AA | EIYPRSGTTYFNEKERG |
| 83 | Heavy chain CDR3 | AA | AREGVRRYAMDY |
| 84 | Light chain CDR1 | AA | RASGNIYSFLA |
| 85 | Light chain CDR2 | AA | NAKTLAE |
| 86 | Light chain CDR3 | AA | QHHYGIPLT |
| 87 | Heavy chain variable region | AA | QLQLQQSGAELARPGASVKLSCKASGYTFASFGISWVKQRAGQGLEYIGEIY PRSGTTYFNEKFRGKATLTADKSSSTAYMELRRLTSEDSAVYFCAREGVRRY AMDYWGQGTSVTVSS |
| 88 | Heavy chain variable region | DNA | cagcttcagctgcagcagtctggagctgagctggcgaggcctggggcttcag tgaagctgtcctgcaaggcttctggctacacaccttcgcaagttttggtataag ttgggtgaagcagagagctggacagggccttgagtacattggagagatttat cctagaagtggtactacttacttcaatgagaagttcaggggcaaggccacac tgactgcagacaaatcatccagcacagcgtacatggagctccgcagactgac atctgaggactctgcggtctatttctgtgcaagagaggggtacgacggtat gctatggactactgggtcaaggaacctcagtcaccgtctcctca |
| 89 | Light chain variable region | AA | DIQVTQSPASLSASVGETVTITCRASGNIYSFLAWYQQKQGKSPQLLVYNAK TLAEGVPSRFSGSGSGTQFSLKINSLQPEDFGSYYCQHHYGIPLTFGAGTKL DLK |
| 90 | Light chain variable region | DNA | gacatccaggtgactcagtctccagcctccctatctgcgtctgtgggagaaa ctgtcaccatcacatgtcgcgcaagtgggaatatttacagttttttagcatg gtatcagcagaaacagggaaaatctcctcagctcctggtctataatgcaaaa accttagcagaaggtgtgccatcaaggttcagtggcagtggatcaggcacac agttttctctgaagatcaacagcctgcagcctgaagattttgggagttatta ctgtcaacatcattatggtattcctctcacgttcggtgctgggaccaagttg gacctgaaa |

TABLE 3-10

| | | | TABLE 3-10: 211222-1-G | | | |
|---|---|---|---|

| SEQ ID NO: | Region | Type | Sequence |
|---|---|---|---|
| 91 | Heavy chain CDR1 | AA | GYTFTSFGVN |
| 92 | Heavy chain CDR2 | AA | QIYPRTGTTYHNERFKG |
| 93 | Heavy chain CDR3 | AA | AREGDRYSLAY |
| 94 | Light chain CDR1 | AA | RASENIYRFLA |

TABLE 3-10-continued

| | | | TABLE 3-10: 211222-1-G | | | |
|---|---|---|---|

| SEQ ID NO: | Region | Type | Sequence |
|---|---|---|---|
| 95 | Light chain CDR2 | AA | NAKTLVE |
| 96 | Light chain CDR3 | AA | QHHYGIPLT |
| 97 | Heavy chain variable region | AA | QVQVQQSGAELARPGASVRLSCKASGYTFTSFGVNWVKQRTGQGLEWIGQIY PRTGTTYHNERFKGKATLTADKSSSTAYMELRSLTSEDSAVYFCAREGDRYS LAYWGQGTLVTVSA |
| 98 | Heavy chain variable region | DNA | caggttcaggtacagcagtccggagctgagctggcgaggcctggggcatcag tgaggctgtcctgcaaggcttctggctacaccttcacaagttttggtgtaaa ctgggtgaagcagagaactggacagggccttgagtggattggacagatttat cctagaactggtactacttaccacaatgagaggttcaagggcaaggccacac tgactgcagacaagtcctccagcacagcgtacatggagctccgcagcctgac atctgaggactctgcggtctatttctgtgcacgagagggagataggtactca cttgcttactggggccaagggactctggtcactgtctctgca |
| 99 | Light chain variable region | AA | DIQMTQSPASLSASVGETVTITCRASENIYRFLAWYQQKQGKSPQLLVYNAK TLVEGVPSRFSGSGSGTQFSLKINNLQPEDFGSYYCQHHYGIPLTFGAGTKL ELK |
| 100 | Light chain variable region | DNA | gacatccagatgactcagtctccagcctccctatctgcatctgtgggagaaa ctgtcaccatcacatgtcgagcaagtgagaatatttacaggttttttagcatg gtatcagcagaaacagggaaaatctcctcagctcctggtctataatgcaaaa accttagtagaaggtgtgccatcaaggttcagtggcagtggatcaggcacac agttttctctgaagatcaacaacctacagcctgaagattttgggagttatta ctgtcaacatcattatggtattccgctcacgttcggtgctgggaccaagctg gagctgaaa |

TABLE 3-11

| | | | TABLE 3-11: 211222-1-A | | | |
|---|---|---|---|

| SEQ ID NO: | Region | Type | Sequence |
|---|---|---|---|
| 101 | Heavy chain CDR1 | AA | GYTFTSFGVN |
| 102 | Heavy chain CDR2 | AA | QIYPRSGTTYHNERFKG |
| 103 | Heavy chain CDR3 | AA | AREGDRYSLAY |
| 104 | Light chain CDR1 | AA | RASENIYRFLA |
| 105 | Light chain CDR2 | AA | NAKTLAE |
| 106 | Light chain CDR3 | AA | QHHYGIPLT |
| 107 | Heavy chain variable region | AA | QVQVHQSGAELARPGASVRLSCKASGYTFTSFGVNWVKQRTGQGLEWIGQIY PRSGTTYHNERFKGKATLTADKSSSTAYMELRSLTSEDSAVYFCAREGDRYS LAYWGQGTLVTVSA |
| 108 | Heavy chain variable region | DNA | caggttcaggtacaccagtccggagctgagctggcgaggcctggggcatcag tgaggctgtcctgcaaggcttctggctacaccttcacgagctttggtgtaaa ctgggtgaagcagagaactggacagggccttgagtggattggacagatttat cctagaagtggtactacttaccacaatgagaggttcaagggcaaggccacac tgactgcagacaaatcctccagcacagcgtacatggagctccgcagcctgac atctgaggactctgcggtctatttctgtgcaagagagggagataggtactca cttgcttactggggccaagggactctggtcactgtctctgca |
| 109 | Light chain variable region | AA | DIQMTQSPASLSASVGETVTITCRASENIYRFLAWYQQKQGKSPQLLVSNAK TLAEGVPSRFSGSGSGTQFSLKINYLQPEDEGNYYCQHHYGIPLTFGAGTKL ELK |
| 110 | Light chain variable region | DNA | gacatccagatgactcagtctccagcctccctatctgcatctgtgggagaaa ctgtcaccatcacatgtcgagcaagtgagaatatttacaggttttttagcatg gtatcagcagaaacagggaaaatctcctcagctcctggtctctaatgcaaaa accttagcagaaggtgtgccatcaaggttcagtggcagtggatcaggcacac agttttctctgaagatcaactacctacagcctgaagattttgggaattatta ctgtcaacatcattatggtattccgctcacgttcggtgctgggaccaagctg gagctgaaa |

[Example 6] Evaluation of Binding Property to
LPA1 by Flow Cytometry

An artificial gene was synthesized, in which a heavy chain constant region and a K chain constant region of mouse IgG1 were connected to the VH regions and VL regions of 210309-1-C, 210309-1-G, 210309-2-A, 210309-2-D, 210309-4-A, 210310-1-D, 210420-4-E, 210420-1-H, 210420-3-E, 21 1222-1-G, and 211222-1-A, determined in Example 5. The antibody genes were introduced into a CHO cell, and from the culture supernatant of the cell, purified antibodies were produced by affinity chromatography and subjected to the following test. As a result of the purity test by sodium dodecyl sulfate polyacrylamide gel electrophoresis (SDS-PAGE), all the purified antibodies were confirmed to have purities of 9000 or higher.

The human LPA1-stably expressing CHO cell and the mouse LPA1-stably expressing CHO cell were washed with PBS, then detached from the cell culture dishes by an enzyme-free cell dissociation buffer (Thermo Fisher Scientific, Inc.), then washed with PBS, and then collected by centrifugation. The human LPA1-stably expressing CHO cell and the mouse LPA1-stably expressing CHO cell were suspended at $1 \times 10^7$ cells/mL in Fc Block (Sci-Tech Biosciences, Inc.) diluted by 500 times in FACS buffer, and then allowed to stand at 4° C. for 30 minutes to block the cells. The cells were collected by centrifugation and suspended in FACS buffer at $4 \times 10^6$ cells/mL, and this suspension was dispensed into a V-bottom 96-well plate (Thermo Fisher Scientific, Inc.) at 25 μL ($1 \times 10^5$ cells)/well. As primary antibodies, the eleven types of LPA1 antibodies produced and purified by the method described above and a mouse isotype control antibody (Fujifilm Wako Pure Chemicals Corporation) were diluted stepwise, which was added to each well at 25 μL/well, and allowed to stand at 4° C. for 1 hour. The cells were collected by centrifugation and washed with 120 μL of FACS buffer. This washing operation was repeated twice. To the cell sediment, 25 μL each of Goat Anti-Mouse IgG H&L (DyLight 650) (Abcam) that was a secondary antibody diluted by 500 times in FACS buffer was dispensed, then suspended, and then allowed to stand at 4° C. for 1 hour. The cells were washed twice, then suspended in 50 μL of FACS buffer, and the binding of antibodies to the cells was measured using a flow cytometer (Agilent Novocyte).

A graph was created, in which a concentration of the antibody was plotted on the vertical axis, and a median fluorescence intensity of the flow cytometer histogram was plotted on the horizontal axis. All of the eleven antibodies were confirmed to dose-dependently bind to the human LPA1-stably expressing CHO cell and the mouse LPA1-stably expressing CHO cell. The results of the binding of each antibody to the human LPA1-stably expressing CHO cell are presented in FIG. 2A to FIG. 2K, and the results of the binding of each antibody to the mouse LPA1-stably expressing CHO cell are presented in FIG. 3A to FIG. 3K. A 50% binding concentration (50% effective concentration (EC50)) of each antibody was calculated and summarized in Table 4.

TABLE 4

| | Binding to LPA1-stably expressing cell EC50 (nM) | |
| Antibody | Human LPA1-stably expressing cell | Mouse LPA1-stably expressing cell |
| --- | --- | --- |
| 210309-1-C | 1.7 | 1.8 |
| 210309-1-G | 1.8 | 2.4 |
| 210309-2-A | 1.4 | 2.1 |
| 210309-2-D | 1.8 | 2.1 |
| 210309-4-A | 1.5 | 1.1 |
| 210310-1-D | 2.7 | 2.1 |
| 210420-4-E | 2.0 | 1.3 |
| 210420-1-H | 2.5 | 1.6 |
| 210420-3-E | 1.9 | 1.0 |
| 211222-1-G | 4.2 | 2.3 |
| 211222-1-A | 2.3 | 2.0 |

Figure 4:
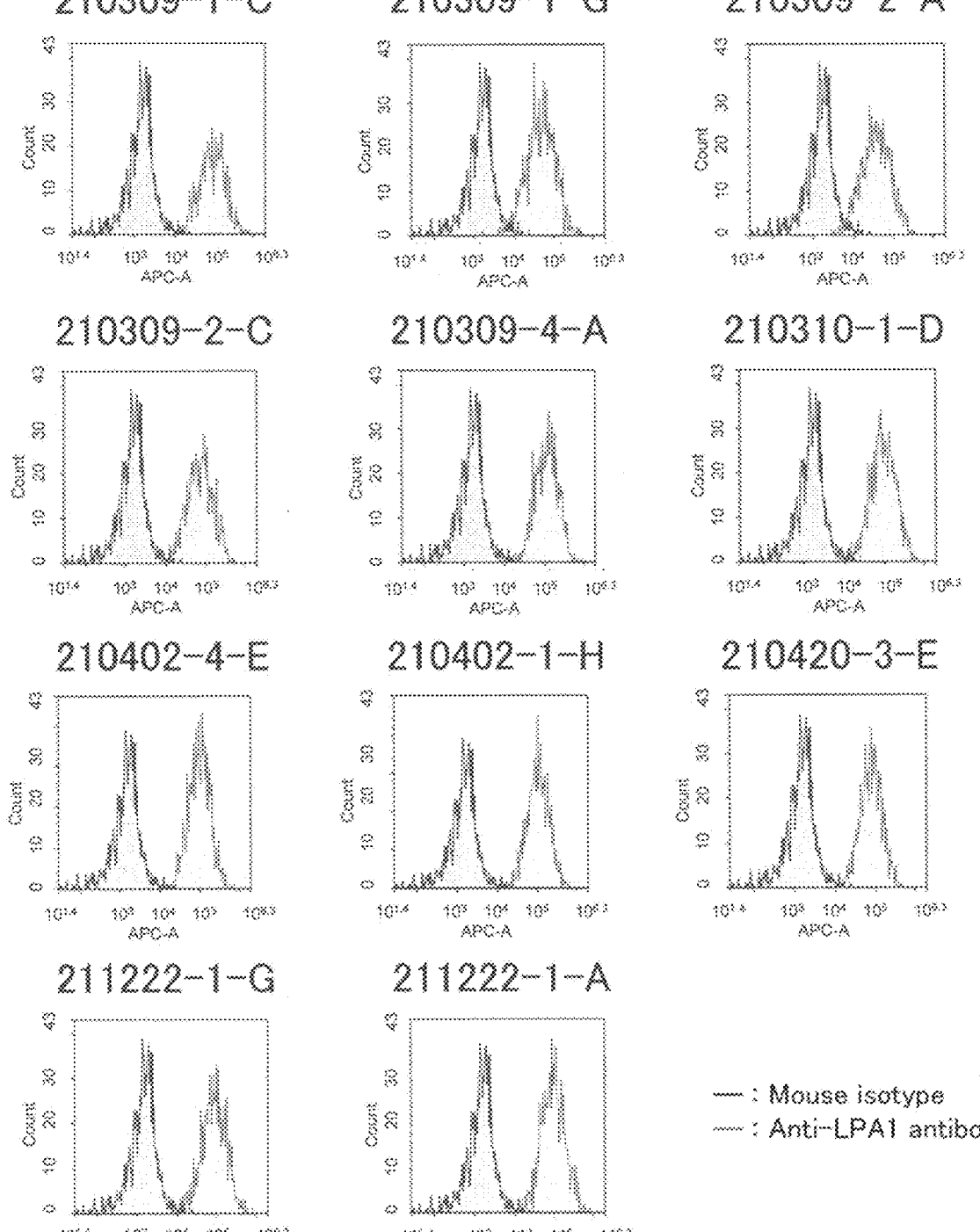
FIG. 4 is a histogram presenting results of flow cytometry performed in Example 6, showing a binding property between an antibody and an endogenous human LPA1.
Figure 5A:
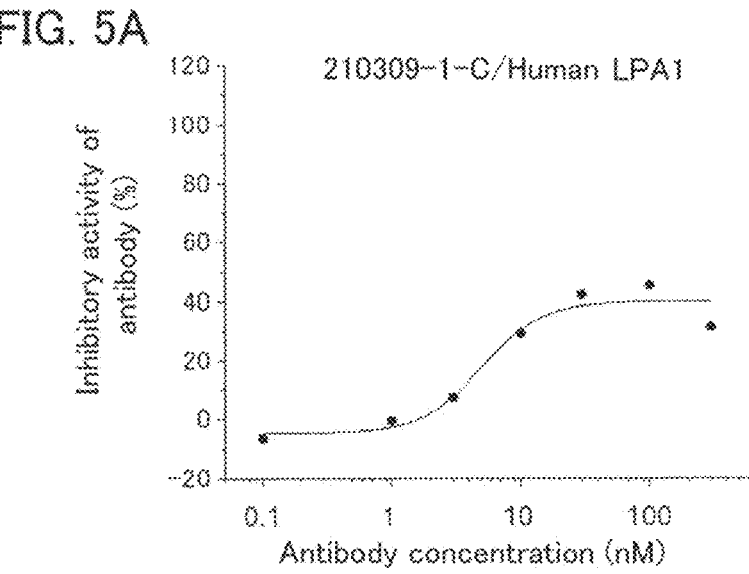
FIG. 5A is a graph presenting a dose dependency of an inhibitory activity of an antibody (210309-1-C) on human LPA1.
Figure 5B:
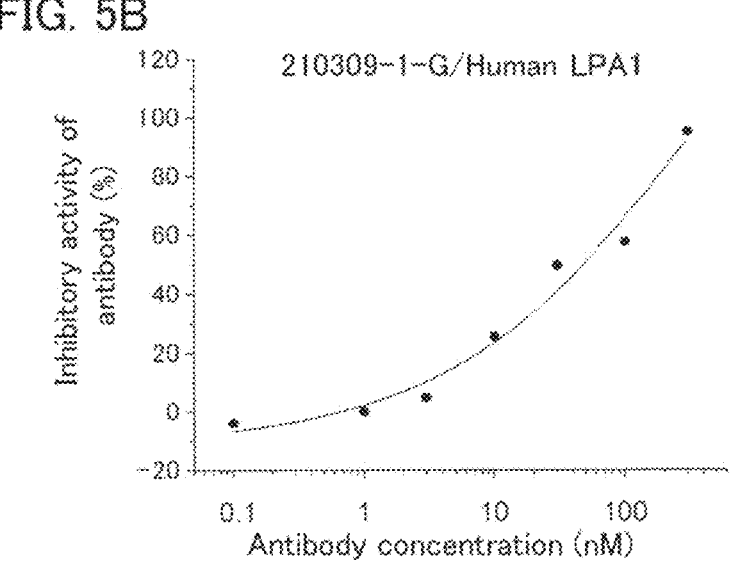
FIG. 5B is a graph presenting a dose dependency of an inhibitory activity of an antibody (210309-1-G) on human LPA1.
Figure 5C:
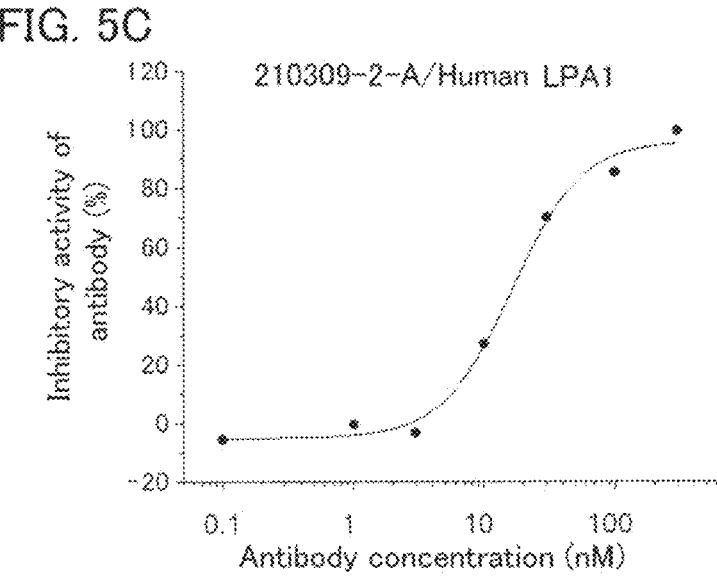
FIG. 5C is a graph presenting a dose dependency of an inhibitory activity of an antibody (210309-2-A) on human LPA1.
Figure 5D:
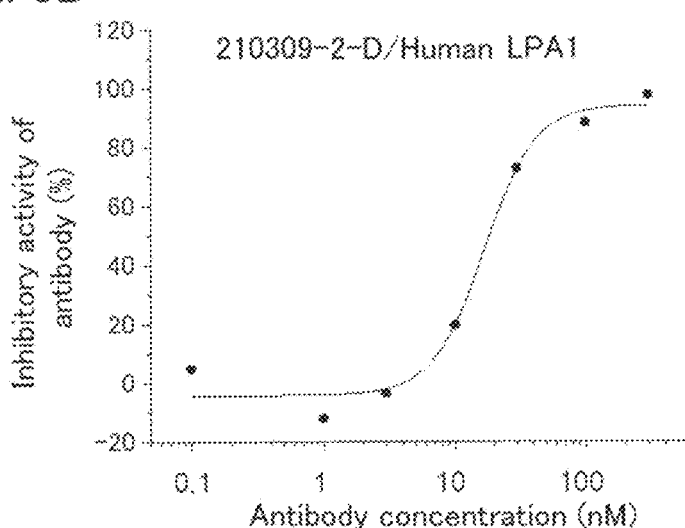
FIG. 5D is a graph presenting a dose dependency of an inhibitory activity of an antibody (210309-2-D) on human LPA1.
Figure 5E:
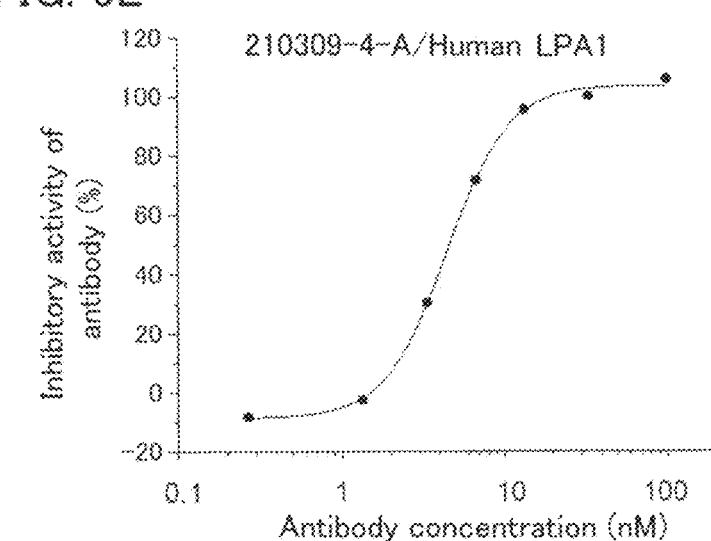
FIG. 5E is a graph presenting a dose dependency of an inhibitory activity of an antibody (210309-4-A) on human LPA1.
Figure 5F:
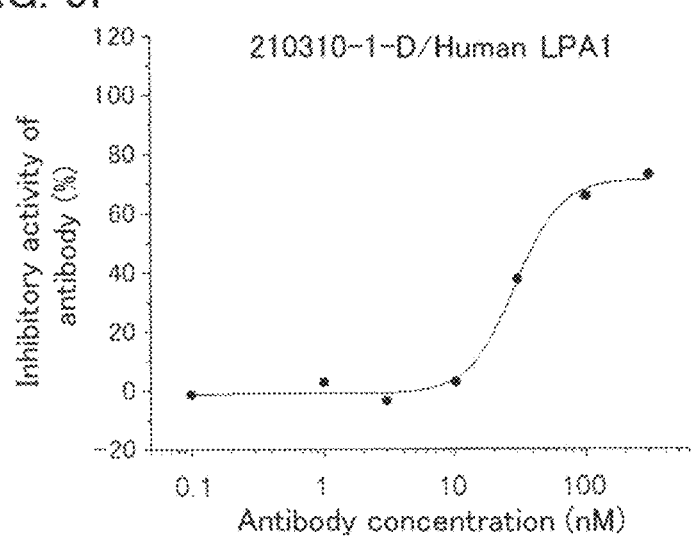
FIG. 5F is a graph presenting a dose dependency of an inhibitory activity of an antibody (210310-1-D) on human LPA1.
Figure 5G:
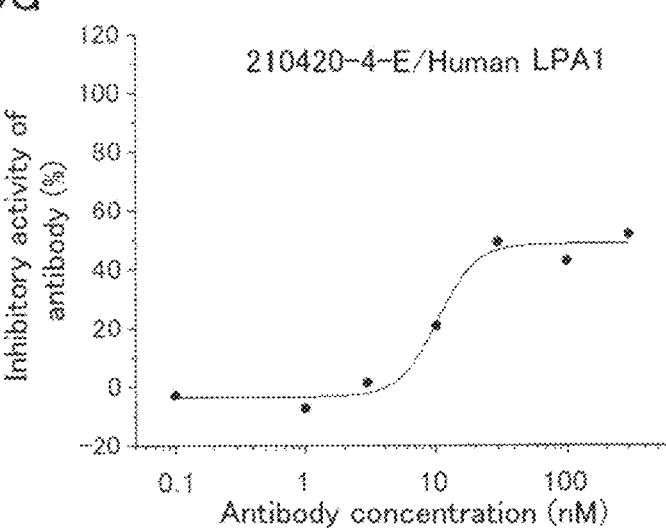
FIG. 5G is a graph presenting a dose dependency of an inhibitory activity of an antibody (210420-4-E) on human LPA1.
Figure 5H:
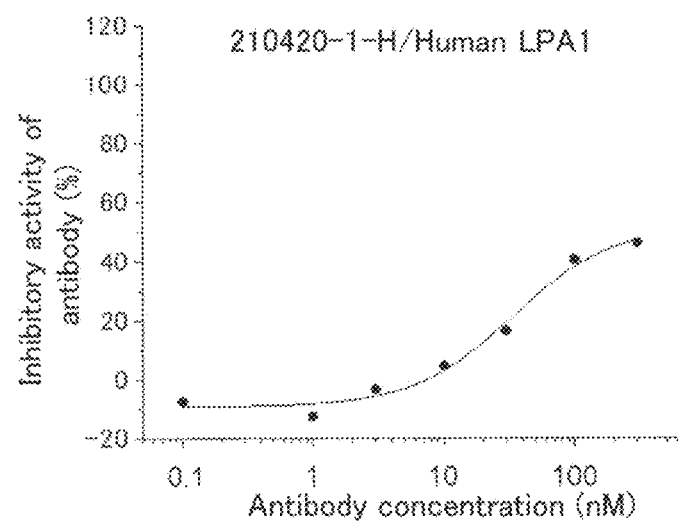
FIG. 5H is a graph presenting a dose dependency of an inhibitory activity of an antibody (210420-1-H) on human LPA1.
Figure 5I:
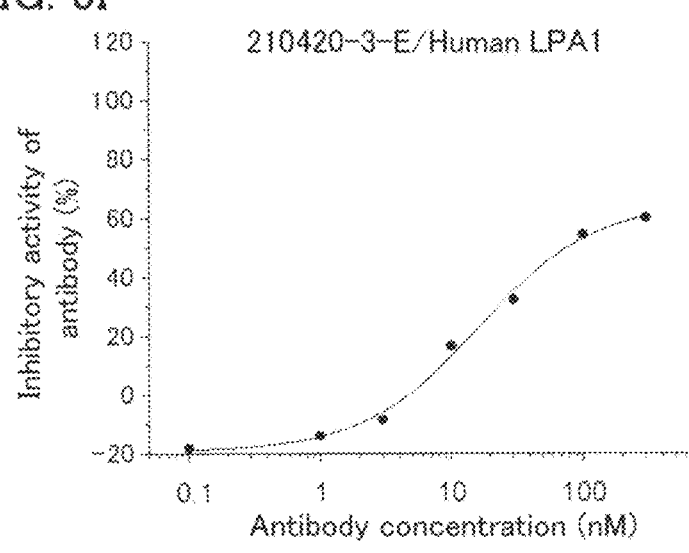
FIG. 5I is a graph presenting a dose dependency of an inhibitory activity of an antibody (210420-3-E) on human LPA1.
Figure 5J:
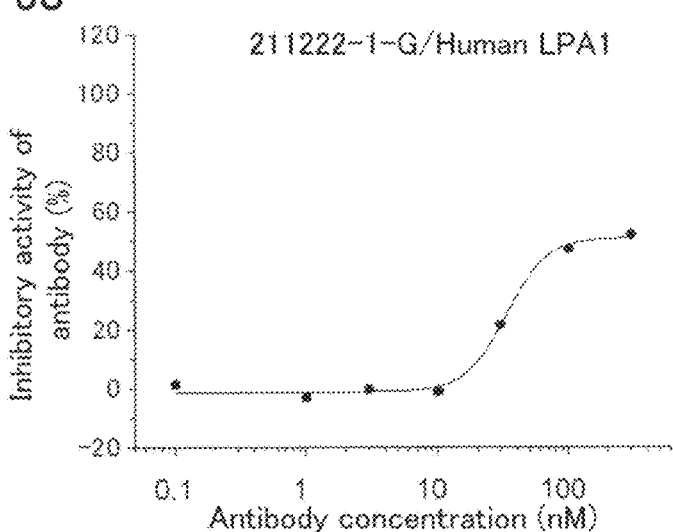
FIG. 5J is a graph presenting a dose dependency of an inhibitory activity of an antibody (211222-1-G) on human LPA1.
Figure 5K:
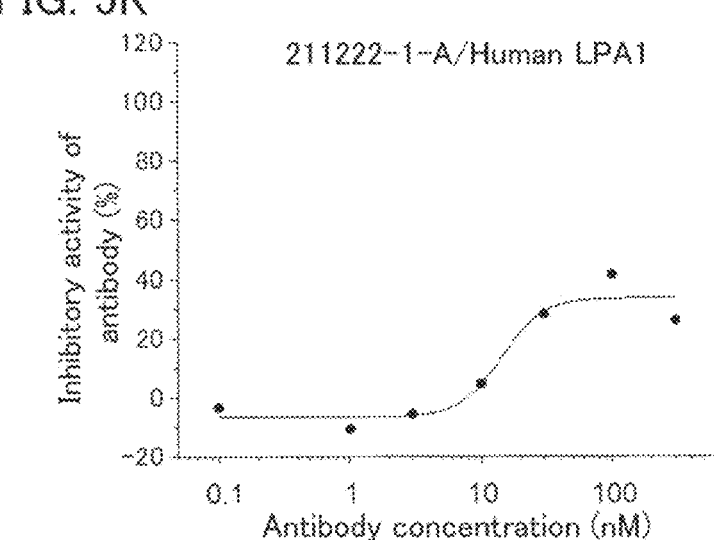
FIG. 5K is a graph presenting a dose dependency of an inhibitory activity of an antibody (211222-1-A) on human LPA1.
Figure 6A:
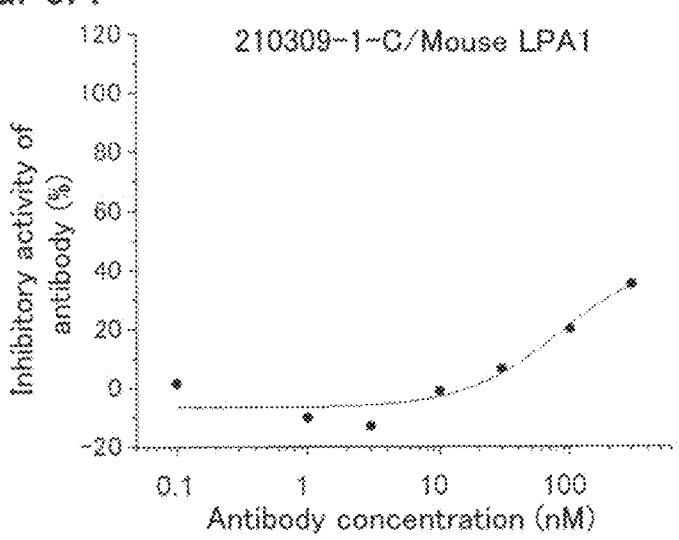
FIG. 6A is a graph presenting a dose dependency of an inhibitory activity of an antibody (210309-1-C) on mouse LPA1.
Figure 6B:
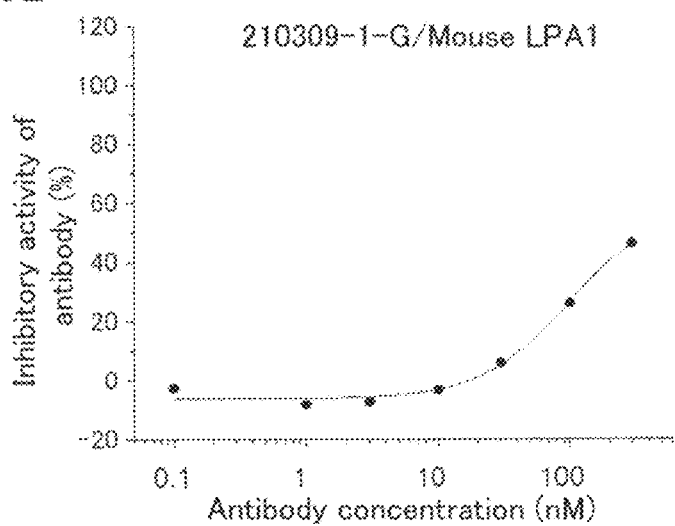
FIG. 6B is a graph presenting a dose dependency of an inhibitory activity of an antibody (210309-1-G) on mouse LPA1.
Figure 6C:
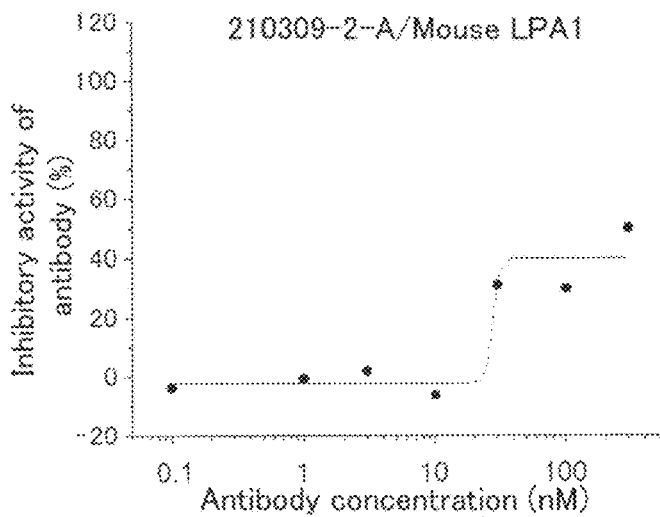
FIG. 6C is a graph presenting a dose dependency of an inhibitory activity of an antibody (210309-2-A) on mouse LPA1.
Figure 6D:
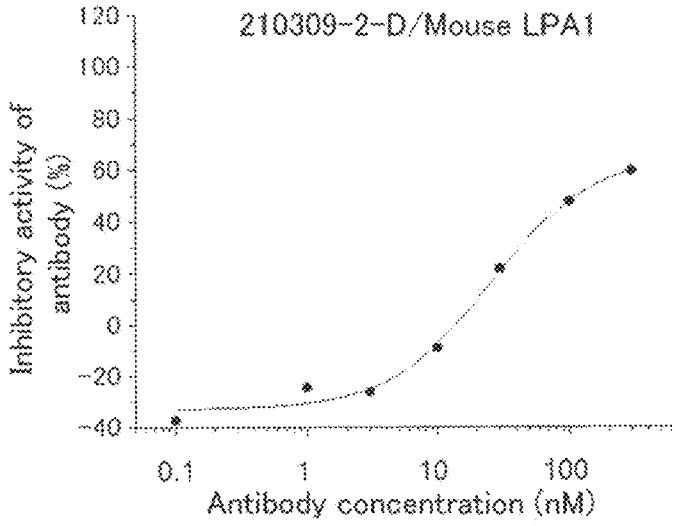
FIG. 6D is a graph presenting a dose dependency of an inhibitory activity of an antibody (210309-2-D) on mouse LPA1.
Figure 6H:
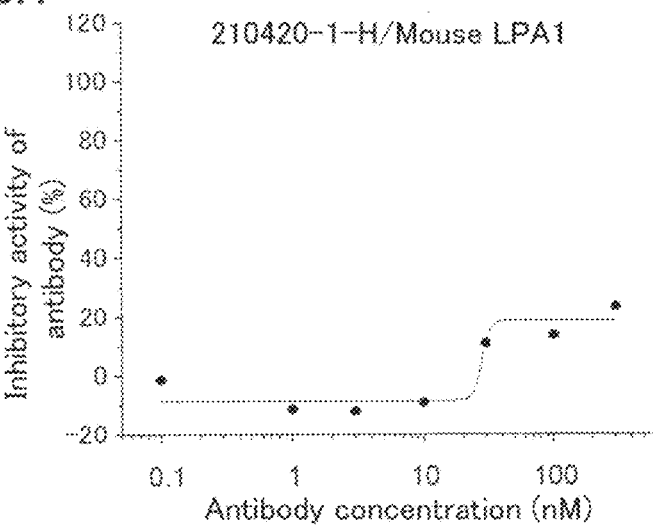
FIG. 6H is a graph presenting a dose dependency of an inhibitory activity of an antibody (210420-1-H) on mouse LPA1.
Figure 6I:
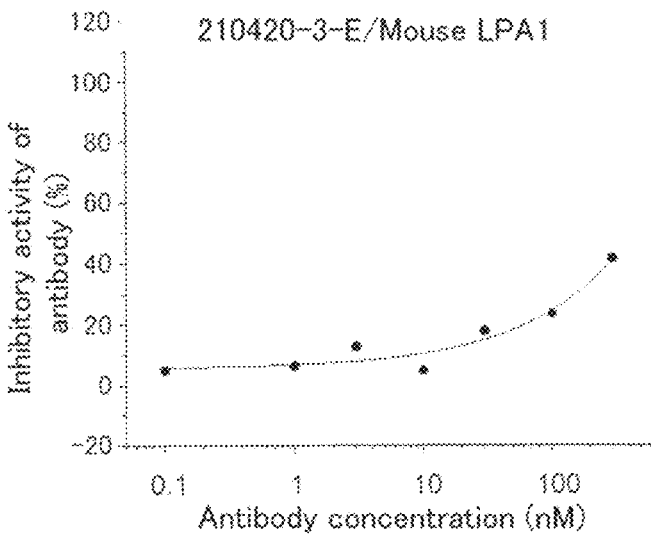
FIG. 6I is a graph presenting a dose dependency of an inhibitory activity of an antibody (210420-3-E) on mouse LPA1.
Figure 6J:
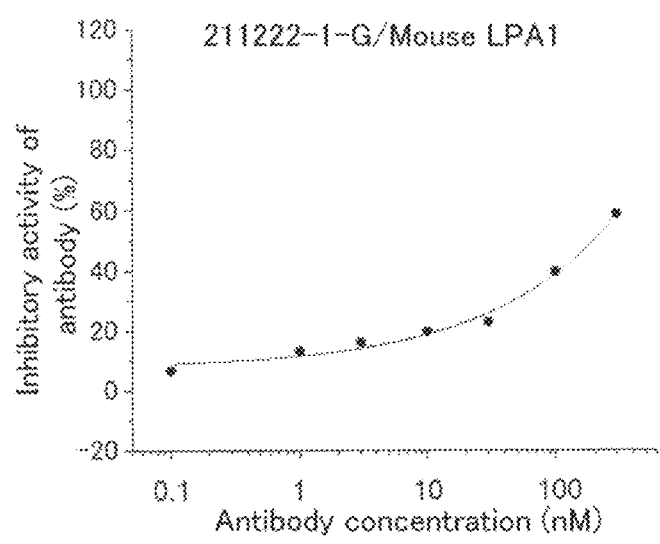
FIG. 6J is a graph presenting a dose dependency of an inhibitory activity of an antibody (211222-1-G) on mouse LPA1.
Figure 6K:
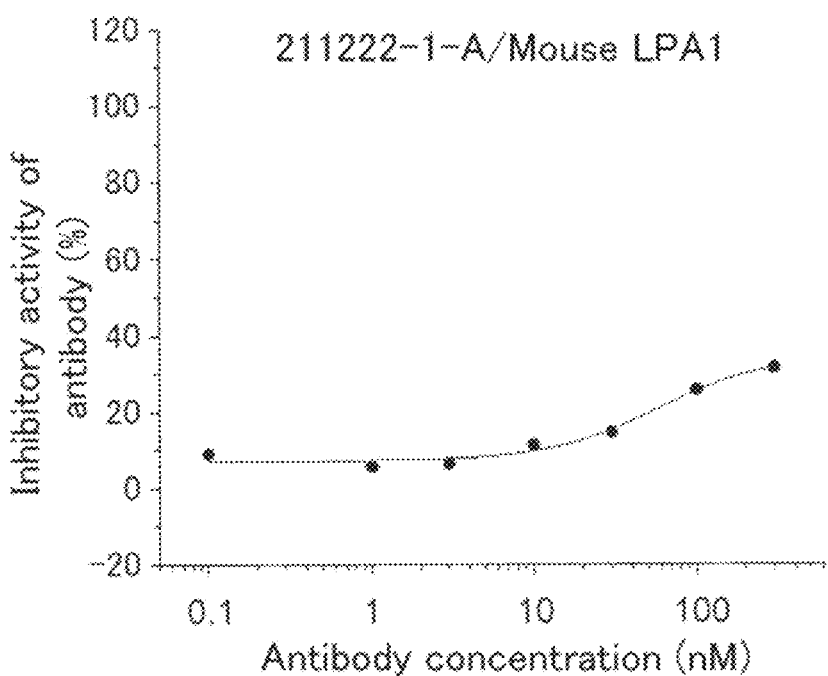
FIG. 6K is a graph presenting a dose dependency of an inhibitory activity of an antibody (211222-1-A) on mouse LPA1.

Next, the binding of the LPA1 antibody to the LPA1 endogenously expressed on the cell surface was evaluated. This was verified using a human lung-derived fibroblast cell line (IMIR-90) that had been confirmed to express the human LPA1 gene. The binding properties of 10 μg/mL each of purified LPA1 antibodies and a mouse isotype control antibody were measured by a flow cytometer (Agilent Novocyte) according to the same procedure as above. As a result, the eleven antibodies were confirmed to bind specifically to IMIR-90. FIG. 4 presents histograms in which the eleven antibodies were compared with the mouse isotype control antibody.

[Example 7] Evaluation of Intracellular cAMP
Signaling Inhibition

The antibodies produced in Example 6 were subjected to the following test.

Changes in a concentration of intracellular cyclic adenosine monophosphate (cAMP) were measured using LANCE Ultra cAMP Kit (PerkinElmer, Inc.) according to the method in Example 3. To 12.5 μL of the human LPA1-stably expressing CHO cell and mouse LPA1-stably expressing CHO cell at a cell concentration of $2 \times 10^5$ cells/mL, 6.25 μL of the purified LPA1 antibody or an LPA1 low molecule weight antagonist BMS-986278 (MedKoo Biosciences, Inc.) diluted stepwise was added and allowed to stand at room temperature for 15 minutes. Furthermore, to this mixture, 6.25 μL of a mixture of 12 μM Forskolin (Merck KGaA) (final concentration: 3 μM) and 200 nM oleoyl-L-α-lysophosphatidic acid sodium salt (final concentration: 50 nM) was added and allowed to stand at room temperature for 30 minutes, and then the cAMP concentration was measured according to the method in Example 3. For an inhibition rate (%), a value measured in adding Forskolin and the oleoyl-L-α-lysophosphatidic acid was standardized as 0% inhibition rate and a value measured in adding only Forskolin was standardized as 100% inhibition rate, and the inhibition rate was calculated as a relative intracellular cAMP signaling inhibition rate (%). The concentration of each antibody was plotted on the vertical axis, and the inhibition rate (%) was plotted on the horizontal axis. The dose dependency of the inhibitory activity of each antibody against human LPA1 was presented in FIG. 5A to FIG. 5K, and the dose dependency of the inhibitory activity of each antibody against mouse LPA1 was presented in FIG. 6A to FIG. 6K. The results showed that all of the eleven antibodies dose-dependently inhibited lysophosphatidic acid-induced intracellular cAMP signaling in the human and mouse LPA1- expressing CHO cells, and had an activity of blocking the LPA1-dependent cell functions.

Figure 7A:
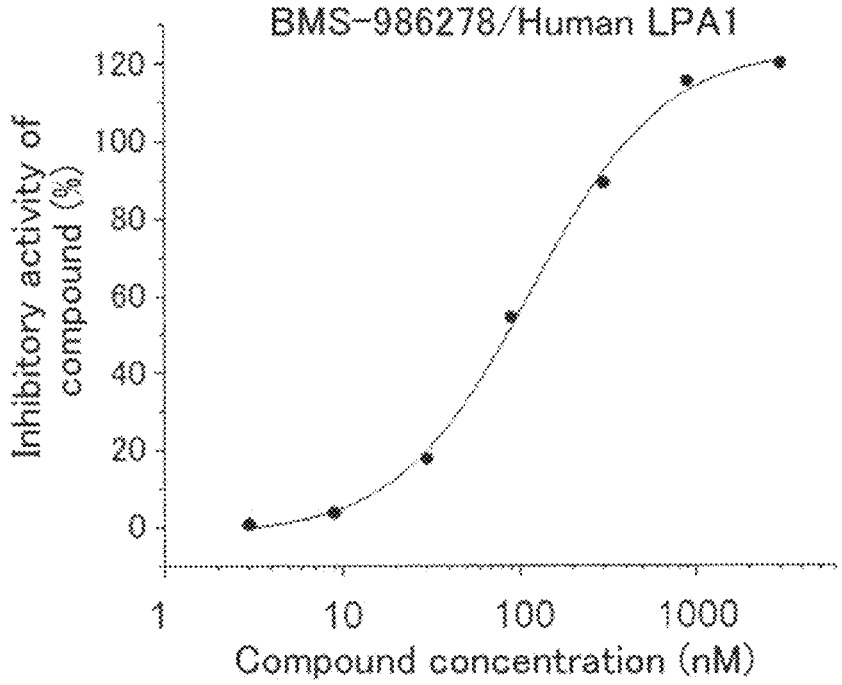
FIG. 7A is a graph presenting a dose dependency of an inhibitory activity of BMS-986278 on human LPA1.
Figure 7B:
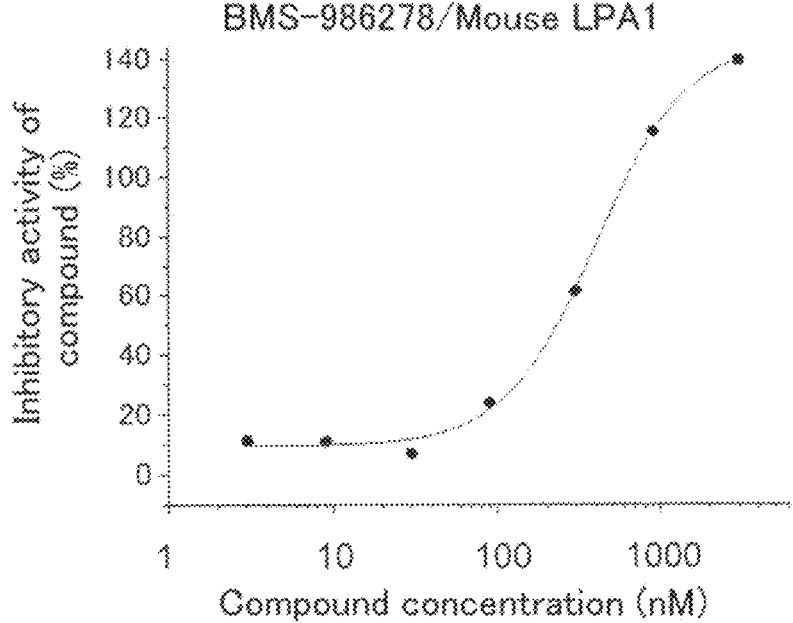
FIG. 7B is a graph presenting a dose dependency of an inhibitory activity of BMS-986278 on mouse LPA1.

In three independent tests on the intracellular cAMP signaling inhibition, 50% inhibitory concentrations (IC50) were calculated, and their averages and standard deviations are presented in Table 5. The dose dependencies of the lysophosphatidic acid-induced intracellular cAMP signaling inhibition by BMS-986278 in the human and mouse LPA1-expressing CHO cells are presented in FIG. 7A and FIG. 7B respectively. The IC50 values of BMS-986278 against the human and mouse LPA1 were 83 nM and 232 nM respectively. The results showed that all of the eleven antibodies had IC50 values of the activity of blocking the human LPA1-dependent cell functions, equal to or superior to that of BMS-986278.

TABLE 5

| | Intracellular cAMP signaling inhibition IC50 (nM) | |
| Antibody | Human LPA1-stably expressing cell | Mouse LPA1-stably expressing cell |
| --- | --- | --- |
| 210309-1-C | 25.1 ± 0.0 | — |
| 210309-1-G | 40.9 ± 3.2 | 197.3 ± 11.6 |
| 210309-2-A | 21.8 ± 3.5 | — |
| 210309-2-D | 18.0 ± 0.6 | 163.1 ± 62.7 |
| 210309-4-A | 5.3 ± 0.5 | 23.8 ± 6.1 |
| 210310-1-D | 60.5 ± 20.7 | — |
| 210420-4-E | 48.3 ± 34.9 | 124.0 ± 0.0 |
| 210420-1-H | 49.1 ± 0.0 | — |
| 210420-3-E | 33.1 ± 33.8 | 114.4 ± 51.2 |
| 211222-1-G | 96.8 ± 37.5 | 199.0 ± 0.0 |
| 211222-1-A | 69.9 ± 35.1 | — |

Figure 8:
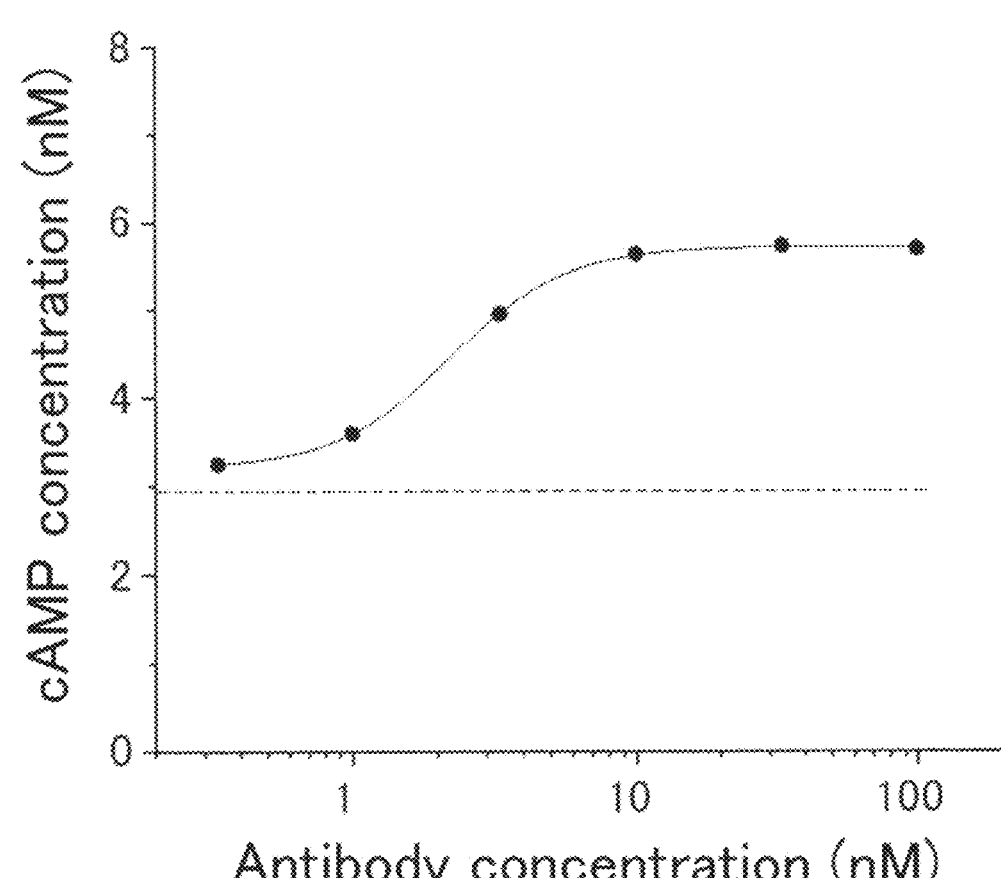
FIG. 8 is a graph presenting an evaluation result of an effect of 210309-4-A on a change in an intracellular cAMP concentration in the absence of LPA1 ligand using a human LPA1-stably expressing CHO cell.

[Example 8] Verification for Inverse Agonist Effect of LPA1 Antibody on Intracellular cAMP Signaling In the human LPA1-stably expressing CHO cells, the effect of 210309-4-A on changes in the intracellular cAMP concentration was evaluated in the absence of the LPA1 ligand. In other words, to 12.5 μL of human LPA1-stably expressing CHO cell at a cell concentration of $2 \times 10^5$ cells/mL, 6.25 μL of 210309-4-A used in Example 6 and diluted stepwise was added, and allowed to stand at room temperature for 15 minutes. To this mixture, 6.25 μL of 12 μMForskolin (final concentration: 3 μM) was further added and allowed to stand at room temperature for 30 minutes, and a cAMP concentration was measured. FIG. 8 presents a graph in which the antibody concentration is plotted on the vertical axis and the cAMP concentration (nM) is plotted on the horizontal axis. In FIG. 8, the dotted line indicates the cAMP concentration (2.9 nM) with Forskolin stimulation alone. That means, 210309-4-A showed the characteristic of the inverse agonist because it dose-dependently increased the cAMVP level. As a result of subjecting the other ten LPA1 antibodies to the same test, they showed the characteristic of the inverse agonist because they dose-dependently increased the cAMVP level. It was revealed that these antibodies could LPA1 ligand-independently block the LPA1 receptor-dependent cell functions.

Figures 9, 10A, 10B:
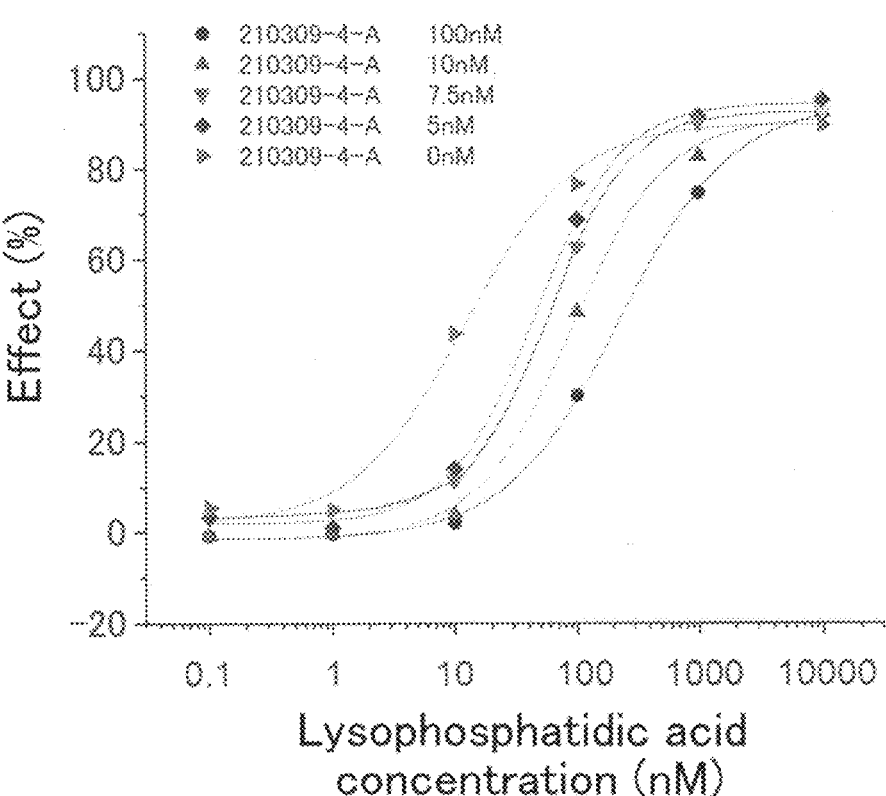
FIG. 9 is a graph presenting a dose-response curve of lysophosphatidic acid at various 210309-4-A concentrations.
FIG. 10A is an explanatory diagram presenting an alignment of a heavy chain variable region of a humanized anti-LPA1 antibody.
FIG. 10B is an explanatory diagram presenting an alignment of a light chain variable region of the humanized anti-LPA1 antibody.
Figure 11A:
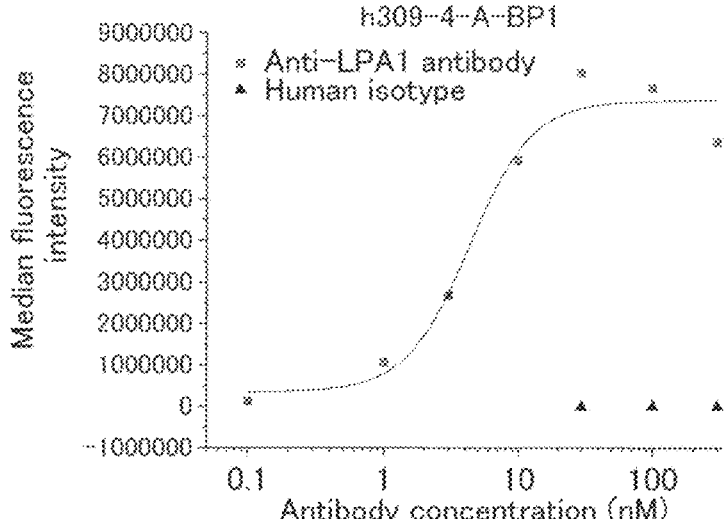
FIG. 11A is a graph presenting an evaluation result of a binding property of an antibody (h309-4-A-BP1) to a human LPA1-stably expressing CHO cell.
Figure 11B:
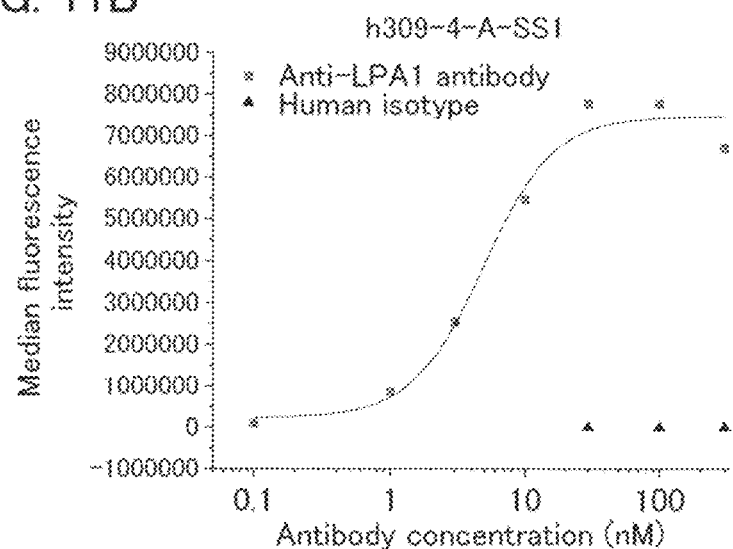
FIG. 11B is a graph presenting an evaluation result of a binding property of an antibody (h309-4-A-SS1) to a human LPA1-stably expressing CHO cell.
Figure 11C:
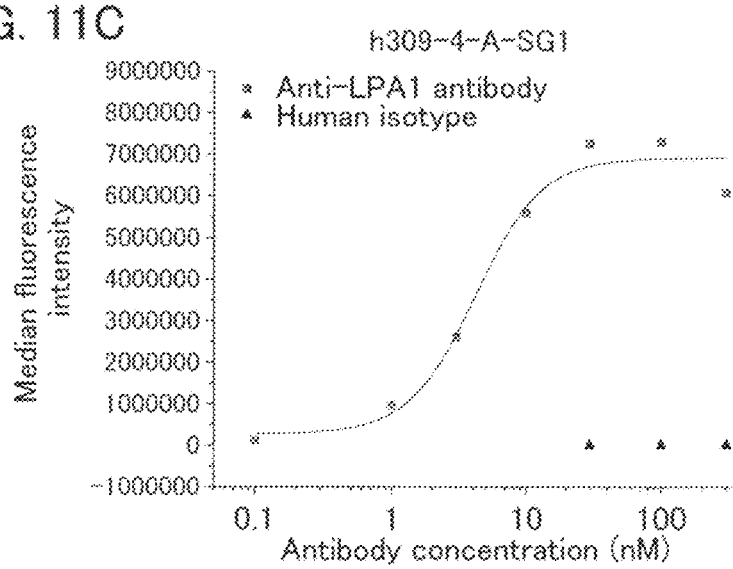
FIG. 11C is a graph presenting an evaluation result of a binding property of an antibody (h309-4-A-SG1) to a human LPA1-stably expressing CHO cell.
Figure 11D:
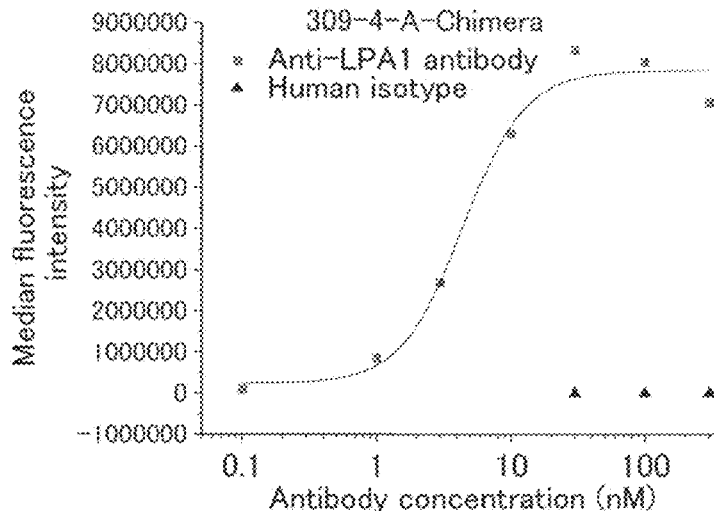
FIG. 11D is a graph presenting an evaluation result of a binding property of an antibody (309-4-A-Chimera) to a human LPA1-stably expressing CHO cell.
Figure 11E:
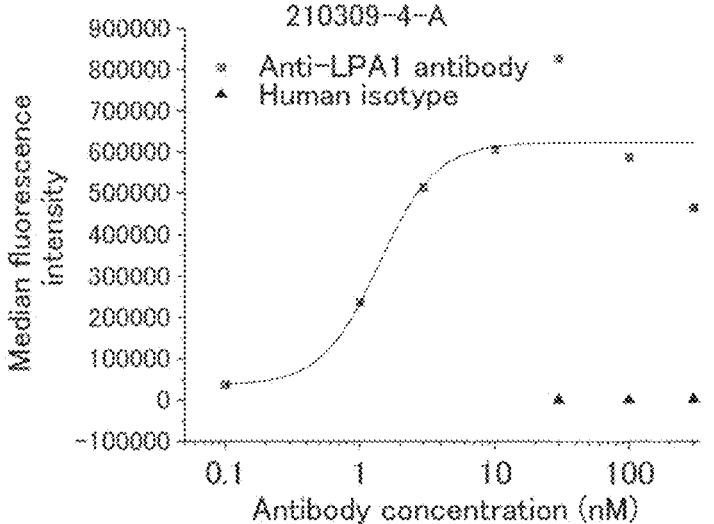
FIG. 11E is a graph presenting an evaluation result of a binding property of an antibody (210309-4-A) to a human LPA1-stably expressing CHO cell.
Figure 12A:
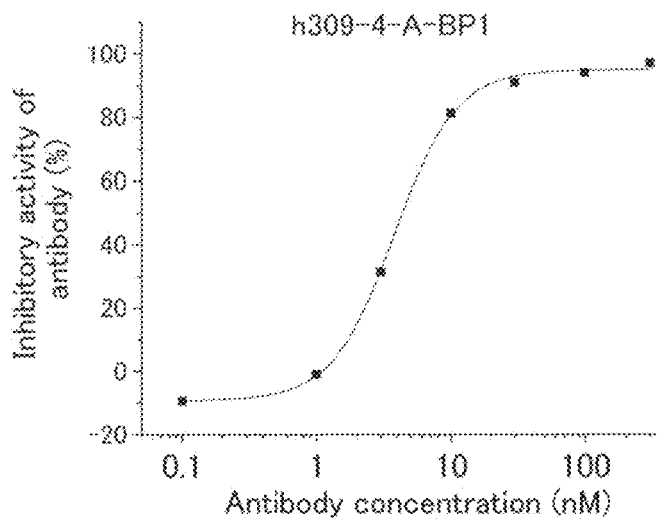
FIG. 12A is a graph presenting a dose dependency of an inhibitory activity of an antibody (h309-4-A-BP1) on human LPA1.
Figure 12B:
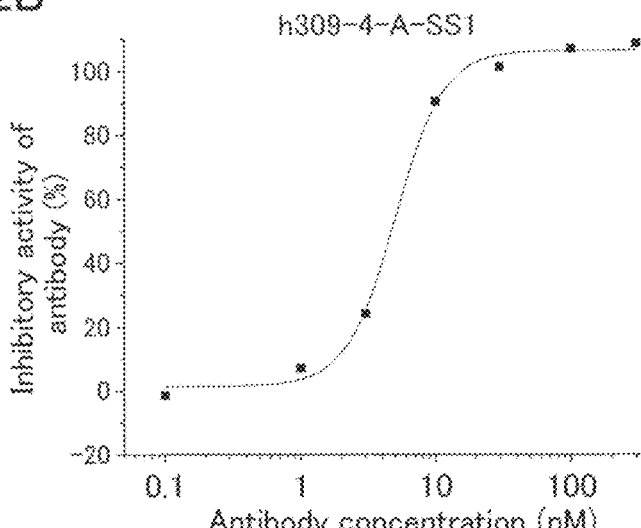
FIG. 12B is a graph presenting a dose dependency of an inhibitory activity of an antibody (h309-4-A-SS1) on human LPA1.
Figure 12C:
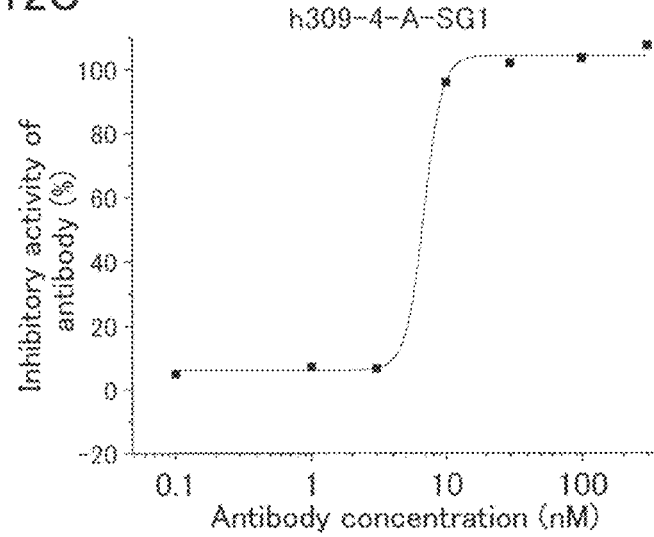
FIG. 12C is a graph presenting a dose dependency of an inhibitory activity of an antibody (h309-4-A-SG1) on human LPA1.
Figure 12D:
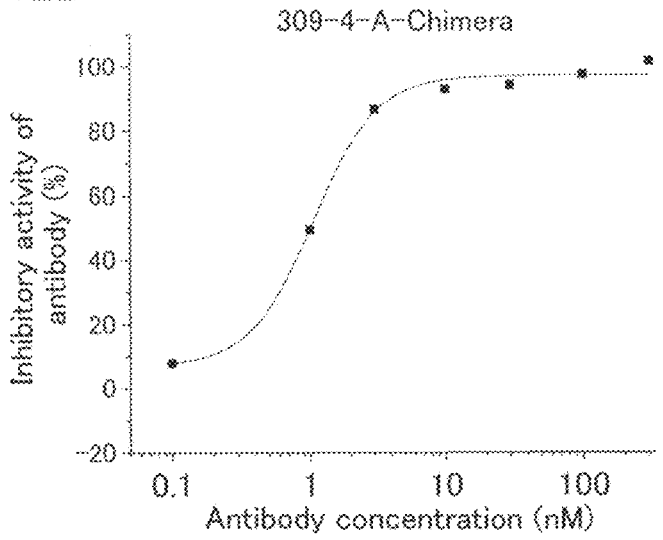
FIG. 12D is a graph presenting a dose dependency of an inhibitory activity of an antibody (309-4-A-Chimera) on human LPA1.

[Example 9] Verification for Intracellular cAMVP Signaling Inhibition Manner of LPA1 Antibody In the human LPA1-stably expressing CHO cell, the effect of various concentrations of 210309-4-A on a dose-response curve of lysophosphatidic acid as the LPA1 ligand was evaluated. In other words, 6.25 μL of 210309-4-A used in Example 6 (final concentration: 0.5, 7.5, 10, and 100 nM) at a constant concentration was added to 12.5 μL of the human LPA1-stably expressing CHO cell at a cell concentration of $2 \times 10^5$ cells/mL, and allowed to stand at room temperature for 15 minutes. To this mixture, 6.25 μL of a mixture of 12 M Forskolin (final concentration: 3 μM) and oleoyl-L-α-lysophosphatidic acid sodium salt (final concentration: 0.1 to 1000 nM) was further added, then allowed to stand at room temperature for 30 minutes, and then a cAMP concentration was measured. FIG. 9 presents a dose-response curve of lysophosphatidic acid at each antibody concentration. The curve showed a characteristic of competitive inhibition because the dose-response curve shifted rightward as the antibody concentration increased.

[Example 10] Preparation of Humanized Anti-LPA1 Antibody

A case of 210309-4-A will be described as an example. To prepare a humanized antibody implanted with the CDR of 210309-4-A, a human framework was selected on the basis of a homology between 210309-4-A and human germline VH and VK genes. In order to support a predicted antibody conformation of 210309-4-A, multiple antibodies with variation of the selected human germline VH and VL sequences, "h309-4-A-BP1", "h309-4-A-SS1", and "h309-4-A-SG1" were designed based on a computer modeling. FIG. 10A presents alignments of an h309-4-A-BP1 VH region (SEQ ID NO: 123), an h309-4-A-SS1 VH region (SEQ ID NO: 125), an h309-4-A-SG1 VH region (SEQ ID NO: 127), and a 210309-4-A VH region (SEQ ID NO: 7). FIG. 10B presents alignments of an h309-4-A-BP1 VL region (SEQ ID NO: 124), an h309-4-A-SS1 VL region (SEQ ID NO: 126), an h309-4-A-SG1 VL region (SEQ ID NO: 128), and a 210309-4-A VL region (SEQ ID NO: 9).

Artificial genes were synthesized, in which the human IgG1 heavy chain constant region (including LALA variant) (SEQ ID NO: 129) was connected to the VH region and the human IgG1κ chain constant region (SEQ ID NO: 130) was connected to the VL region in h309-4-A-BP1, h309-4-A-SS1, and h309-4-A-SG1. As a comparable, an artificial gene of a chimeric anti-LPA1 antibody "309-4-A-Chimera" was also synthesized, in which the human IgG1 heavy chain constant region (including LALA variant) was connected to the VH region and the human IgG1κ chain constant region was connected to the VL region in 210309-4-A in 210309-4-A. The artificial genes were introduced into CHO cells, and, from the CHO cell culture supernatant, purified antibodies were produced by affinity chromatography and subjected to the following test. As a result of assaying purities by SDS-PAGE, all the purified antibodies were confirmed to have a purity of 90% or higher.

Subsequently, the binding activity of the human LPA1-stably expressing CHO cell to human LPA1 was measured according to the method in Example 6. A graph was created, in which a concentration of the antibody was plotted on the vertical axis, and a median fluorescence intensity of the flow cytometer histogram was plotted on the horizontal axis. The results of binding of each antibody to the human LPA1-stably expressing CHO cell are presented in FIG. 11A to FIG. 11E, and the calculated 50% binding concentrations (EC50) are presented in Table 6. The intracellular cAMP signaling inhibitory activity was also measured according to the method in Example 7. A graph was created, in which a concentration and an inhibition rate (%) of each antibody were plotted on the vertical axis and the horizontal axis respectively. The dose dependencies of the inhibitory activity of each antibody against human LPA1 are presented in FIG. 12A to FIG. 12E, and the calculated 50% inhibitory concentrations ($IC_{50}$) of each antibody are presented in Table 7.

As shown in these results, the binding and inhibitory activities of 309-4-A-Chimera were equivalent to those of 210309-4-A, indicating that the conversion of the human antibody to the constant region did not affect the binding and inhibitory activities. Furthermore, the binding and inhibitory activities of h309-4-A-BP1, h309-4-A-SS1, and h309-4-A-SG1 designed as humanized LPA1 antibodies were equivalent to those of 309-4-A-Chimera, indicating that the binding and inhibitory activities of all designs were maintained after the humanization.

TABLE 6

| Antibody | Binding to LPA1-stably expressing cell EC50 (nM) | |
| | Human LPA1-stably expressing cell | |
| --- | --- | --- |
| h309-4-A-BP1 | 4.3 | |
| h309-4-A-SS1 | 4.9 | |

TABLE 6-continued

| Antibody | Binding to LPA1-stably expressing cell EC50 (nM) | |
| | Human LPA1-stably expressing cell | |
| --- | --- | --- |
| h309-4-A-SG1 | 4.2 | |
| 309-4-A-Chimera | 4.4 | |
| 210309-4-A | 1.4 | |

TABLE 7

| Antibody | Intracellular cAMP signaling inhibition IC50 (nM) | |
| | Human LPA1-stably expressing cell | |
| --- | --- | --- |
| h309-4-A-BP1 | 4.4 | |
| h309-4-A-SS1 | 5.2 | |
| h309-4-A-SG1 | 5.7 | |
| 309-4-A-Chimera | 1.0 | |
| 210309-4-A | 4.5 | |

The amino acid sequences of SEQ ID NO: 123 to 130 are presented in Table 8.

TABLE 8

| SEQ ID NO: | Antibody ID | Content | Amino acid sequence |
| --- | --- | --- | --- |
| 123 | h309-4-A-BP1 | Heavy chain variable region | QVQLVQSGAEVKKPGASVKVSCKASGYTFTSYGISWVRQAPGQGL EWMGEIYPRSGNTYYNEKFKGRVTLTADKSTSTAYMELRSLTSED TAVYFCARESISRRLGWNEDVWGQGTTVTVSS |
| 124 | | Light chain variable region | DIQMTQSPSSLSASVGDTVTITCRASENIYSFLAWYQQKPGKAPK LLIYNAKTLTEGVPSRFSGSGSGTHFSLTINSLQPEDEGIYYCQH HYGPPLTFGQGTKLEIK |
| 125 | h309-4-A-SS1 | Heavy chain variable region | QVQLQESGPGLVKPSETLSLTCTASGYTFTSYGISWVRQTPGKGL EWIGEIYPRSGNTYYNEKFKGRATLSADKSKNQASLKLKSVTAAD TAIYFCARESISRRLGWNFDVWGRGTLVTVSG |
| 126 | | Light chain variable region | DIQMTQTPSSLSASVGDRVTITCRASENIYSFLAWYQQKPGEAPK RVVYNAKTLTEGVPSRFSGSGSGTDFTLTISSLQPEDFATYYCQH HYGPPLTFGQGTKLEIK |
| 127 | h309-4-A-SG1 | Heavy chain variable region | QVQLVQSGAEVKKPGASVKVSCKASGYTFTSYGISWVRQAPGQGL EWIGEIYPRSGNTYYNEKFKGRATLTADKSTSTAYMELRSLRSDD TAVYFCARESISRRLGWNEDVWGTGTTVTVSS |
| 128 | | Light chain variable region | DIQMTQSPSSLSASVGDRVTITCRASENIYSFLAWYQQKPGKAPK LVVYNAKTLTEGVPSRFSGSGSGTDFTLTISSLQPEDFATYYCQH HYGPPLTFGAGTKLELK |
| 129 | HC-LALA | Heavy chain constant region (including LALA variant) | ASTKGPSVFPLAPSSKSTSGGTAALGCLVKDYFPEPVTVSWNSGA LTSGVHTFPAVLQSSGLYSLSSVVTVPSSSLGTQTYICNVNHKPS NTKVDKKVEPKSCDKTHTCPPCPAPEAAGGPSVFLFPPKPKDTLM ISRTPEVTCVVVDVSHEDPEVKFNWYVDGVEVHNAKTKPREEQYN STYRVVSVLTVLHQDWLNGKEYKCKVSNKALPAPIEKTISKAKGQ PREPQVYTLPPSRDELTKNQVSLTCLVKGFYPSDIAVEWESNGQP ENNYKTTPPVLDSDGSFFLYSKLTVDKSRWQQGNVFSCSVMHEAL HNHYTQKSLSLSPGK |
| 130 | LC | Light chain constant region | RTVAAPSVFIFPPSDEQLKSGTASVVCLLNNFYPREAKVQWKVDN ALQSGNSQESVTEQDSKDSTYSLSSTLTLSKADYEKHKVYACEVT HQGLSSPVTKSENRGEC |

The invention claimed is:

1. An antibody that specifically binds to an extracellular domain of human LPA1, wherein the antibody has an activity of blocking an LPA1-dependent cell function, the antibody has an inverse agonist effect, and the antibody satisfies any one of the following (AB1) to (AB11):

(AB1) comprising a heavy chain CDR1 including an amino acid sequence represented by SEQ ID NO: 1, a heavy chain CDR2 including an amino acid sequence represented by SEQ ID NO: 2, a heavy chain CDR3 including an amino acid sequence represented by SEQ ID NO: 3, a light chain CDR1 including an amino acid sequence represented by SEQ ID NO: 4, a light chain CDR2 including an amino acid sequence represented by SEQ ID NO: 5, and a light chain CDR3 including an amino acid sequence represented by SEQ ID NO: 6;

(AB2) comprising a heavy chain CDR1 including an amino acid sequence represented by SEQ ID NO: 11, a heavy chain CDR2 including an amino acid sequence represented by SEQ ID NO: 12, a heavy chain CDR3 including an amino acid sequence represented by SEQ ID NO: 13, a light chain CDR1 including an amino acid sequence represented by SEQ ID NO: 14, a light chain CDR2 including an amino acid sequence represented by SEQ ID NO: 15, and a light chain CDR3 including an amino acid sequence represented by SEQ ID NO: 16;

(AB3) comprising a heavy chain CDR1 including an amino acid sequence represented by SEQ ID NO: 21, a heavy chain CDR2 including an amino acid sequence represented by SEQ ID NO: 22, a heavy chain CDR3 including an amino acid sequence represented by SEQ ID NO: 23, a light chain CDR1 including an amino acid sequence represented by SEQ ID NO: 24, a light chain CDR2 including an amino acid sequence represented by SEQ ID NO: 25, and a light chain CDR3 including an amino acid sequence represented by SEQ ID NO: 26;

(AB4) comprising a heavy chain CDR1 including an amino acid sequence represented by SEQ ID NO: 31, a heavy chain CDR2 including an amino acid sequence represented by SEQ ID NO: 32, a heavy chain CDR3 including an amino acid sequence represented by SEQ ID NO: 33, a light chain CDR1 including an amino acid sequence represented by SEQ ID NO: 34, a light chain CDR2 including an amino acid sequence represented by SEQ ID NO: 35, and a light chain CDR3 including an amino acid sequence represented by SEQ ID NO: 36;

(AB5) comprising a heavy chain CDR1 including an amino acid sequence represented by SEQ ID NO: 41, a heavy chain CDR2 including an amino acid sequence represented by SEQ ID NO: 42, a heavy chain CDR3 including an amino acid sequence represented by SEQ ID NO: 43, a light chain CDR1 including an amino acid sequence represented by SEQ ID NO: 44, a light chain CDR2 including an amino acid sequence represented by SEQ ID NO: 45, and a light chain CDR3 including an amino acid sequence represented by SEQ ID NO: 46;

(AB6) comprising a heavy chain CDR1 including an amino acid sequence represented by SEQ ID NO: 51, a heavy chain CDR2 including an amino acid sequence represented by SEQ ID NO: 52, a heavy chain CDR3 including an amino acid sequence represented by SEQ ID NO: 53, a light chain CDR1 including an amino acid sequence represented by SEQ ID NO: 54, a light chain CDR2 including an amino acid sequence represented by SEQ ID NO: 55, and a light chain CDR3 including an amino acid sequence represented by SEQ ID NO: 56;

(AB7) comprising a heavy chain CDR1 including an amino acid sequence represented by SEQ ID NO: 61, a heavy chain CDR2 including an amino acid sequence represented by SEQ ID NO: 62, a heavy chain CDR3 including an amino acid sequence represented by SEQ ID NO: 63, a light chain CDR1 including an amino acid sequence represented by SEQ ID NO: 64, a light chain CDR2 including an amino acid sequence represented by SEQ ID NO: 65, and a light chain CDR3 including an amino acid sequence represented by SEQ ID NO: 66;

(AB8) comprising a heavy chain CDR1 including an amino acid sequence represented by SEQ ID NO: 71, a heavy chain CDR2 including an amino acid sequence represented by SEQ ID NO: 72, a heavy chain CDR3 including an amino acid sequence represented by SEQ ID NO: 73, a light chain CDR1 including an amino acid sequence represented by SEQ ID NO: 74, a light chain CDR2 including an amino acid sequence represented by SEQ ID NO: 75, and a light chain CDR3 including an amino acid sequence represented by SEQ ID NO: 76;

(AB9) comprising a heavy chain CDR1 including an amino acid sequence represented by SEQ ID NO: 81, a heavy chain CDR2 including an amino acid sequence represented by SEQ ID NO: 82, a heavy chain CDR3 including an amino acid sequence represented by SEQ ID NO: 83, a light chain CDR1 including an amino acid sequence represented by SEQ ID NO: 84, a light chain CDR2 including an amino acid sequence represented by SEQ ID NO: 85, and a light chain CDR3 including an amino acid sequence represented by SEQ ID NO: 86;

(AB10) comprising a heavy chain CDR1 including an amino acid sequence represented by SEQ ID NO: 91, a heavy chain CDR2 including an amino acid sequence represented by SEQ ID NO: 92, a heavy chain CDR3 including an amino acid sequence represented by SEQ ID NO: 93, a light chain CDR1 including an amino acid sequence represented by SEQ ID NO: 94, a light chain CDR2 including an amino acid sequence represented by SEQ ID NO: 95, and a light chain CDR3 including an amino acid sequence represented by SEQ ID NO: 96; and (AB11) comprising a heavy chain CDR1 including an amino acid sequence represented by SEQ ID NO: 101, a heavy chain CDR2 including an amino acid sequence represented by SEQ ID NO: 102, a heavy chain CDR3 including an amino acid sequence represented by SEQ ID NO: 103, a light chain CDR1 including an amino acid sequence represented by SEQ ID NO: 104, a light chain CDR2 including an amino acid sequence represented by SEQ ID NO: 105, and a light chain CDR3 including an amino acid sequence represented by SEQ ID NO: 106.

2. The antibody according to claim 1, wherein the antibody is a humanized antibody or a chimeric antibody.

3. A pharmaceutical composition comprising the antibody according claim 2 as an active ingredient and a pharmaceutically acceptable carrier.

4. A nucleic acid encoding the antibody according to claim 2.

5. A cell comprising the nucleic acid according to claim 4.

6. The antibody according to claim 1, wherein the modified antibody is an antibody-drug conjugate and, the drug is selected from the group consisting of an anti-fibrosis agent, a low molecular weight anticancer drug, a biologically active protein or polypeptide, a radioisotope, and a light absorber.

7. A pharmaceutical composition comprising the antibody according claim 6 as an active ingredient and a pharmaceutically acceptable carrier.

8. A nucleic acid encoding the antibody according to claim 1.

9. A cell comprising the nucleic acid according to claim 8.

10. A pharmaceutical composition comprising the antibody according to claim 1 as an active ingredient and a pharmaceutically acceptable carrier.

11. An antibody that specifically binds to an extracellular domain of human LPA1, wherein the antibody has an activity of blocking an LPA1-dependent cell function, the antibody has an inverse agonist effect, and the antibody satisfies any one of the following (C1) to (C11):

(C1) comprising a heavy chain variable region including an amino acid sequence represented by SEQ ID NO: 7 and a light chain variable region including an amino acid sequence represented by SEQ ID NO: 9;

(C2) comprising a heavy chain variable region including an amino acid sequence represented by SEQ ID NO: 17 and a light chain variable region including an amino acid sequence represented by SEQ ID NO: 19;

(C3) comprising a heavy chain variable region including an amino acid sequence represented by SEQ ID NO: 27 and a light chain variable region including an amino acid sequence represented by SEQ ID NO: 29;

(C4) comprising a heavy chain variable region including an amino acid sequence represented by SEQ ID NO: 37 and a light chain variable region including an amino acid sequence represented by SEQ ID NO: 39;

(C5) comprising a heavy chain variable region including an amino acid sequence represented by SEQ ID NO: 47 and a light chain variable region including an amino acid sequence represented by SEQ ID NO: 49;

(C6) comprising a heavy chain variable region including an amino acid sequence represented by SEQ ID NO: 57 and a light chain variable region including an amino acid sequence represented by SEQ ID NO: 59;

(C7) comprising a heavy chain variable region including an amino acid sequence represented by SEQ ID NO: 67 and a light chain variable region including an amino acid sequence represented by SEQ ID NO: 69;

(C8) comprising a heavy chain variable region including an amino acid sequence represented by SEQ ID NO: 77 and a light chain variable region including an amino acid sequence represented by SEQ ID NO: 79;

(C9) comprising a heavy chain variable region including an amino acid sequence represented by SEQ ID NO: 87 and a light chain variable region including an amino acid sequence represented by SEQ ID NO: 89;

(C10) comprising a heavy chain variable region including an amino acid sequence represented by SEQ ID NO: 97 and a light chain variable region including an amino acid sequence represented by SEQ ID NO: 99; and (C11) comprising a heavy chain variable region including an amino acid sequence represented by SEQ ID NO: 107 and a light chain variable region including an amino acid sequence represented by SEQ ID NO: 109.

* * * * *